United States Patent [19]

Soma et al.

[11] 4,162,246

[45] Jul. 24, 1979

[54] HYDANTOIN DERIVATIVES AND THEIR USE AS POLYMER STABILIZERS

[75] Inventors: Nobuo Soma; Syoji Morimura; Takao Yoshioka; Tomoyuki Kurumada, all of Hiromachi, Japan

[73] Assignee: Sankyo Company Limited, Tokyo, Japan

[21] Appl. No.: 860,172

[22] Filed: Dec. 13, 1977

[30] Foreign Application Priority Data

Dec. 27, 1976 [JP] Japan ................................ 51-157784

[51] Int. Cl.$^2$ ...................... C07D 471/10; C08K 5/34
[52] U.S. Cl. ............................ 260/45.8 NT; 106/176; 260/45.85 B; 546/20; 544/222
[58] Field of Search .................. 260/45.8 NT, 293.66, 260/293.63, 293.64; 544/222

[56] References Cited

U.S. PATENT DOCUMENTS

| | | | |
|---|---|---|---|
| 2,778,825 | 1/1957 | Melamed | 106/176 |
| 3,941,744 | 3/1976 | Murayama et al. | 260/45.8 NT |
| 3,975,462 | 8/1976 | Murayama et al. | 260/880 R |
| 4,066,615 | 1/1978 | Murayama et al. | 260/293.66 |
| 4,097,587 | 6/1978 | Soma | 260/293.66 |

*Primary Examiner*—Hosea E. Taylor
*Assistant Examiner*—R. A. White
*Attorney, Agent, or Firm*—Toren, McGeady and Stanger

[57] ABSTRACT

Hydantoin derivatives in which two or three piperidine spiro hydantoin residues are attached by means of substituted alkylene groups or polyoxyalkylene groups whose oxyalkylene chain is optionally interrupted by one or more phenylene or cyclohexylene groups or by means of substituted isocyanurate or glyceryl groups and, where they exist, acid addition salts thereof, are valuable as stabilizers for synthetic polymers.

11 Claims, No Drawings

HYDANTOIN DERIVATIVES AND THEIR USE AS POLYMER STABILIZERS

BACKGROUND OF THE INVENTION

This invention relates to certain novel hydantoin derivatives and to their use as stabilizers for synthetic polymers and provides processes for their preparation. More specifically, it is concerned with compounds having two or three hydantoin residues.

Certain classes of hydantoin derivatives are known to be useful stabilizers for synthetic polymers; such derivatives are disclosed in, for example, U.S. Pat. Nos. 3,542,729, 3,639,409, 3,705,126, 3,898,303, 3,941,744 and 3,975,462, Japanese Patent Application No. 49-72332, as laid open to public inspection, and German Offenlegungsschrift No. 2,623,464.

However, these known stabilizers have a number of disadvantages. For example, some of them, in spite of being good light stabilizers, are relatively volatile and are therefore of no practical use in the stabilization of synthetic polymers since they volatilize at processing temperatures and may also volatilize during prolonged storage of the stabilized articles. Others of these compounds can easily be extracted from synthetic polymers with water or organic solvents and, again, are of little practical use for the stabilization of synthetic polymers. Though hydantoin derivatives in which, e.g. two or three 2,2,6,6-tetramethyl-1,3,8-triazaspiro[4.5]decane-2,4-dione are linked to certain bridging member such as an alkylene group at their 3-position are known, hydantoin derivatives in which, e.g. two or three of the residues are linked to 2,2-bis[4-(2-hydroxypropoxy)-phenyl]propane have not been discoved.

BRIEF SUMMARY OF THE INVENTION

It is, therefore, an object of the present invention to provide novel hydantoin derivatives useful as stabilizers for synthetic polymers but which do not suffer the disadvantages of the known compounds.

It is a further object of the invention to provide a stabilized composition comprising a synthetic polymer and a hydantoin derivative.

It is a still further object of the invention to provide processes for the preparation of the hydantoin derivatives of the invention.

The novel hydantoin derivative of the invention has the general formula (I):

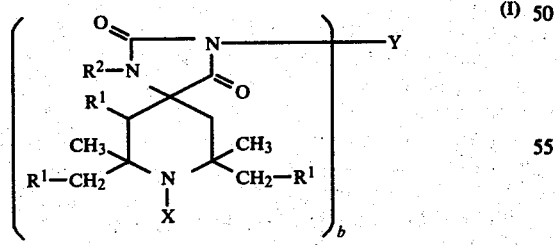

in which:
R$_6$ represents a hydrogen atom or a methyl group;
R$_2$ represents a hydrogen atom, an alkyl group having from 1 to 18 carbon atoms, an allyl group, an acetyl group or a benzyl group;
X represents a hydrogen atom, an alkyl group having from 1 to 18 carbon atoms, an alkenyl group having 3 or 4 carbon atoms, an cyanoalkyl group having 2 or 3 carbon atoms, a 2,3-epoxypropyl group, a benzyl group, an aliphatic acyl group having up to 18 carbon atoms, or a group of formulae

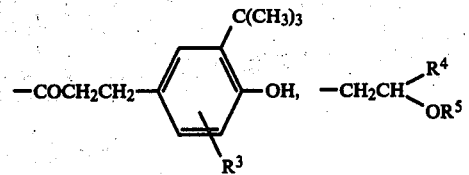

or —CH$_2$COOR$^6$
[in which:
R$^3$ represents an alkyl group having from 1 to 4 carbon atoms:
R$^4$ represents a hydrogen atom, a methyl group or a phenyl group;
R$^5$ represents a hydrogen atom, an alkyl group having from 1 to 8 carbon atoms, an allyl group, a benzyl group or an aliphatic, aromatic, araliphatic or alicyclic acyl group having up to 18 carbon atoms (wherein the aromatic moiety is unsubstituted or has one or more C$_1$–C$_4$ alkyl and/or hydroxy substituents);
R$^6$ represents an alkyl group having from 1 to 18 carbon atoms, an alkenyl group having 3 or 4 carbon atoms or a phenyl group];
b is 2 or 3; and
when b=2:
Y represents a group of formula —CH$_2$CH(OZ)CH$_2$—[OCH$_2$CH(OZ)CH$_2$]$_2$—, a group of formula —CH$_2$CH(OZ)CH$_2$—[OCH$_2$CH(R$^7$)]$_m$—OCH$_2$CH(OZ)CH$_2$—, a group of formula —CH$_2$CH(OZ)CH$_2$—[OWO—CH$_2$CH(OZ)CH$_2$]$_n$—, or a group of formula —CH$_2$CH(OZ)CH$_2$—
[in which:
m and n each represents an integer from 1 to 10;
R$^7$ represents a hydrogen atom or a methyl group:
W represents one of the groups

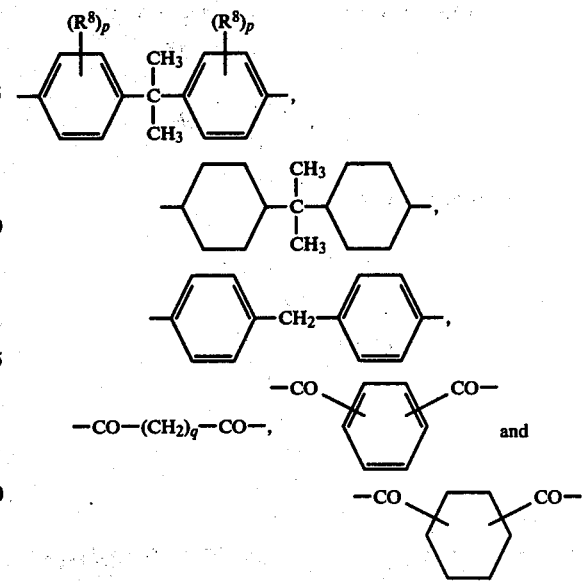

in which:
p is 0, 1 or 2;
R$^8$ represents a halogen atom;
q is an integer from 1 to 10;

Z represents a hydrogen atom, an alkyl group having from 1 to 18 carbon atoms, an allyl group, a benzyl group, an aliphatic, aromatic, araliphatic or alicyclic acyl group having up to 18 carbon atoms (in which the aromatic moiety is unsubstituted or has one or more $C_1$–$C_4$ alkyl and/or hydroxy substituents), or one of the groups

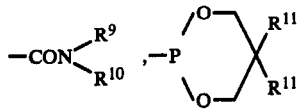

and —P(OR$^{12}$)$_2$
in which:
$R^9$ represents a hydrogen atom or an alkyl group having from 1 to 4 carbon atoms;
$R^{10}$ represents an alkyl group having from 1 to 18 carbon atoms, a phenyl group which is unsubstituted or has one or more methyl, chlorine or bromine substituents, a naphthyl group or a cyclohexyl group;
$R^{11}$ represents a hydrogen atom or an alkyl group having from 1 to 4 carbon atoms; and
$R^{12}$ represents an alkyl group having from 1 to 4 carbon atoms, a phenyl group or a group of formula

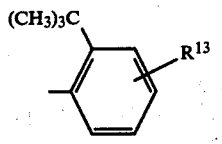

in which $R_{13}$ represents a hydrogen atom or an alkyl group having from 1 to 4 carbon atoms]; and
when b=3:
Y represents a group of formula

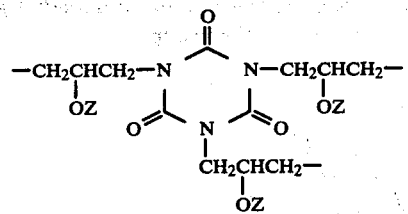

or a group of formula

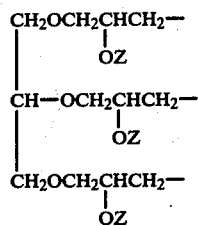

(in which Z is as defined above).

DETAILED DESCRIPTION OF INVENTION

In the compound of formula (I), when $R^2$ represents an alkyl group having from 1 to 18 carbon atoms, it may be, for example, a methyl, ethyl, n-propyl, n-butyl, octyl, dodecyl or octadecyl group, and is preferably an alkyl group having from 1 to 8 carbon atoms, most preferably a methyl group. When $R_2$ represents a group other than a hydrogen atom, it is preferred that X and Z also should represent groups other than hydrogen atoms.

When X represents an alkyl group, it may be, for example, a methyl, ethyl, n-propyl, n-butyl, octyl, dodecyl or octadecyl group, preferably an alkyl group having from 1 to 4 carbon atoms, most preferably a methyl group. When X represents an alkenyl group having 3 or 4 carbon atoms, it may be, for example, an allyl group or a 2-butenyl group, preferably an allyl group. When X represents a cyanoalkyl group having 2 or 3 carbon atoms, it is preferably a cyanomethyl or 2-cyanoethyl group. When X represents an aliphatic acyl group having up to 18 carbon atoms, it may be, for example, an alkanoyl group (such as formyl, acetyl, propionyl, butyryl, octanoyl, lauroyl, palmitoyl or stearoyl) or an alkenoyl group (such as acryloyl or crotonoyl), preferably an alkanoyl group having from 2 to 4 carbon atoms or an alkenoyl group having 3 or 4 carbon atoms, most preferably an acetyl group.

When X represents a group of formula

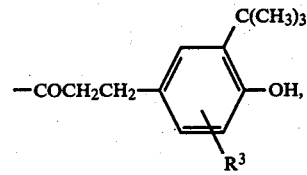

$R_3$ may represent, for example, a methyl, ethyl or t-butyl group, preferably a t-butyl group; and examples of such groups represented by X are 3-(4-hydroxy-3-methyl-5-t-butylphenyl)propionyl and 3-(4-hydroxy-3,5-di-t-butylphenyl)propionyl groups.

When X represents a group of formula:

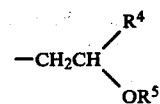

$R^4$ represents a hydrogen atom, a methyl group or a phenyl group (preferably a hydrogen atom) and $R^5$ represents: a hydrogen atom; an alkyl group having from 1 to 18 carbon atoms (e.g. methyl, ethyl, n-butyl or octyl), preferably an alkyl group having from 1 to 4 carbon atoms; an allyl group; a benzyl group; or an aliphatic, aromatic, araliphatic or alicyclic acyl group having up to 18 carbon atoms, in which the aromatic moiety is optionally substituted with a $C_1$–$C_4$ alkyl and/or hydroxy substituent. Where $R^5$ represents such an acyl group, it is preferably a group of formula —COR$^{14}$, in which $R^{14}$ represents: an alkyl group having from 1 to 17 carbon atoms; an alkenyl group having 2 or 3 carbon atoms; a phenyl group which is unsubstituted or has up to 3 substituents, the substituents being the same or different and selected from $C_1$–$C_4$ alkyl groups and hydroxy groups; a benzyl group; a 4-hydroxy-3,5-di-t-butylphenethyl group; a styryl group; or a cyclohexyl group. Examples of such acyl groups are acetyl; propionyl; valeryl; octanoyl; 2-ethylhexanoyl; lauroyl; palmitoyl; stearoyl; acryloyl; crotonoyl; methacryloyl; benzoyl; o-, m- or p-toluoyl; p-t-butylbenzoyl; salicycloyl; 4-hydroxy-3,5-di-t-butylbenzoyl; phenylacetyl; 3-(4-hydroxy-3,5-di-t-butylphenyl)propionyl; cinnamoyl; or cyclohexanecarbonyl. Of the groups of formula —CH₂CH(OR⁵)R⁴, those of formula —CH₂CH₂OR⁵ (in which R⁵ represents a hydrogen atom, an alkanoyl group having from 2 to 18 carbon atoms or a benzoyl group) are most preferred.

When X represents a group of formula —CH₂COOR⁶, R⁶ represents: an alkyl group having from 1 to 18 carbon atoms (e.g. methyl, ethyl, n-butyl, octyl, dodecyl or octadecyl), preferably an alkyl group having from 1 to 4 carbon atoms; an alkenyl group having 3 or 4 carbon atoms (e.g. allyl or 2-butenyl); or a phenyl group.

When b=2 and Y represents a group of formula —CH₂CH(OZ)CH₂—[OCH₂CH(R⁷)]ₘ—OCH₂CH(OZ)CH₂—, m represents an integer from 1 to 10, preferably 1, and R⁷ represents a hydrogen atom or a methyl group, preferably a hydrogen atom.

When Y represents a group of formula —CH₂CH(OZ)CH₂—[OWO—CH₂CH(OZ)CH₂]ₙ—, n represents an integer from 1 to 10, preferably from 1 to 3 and most preferably 1. In this formula, when W represents a group of formula:

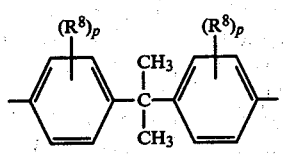

p may be 0, in which case the benzene rings are unsubstituted, or p may be 1 or 2, in which case R⁸ represents a halogen atom, e.g. chlorine or bromine. Examples of such groups are

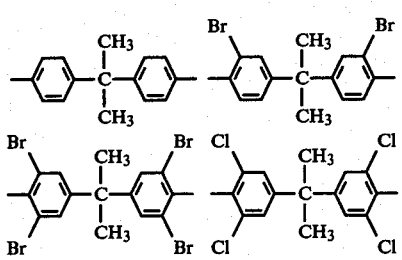

We particularly prefer the group represented by this formula when p=0.

When W represents a group of formula —CO—(CH₂)q—CO—, q represents an integer from 1 to 10, preferably from 2 to 8 and most preferably 4, and examples of such groups are malonyl, succinyl, adipoyl, suberoyl, sebacoyl and dodecandioyl.

Other groups which may be represented by W are phthaloyl, isophthaloyl, terephthaloyl, and 1,2-, 1,3- or 1,4-cyclohexanedioyl groups, preferably phthaloyl or 1,2-cyclohexanedioyl.

When Z represents an alkyl group having from 1 to 18 carbon atoms, it may be, for example, a methyl, ethyl, n-propyl, n-butyl, octyl, dodecyl or octadecyl group, preferably an alkyl group having from 1 to 8 carbon atoms, and most preferably a methyl group.

When Z represents an aliphatic, aromatic, araliphatic or alicyclic acyl group having up to 18 carbon atoms (in which the aryl moiety may optionally be substituted), it is preferably a group of formula —COR¹⁴, in which R¹⁴ is as defined above. Preferred examples of such groups are those previously exemplified for R⁵ where R⁵ represents a group of formula —COR¹⁴. Of the acyl groups, the most preferred are alkanoyl groups having from 2 to 18, particularly from 2 to 12, carbon atoms or a benzoyl group. We particularly prefer that, where the substituent Z represents an acyl group of formula —COR¹⁴, it should be identical with the aliphatic acyl group represented by the substituent X or with the acyl group —COR¹⁴ represented by the group R⁵.

When Z represents a group of formula —CONR⁹R¹⁰, R⁹ may represent a hydrogen atom or an alkyl group having from 1 to 4 carbon atoms (e.g. methyl, ethyl or n-butyl), preferably a hydrogen atom; R¹⁰ may represent: an alkyl group having from 1 to 18 carbon atoms, e.g. methyl, ethyl, n-butyl, octyl or octadecyl; a phenyl group which may optionally have one or more methyl, chlorine or bromine substituents, e.g. phenyl, o-tolyl, m-tolyl, p-tolyl, o-chlorophenyl, m-chlorophenyl, p-chlorophenyl, o-bromophenyl, m-bromophenyl or p-bromophenyl; an α- or β-naphthyl group; or a cyclohexyl group. Of the groups of formula —CONR⁹R¹⁰ represented by Z, we prefer groups of formula —CONHR¹⁰, in which R¹⁰ represents an alkyl group having from 1 to 4 carbon atoms or a phenyl group.

When Z represents a group of formula:

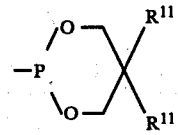

R¹¹ represents a hydrogen atom or an alkyl group having from 1 to 4 carbon atoms, e.g. methyl, ethyl or n-propyl, preferably a methyl group.

When Z represents a group of formula —P(OR¹²)₂, R¹² represents an alkyl group having from 1 to 4 carbon atoms (e.g. methyl, ethyl or isopropyl), a phenyl group or a group of formula:

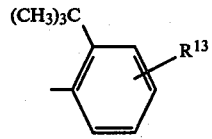

in which R¹³ represents a hydrogen atom or an alkyl group having from 1 to 4 carbon atoms, e.g. methyl, ethyl or t-butyl. Examples of such groups represented by Z are —P(OC₂H₅)₂,

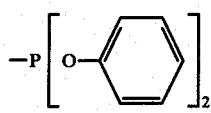

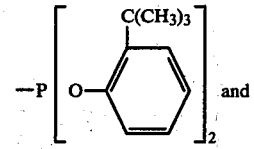 and

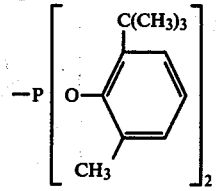

Of the hydantoin derivatives of formula (I), the following classes of compound are particularly preferred:

the class wherein $R^1$ represents a hydrogen atom;

the class wherein $R^2$ represents a hydrogen atom or an acetyl group, particularly a hydrogen atom;

the class wherein X represents a hydrogen atom, a methyl group, an acetyl group or a group of formula —$CH_2CH_2OR^{18}$ (in which $R^{18}$ represents a hydrogen atom, an alkanoyl group having from 2 to 18 carbon atoms or a benzoyl group), particularly a hydrogen atom or a methyl group;

the class of compounds wherein Y represents a group of formula —$CH_2CH(OZ)CH_2$—$OCH_2CH_2$—$OCH_2CH(OZ)CH_2$— or a group of formula —$CH_2CH(OZ)CH_2$—$[OWOCH_2CH(OZ)CH_2]_r$— (in which W and Z are as defined above and r is 0 or 1), particularly those compounds in which r is 1 and W represents a group of formula

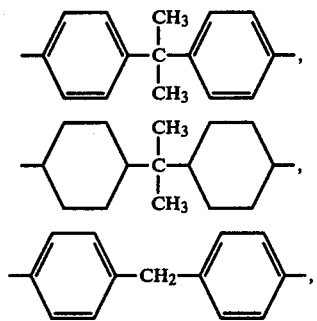

or —$CO(CH_2)_qCO$— (in which q is as defined above); and the class of compounds in which Z represents a hydrogen atom: an alkanoyl group having from 2 to 18 carbon atoms or a benzoyl group.

When $R^1$ represents a methyl group, the hydantoin derivatives of formula (I) exist in the form of a number of stereoisomers and the compounds of the invention may be provided both in the form of the individual stereoisomers and in the form of various mixtures thereof.

The invention also provides acid addition salts of the hydantoin derivatives of formula (I). The nature of the acid employed to form such acid addition salts is not critical, provided that, where the acid addition salt is to be used to stabilize a synthetic polymer, the acid employed does not adversely affect the stability of the polymer. Examples of suitable acids include: inorganic acids, such as sulphuric acid, hydrochloric acid and phosphoric acid; organic carboxylic acids, such as formic acid, acetic acid, valeric acid, stearic acid, oxalic acid, adipic acid, sebacic acid, maleic acid, benzoic acid, p-t-butylbenzoic acid, 4-hydroxy-3,5-di-t-butylbenzoic acid, salicylic acid and terephthalic acid; sulfonic acids, such as methanesulphonic acid and p-toluenesulphonic acid; and organic phosphonic acids, such as phenylphosphonic acid.

The following is a non-limiting list of individual hydantoin derivatives of formula (I). The numbers appended to the compounds in this list will be used to identify them hereinafter in the Examples. In these formulae, the abbreviation t-Bu is used to represent the t-butyl group.

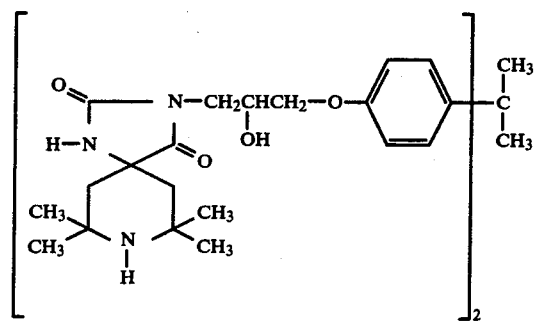

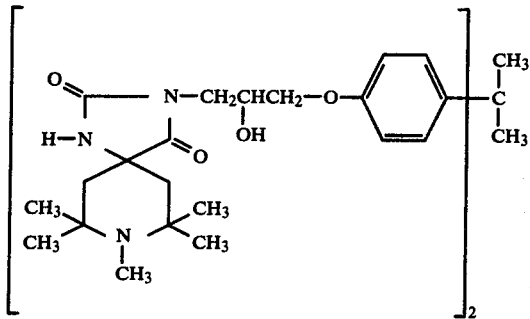

3.
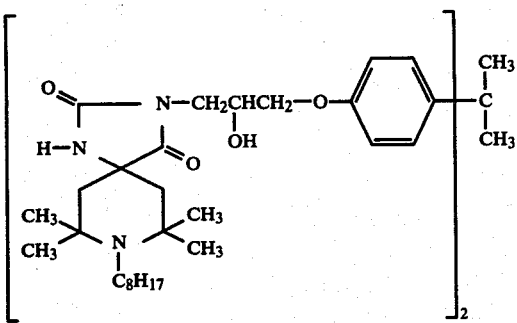
4.
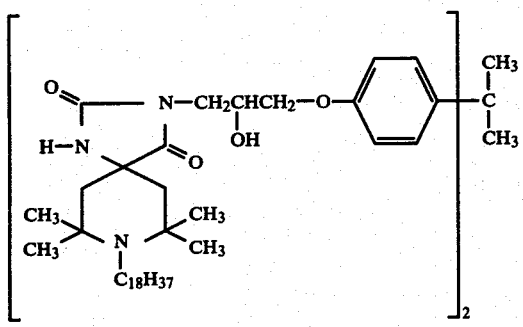
5.
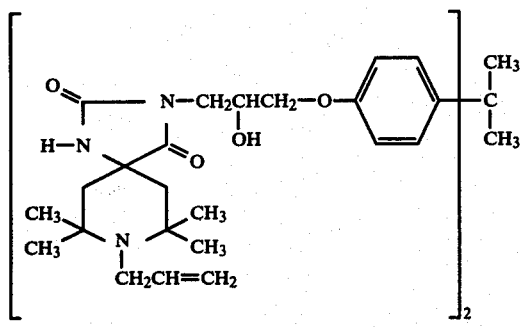
6.
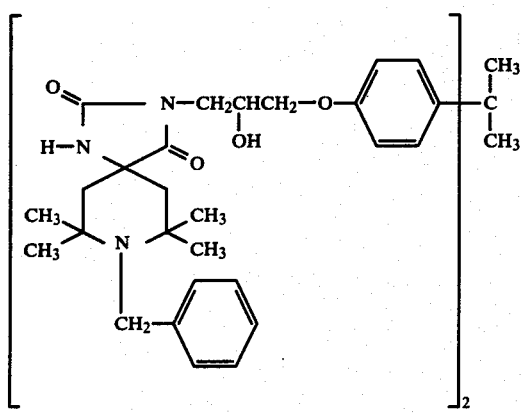

7.
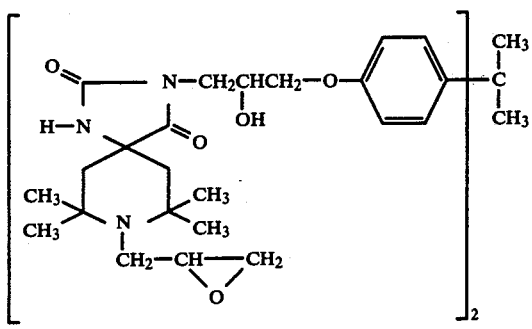
8.
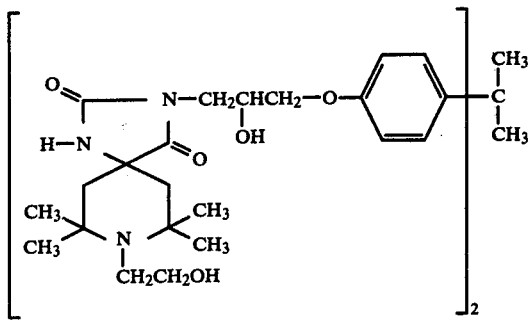
9.
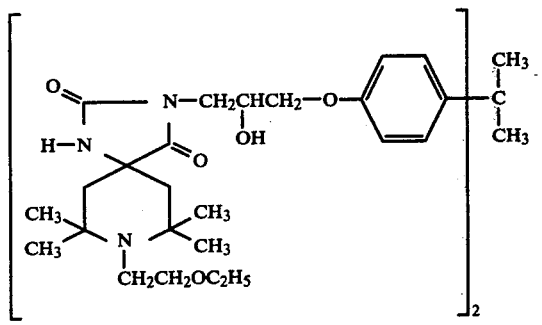
10.
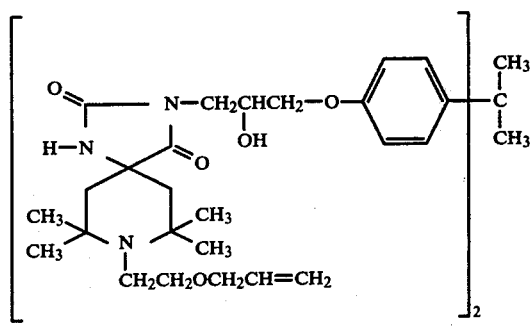
11.
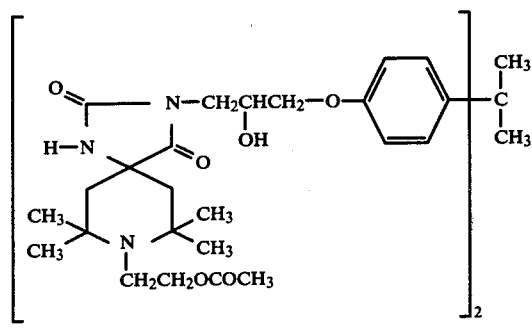

-continued
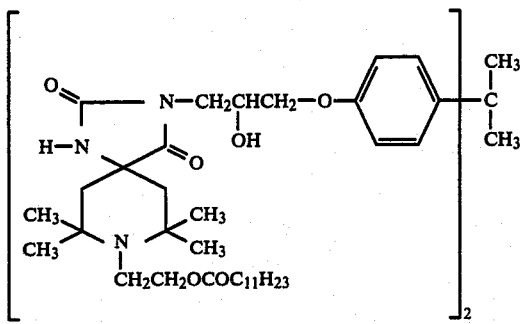
12.
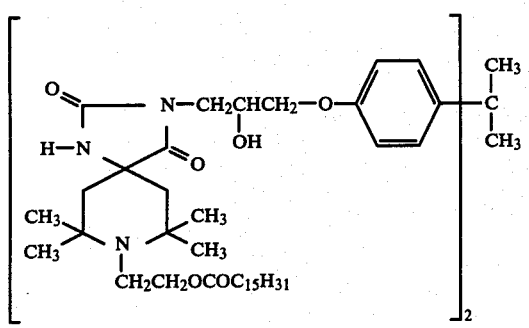
13.
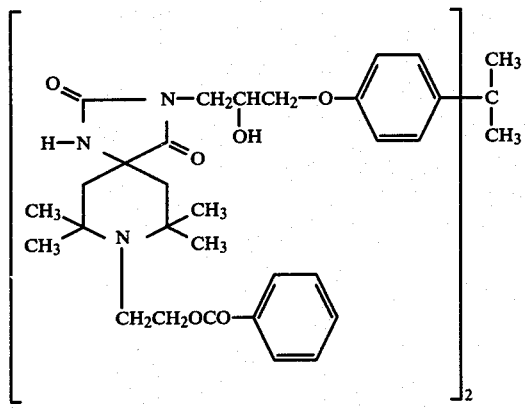
14.
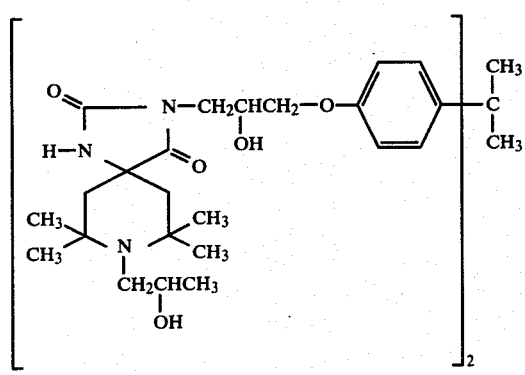
15.

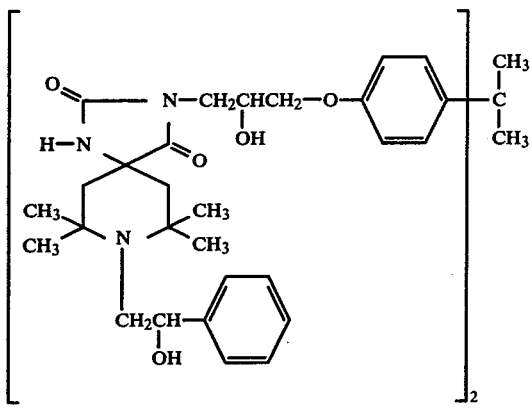
16.
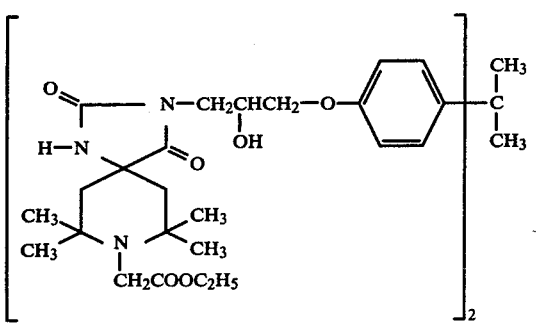
17.
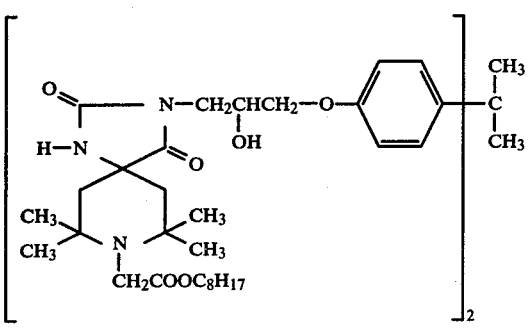
18.
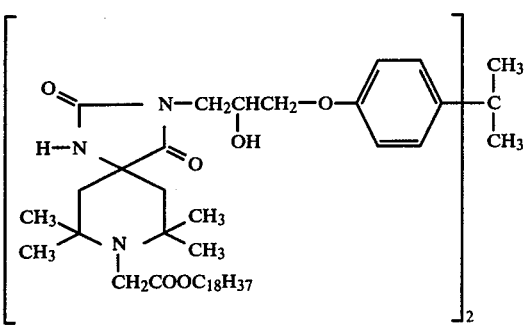
19.

-continued
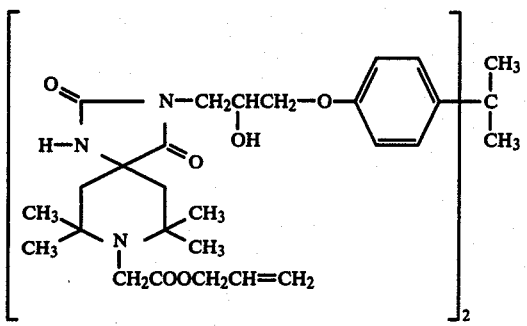
20.
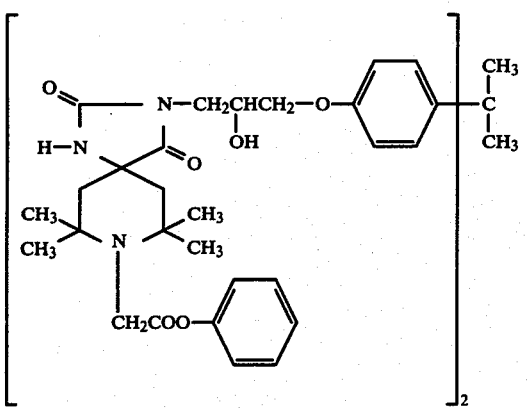
21.
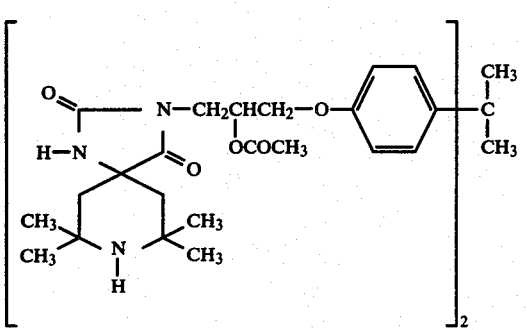
22.
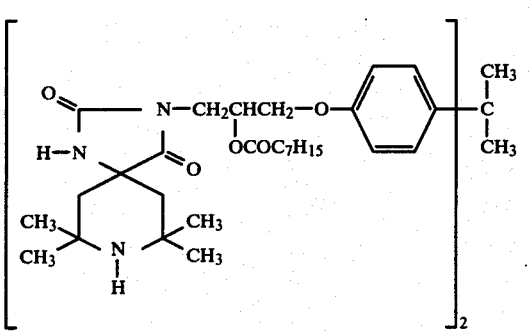
23.

24.
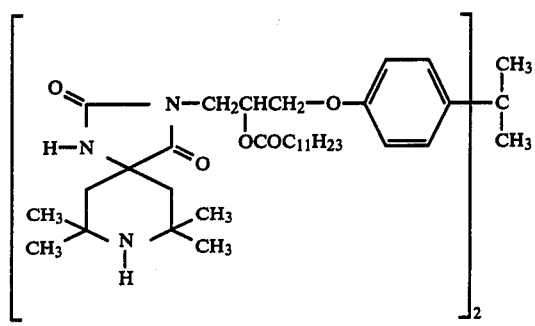
25.
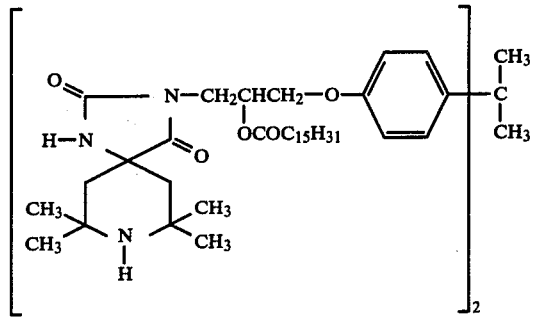
26.
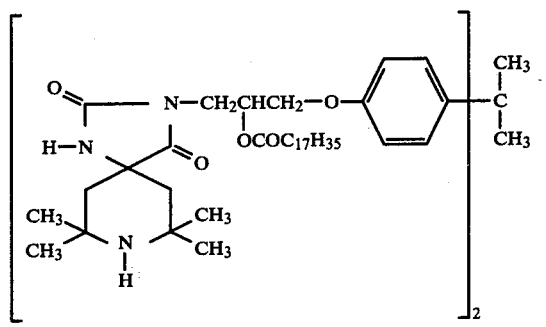
27.
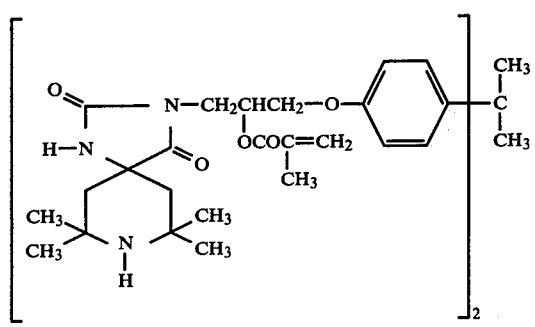
28.
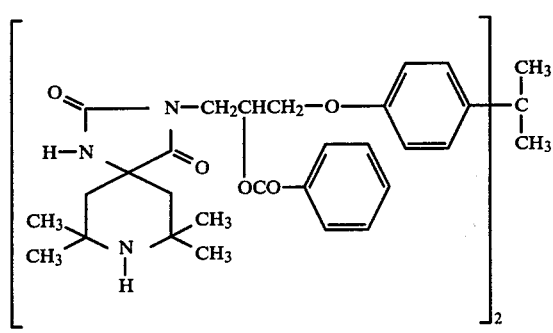

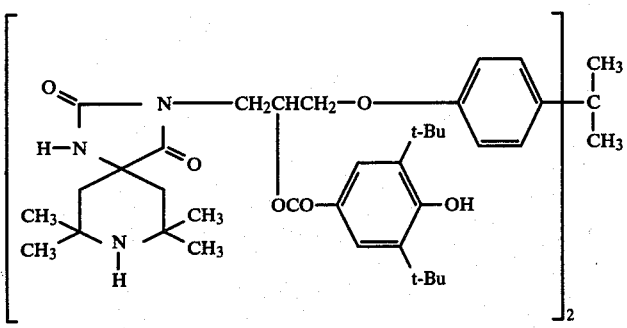
29.
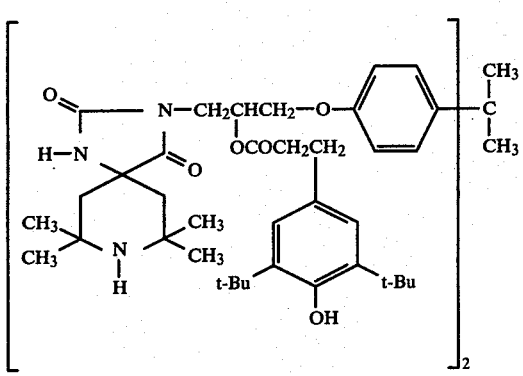
30.
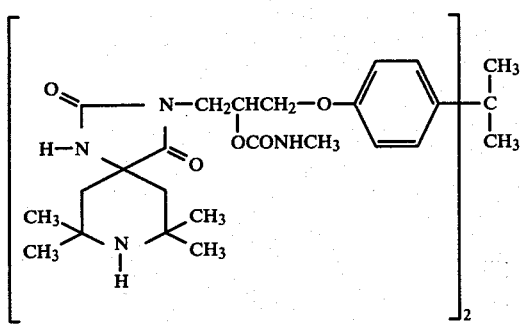
31.
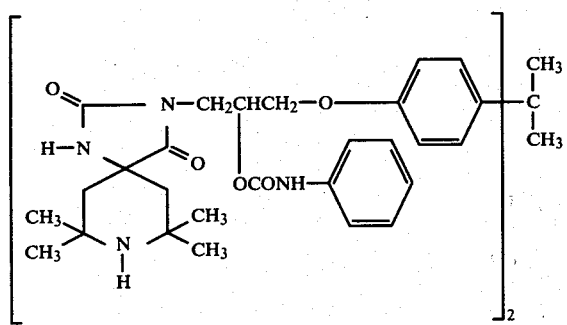
32.

33.
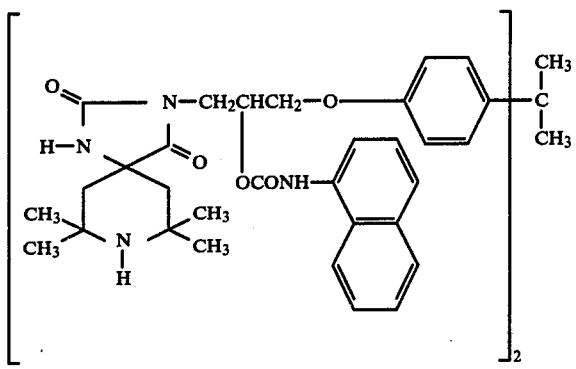
34.
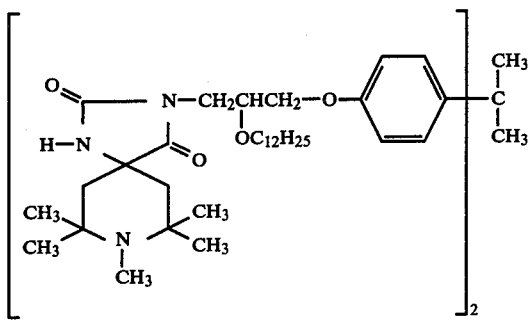
35.
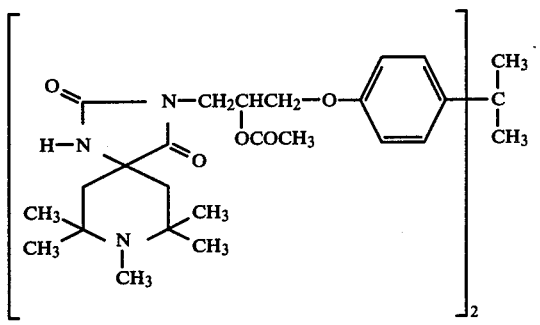
36.
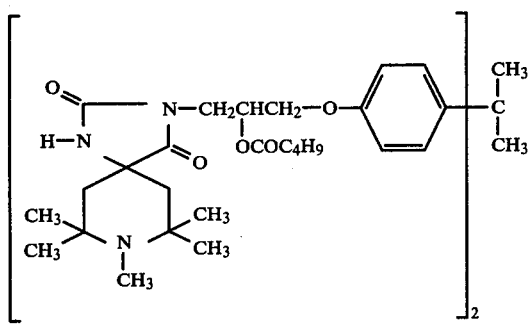
37.
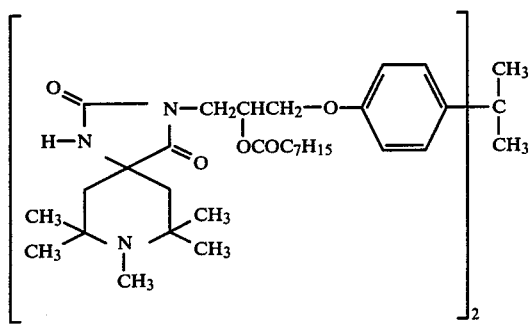

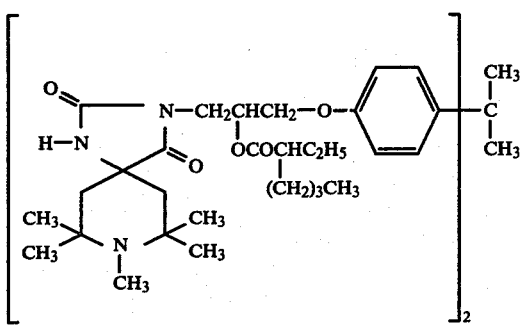
38.
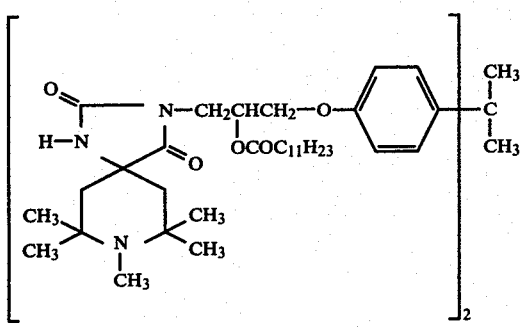
39.
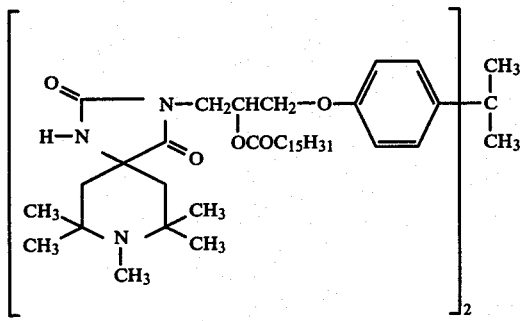
40.
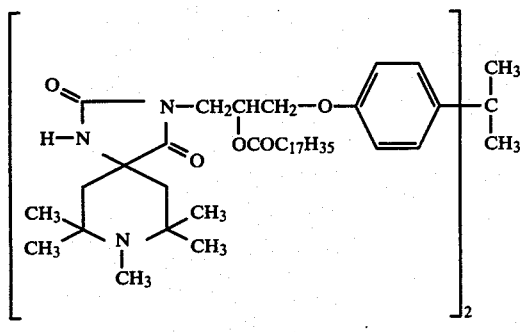
41.
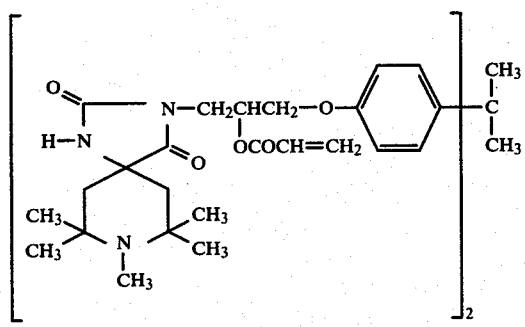
42.

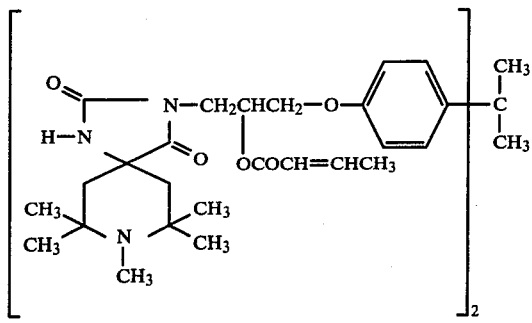 43.
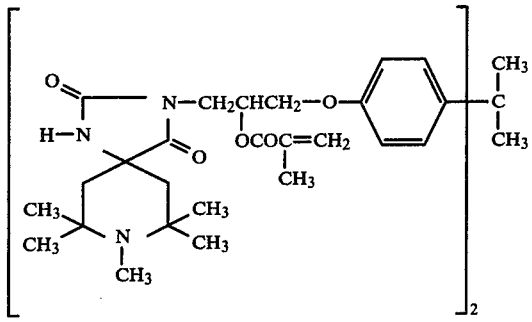 44.
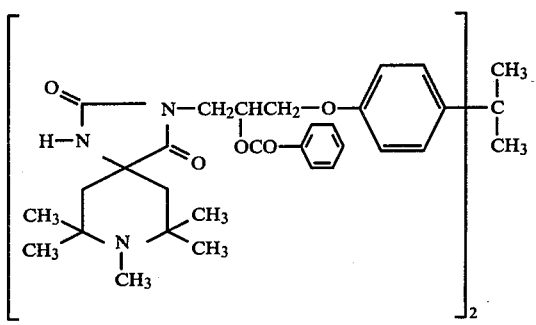 45.
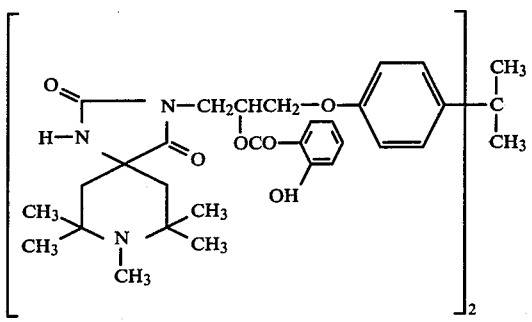 46.
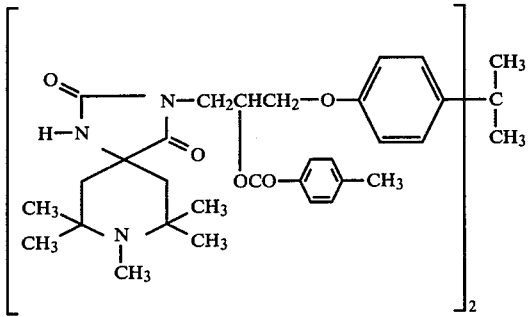 47.

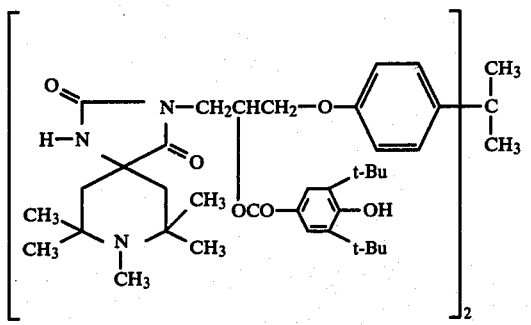
48.
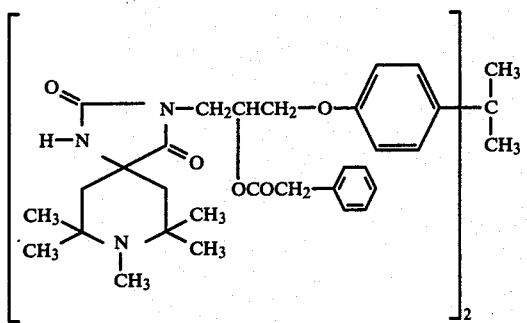
49.
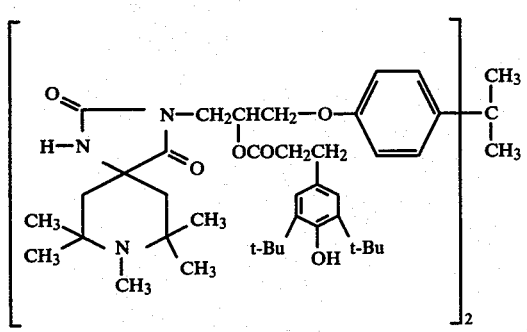
50.
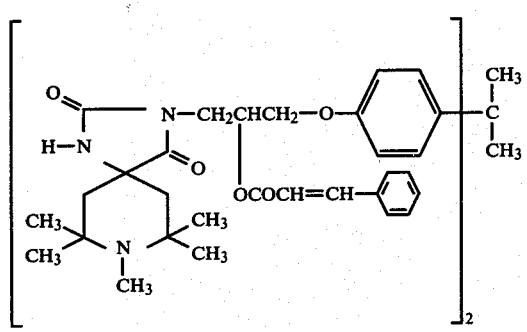
51.
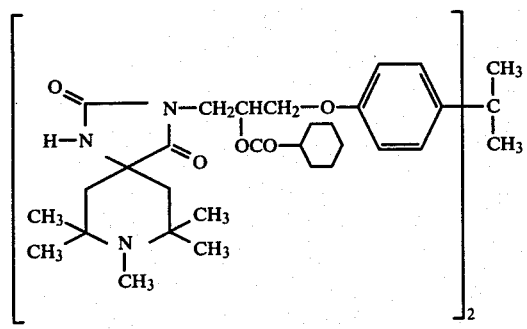
52.

53.
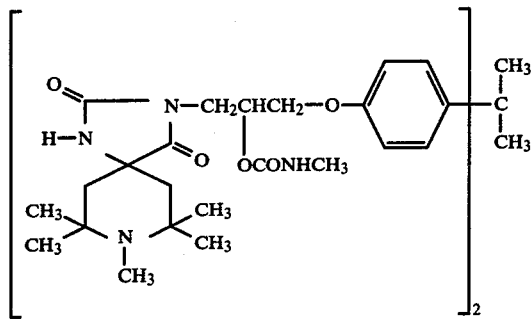
54.
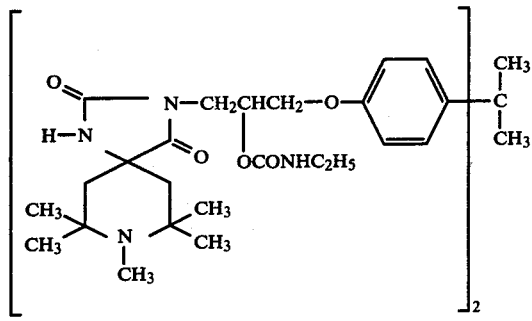
55.
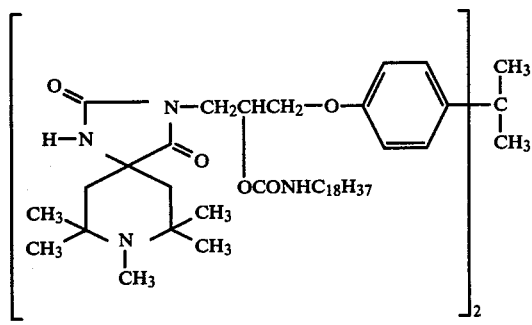
56.
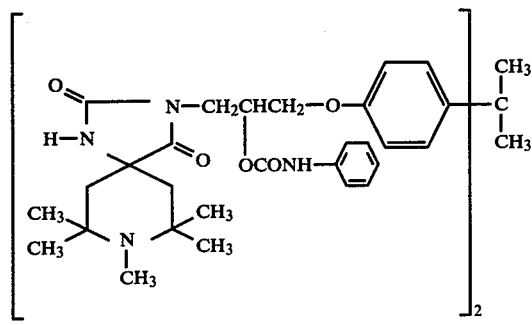
57.
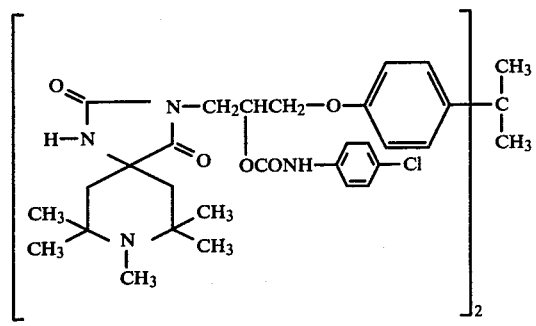

58.
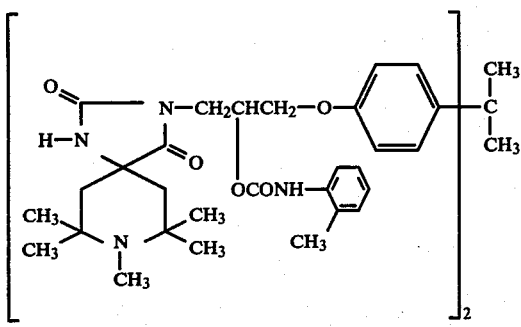
59.
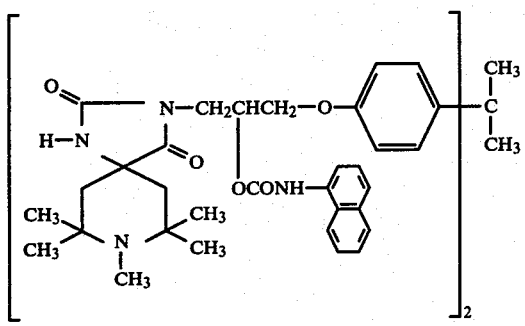
60.
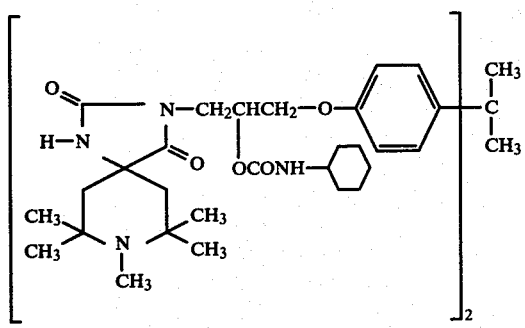
61.
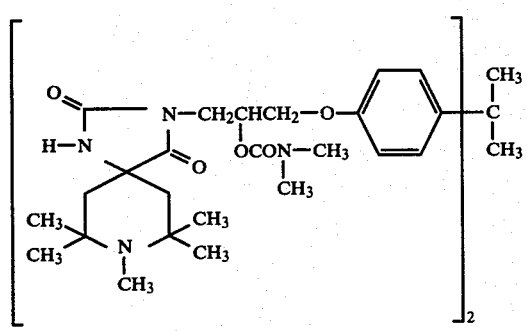
62.
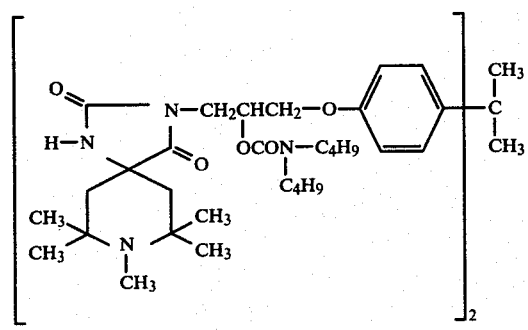

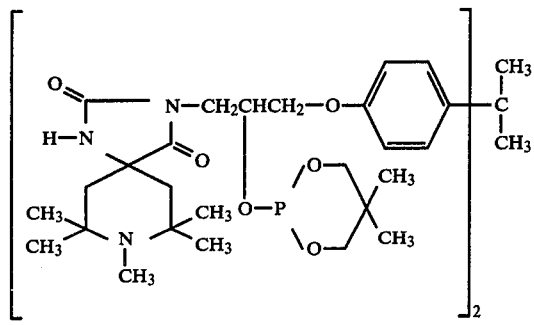
63.
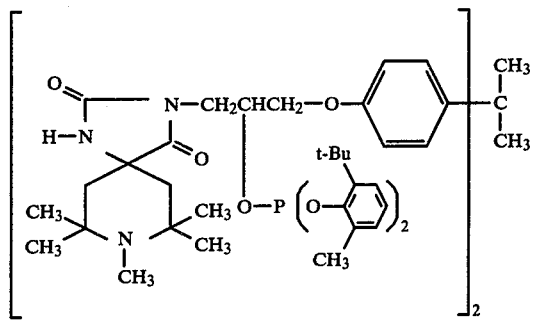
64.
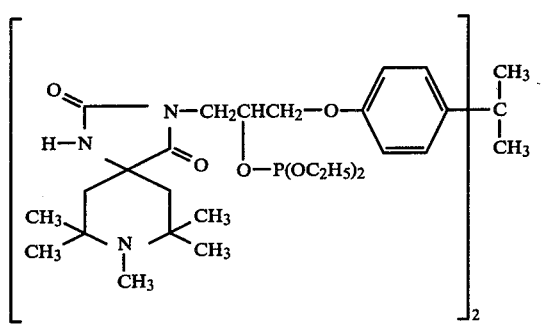
65.
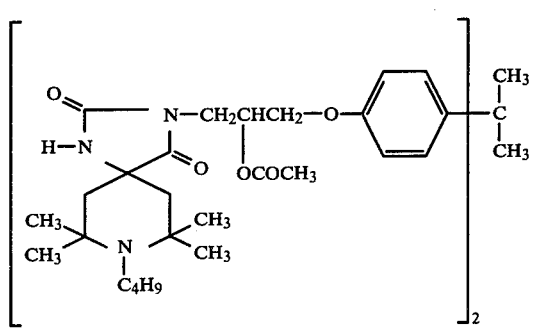
66.
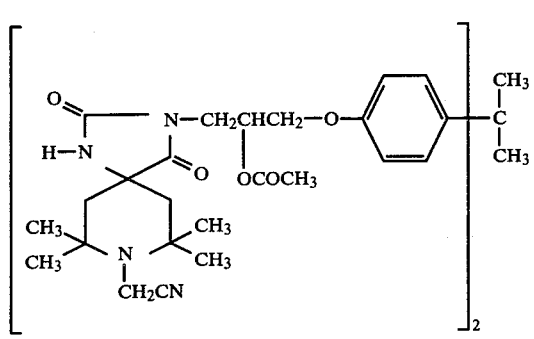
67.

-continued
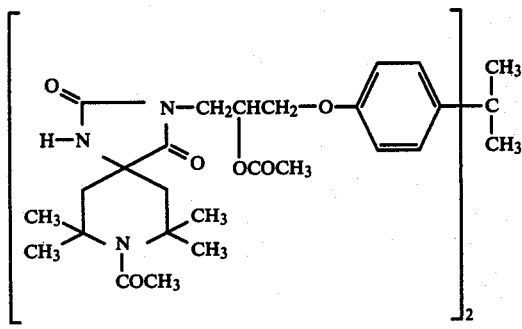
68.
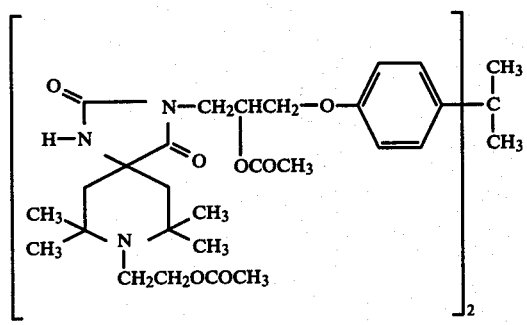
69.
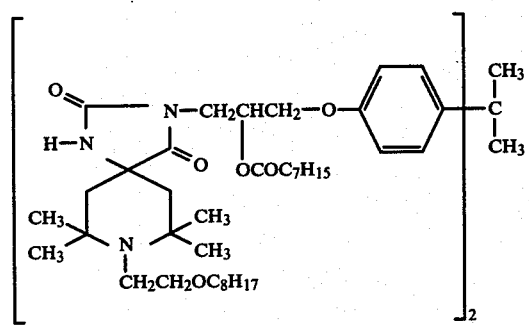
70.
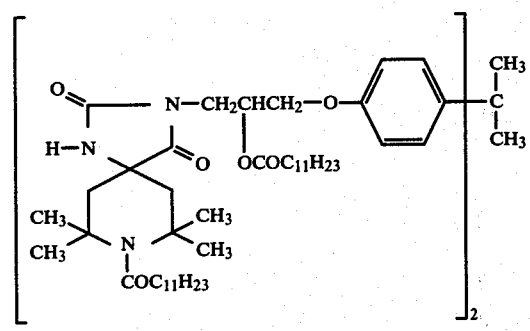
71.
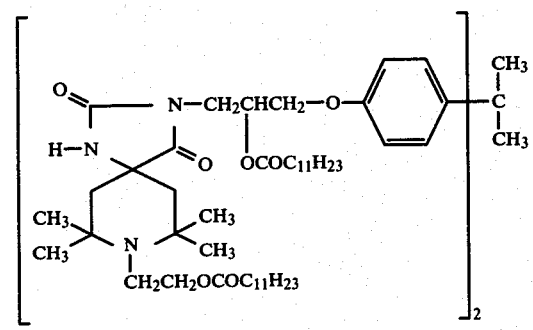
72.

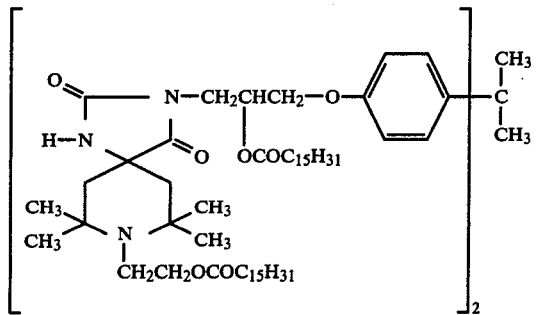
73.
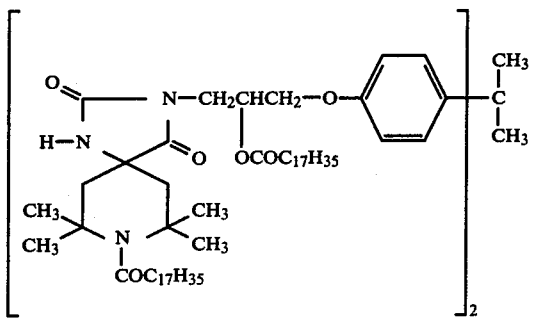
74.
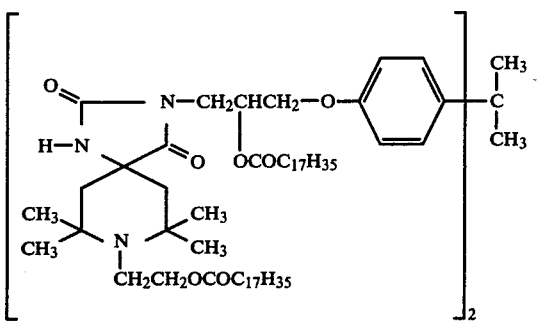
75.
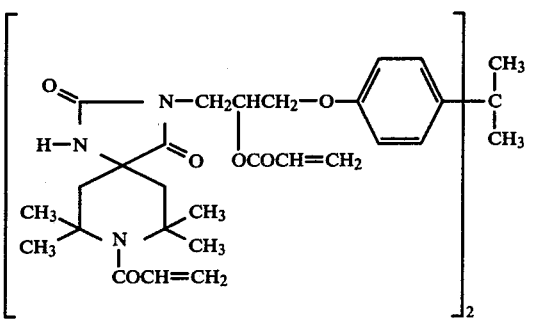
76.
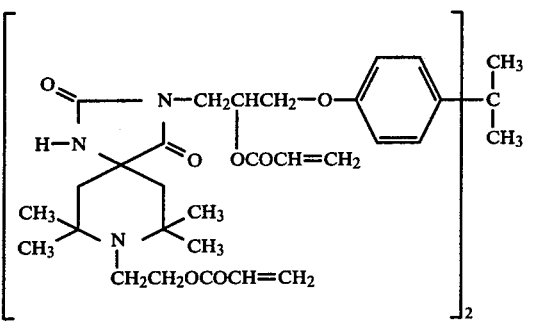
77.

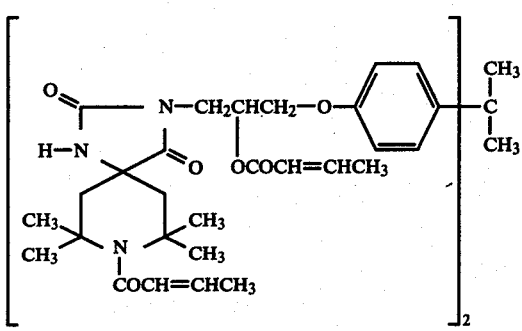
78.
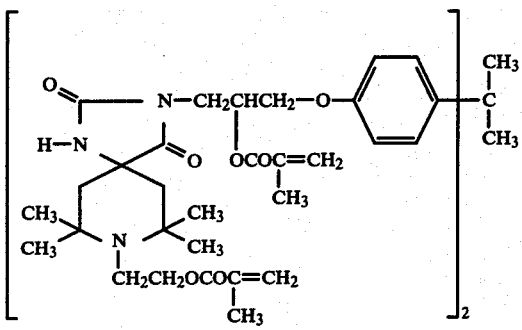
79.
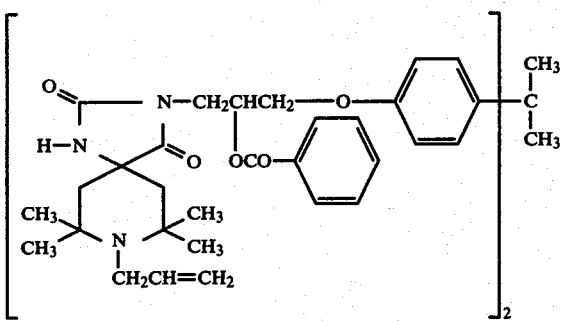
80.
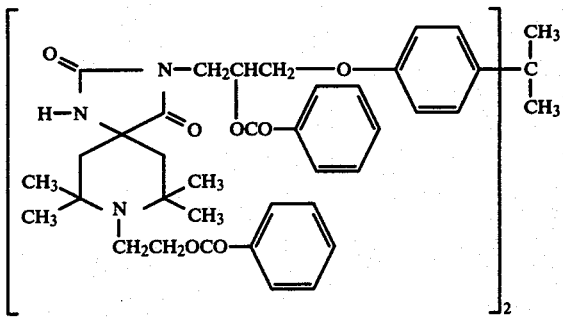
81.
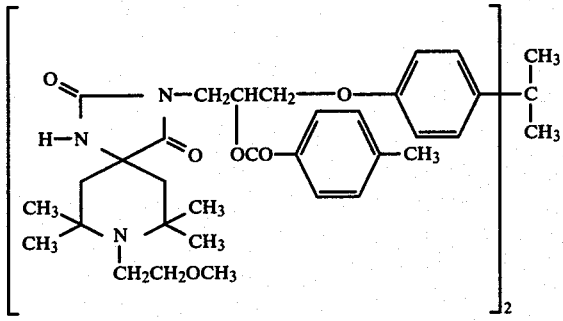
82.

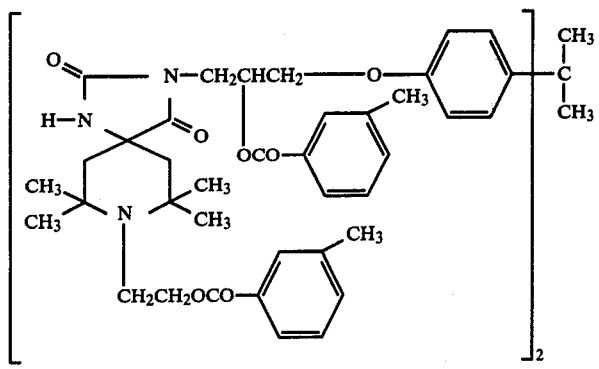
83.
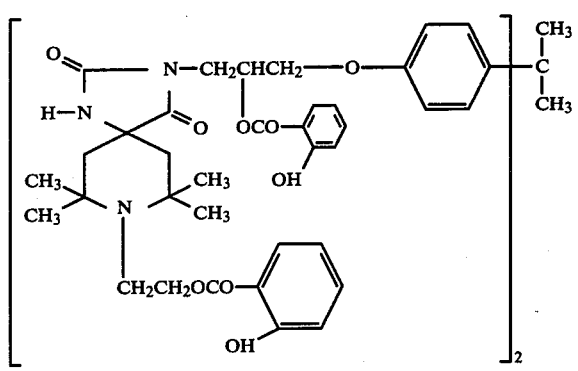
84.
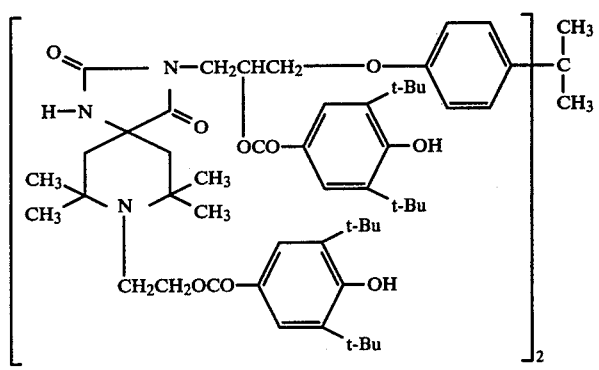
85.
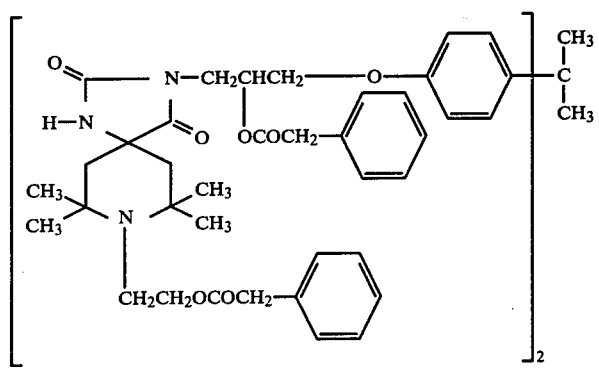
86.

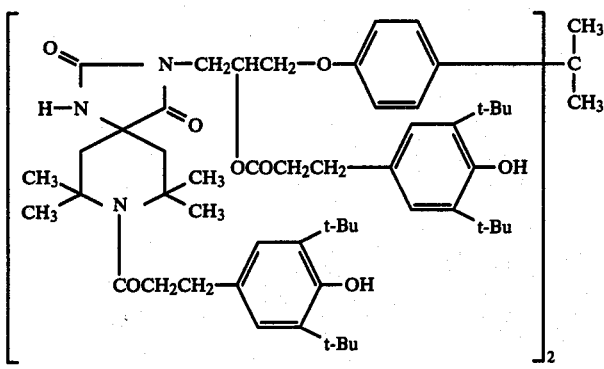
87.
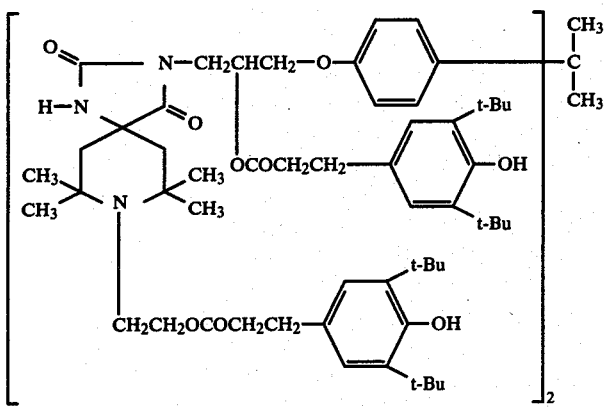
88.
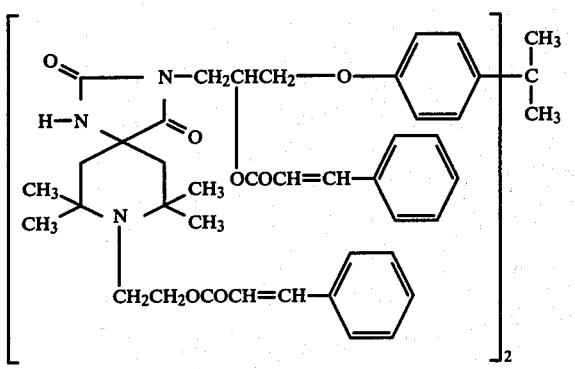
89.
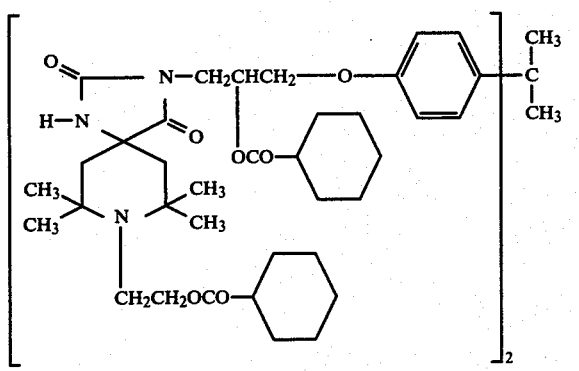
90.

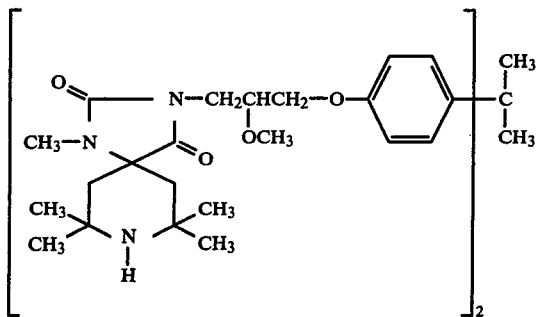 91.
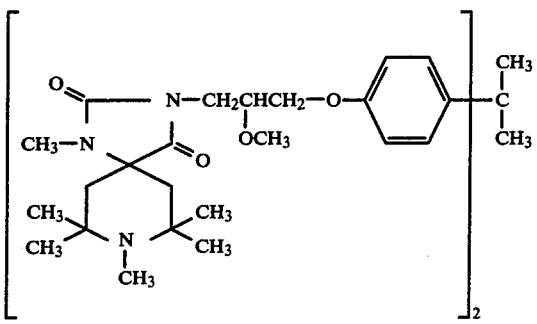 92.
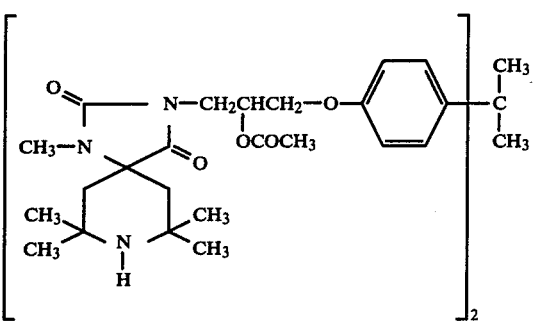 93.
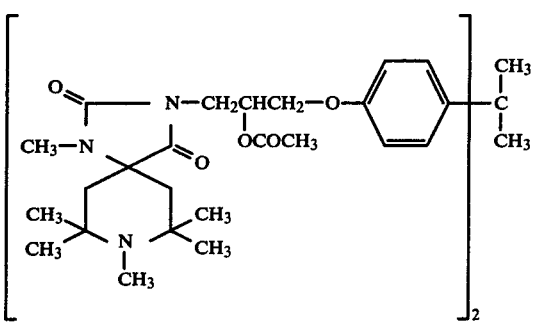 94.
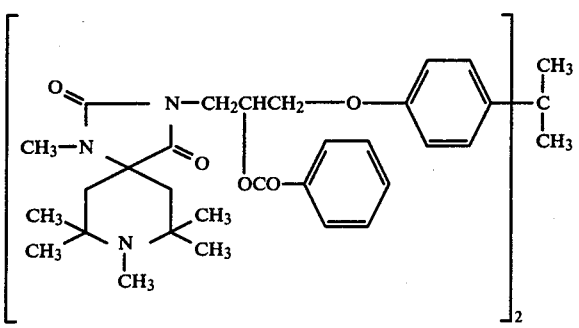 95.

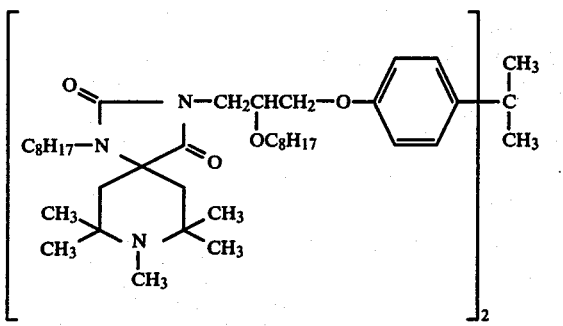
96.
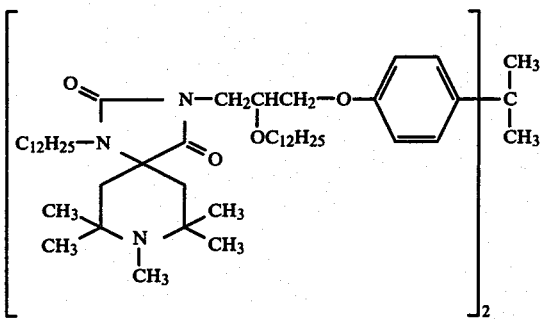
97.
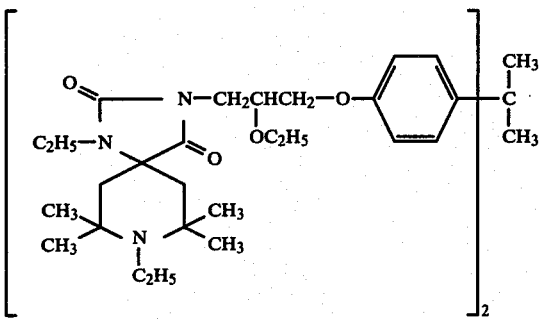
98.
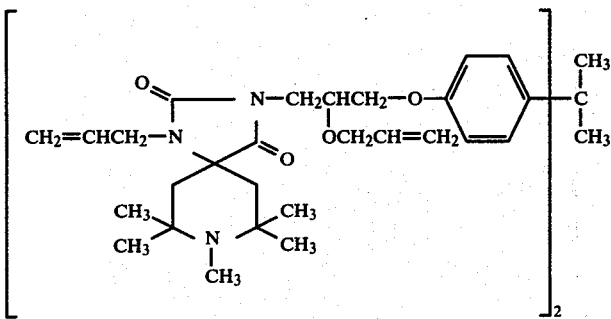
99.

-continued
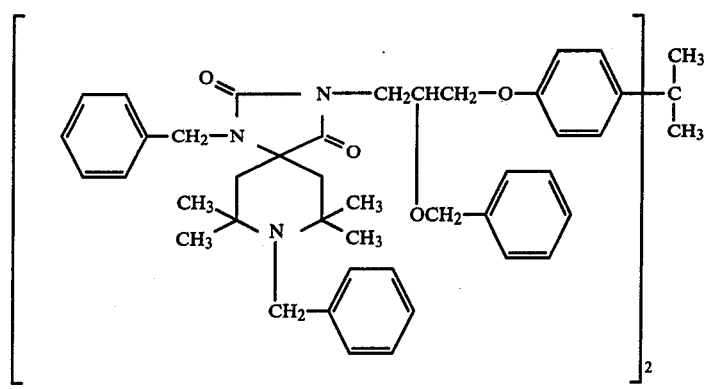
100.
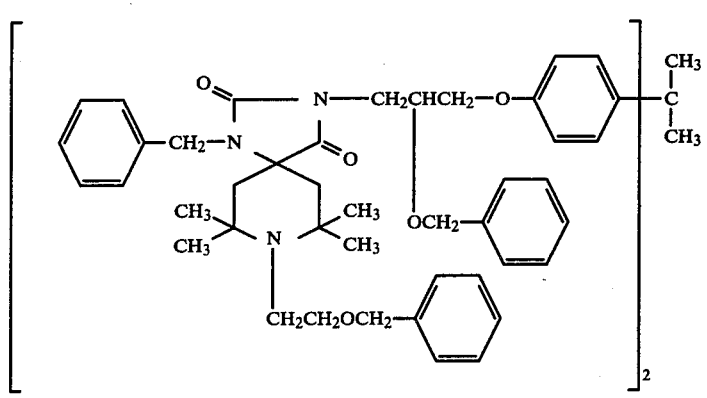
101.
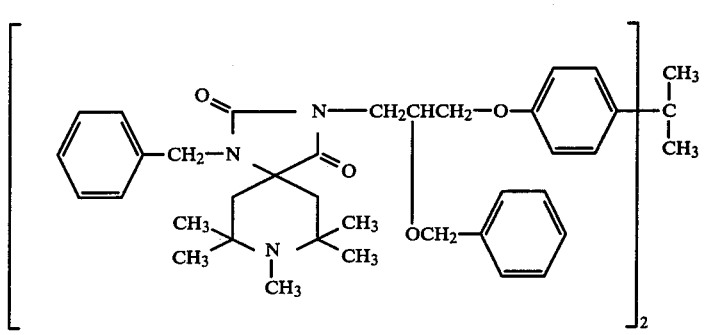
102.
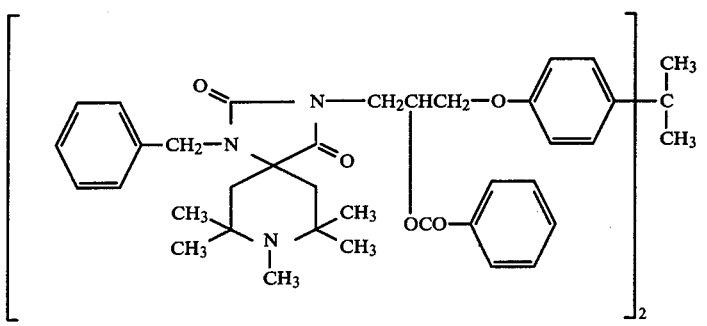
103.

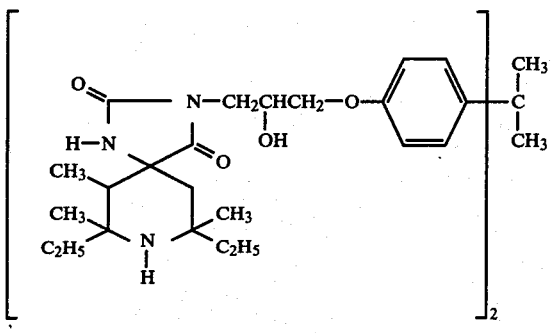
104.
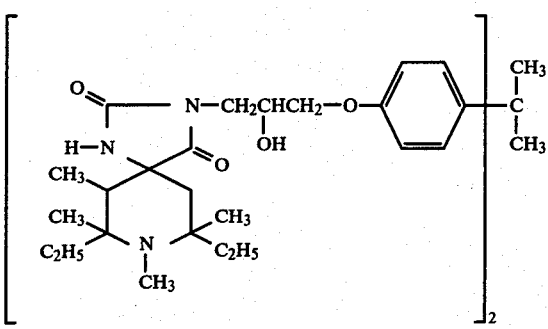
105.
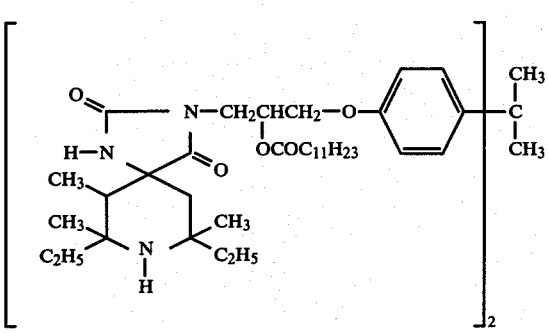
106.
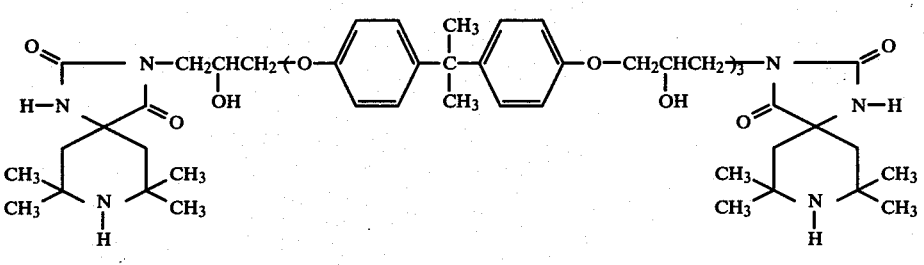
107.
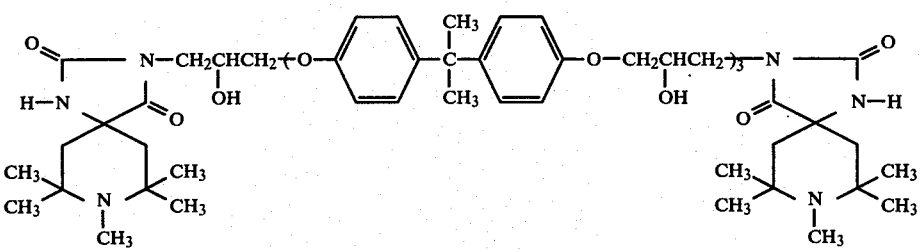
108.

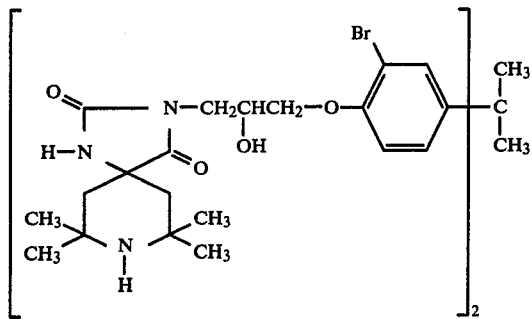
109.
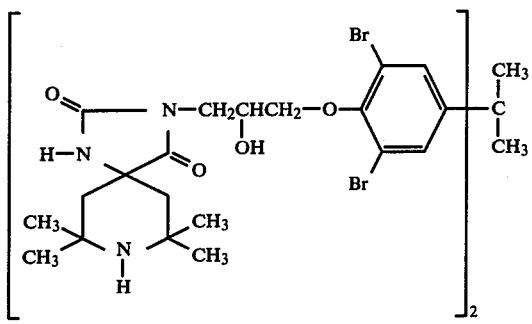
110.
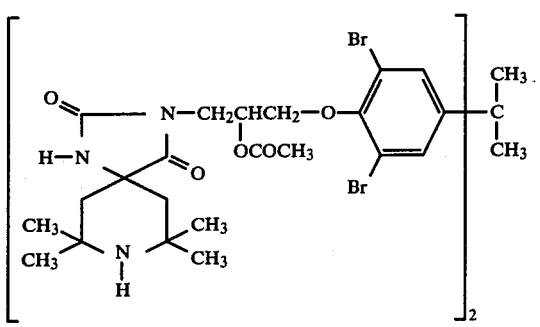
111.
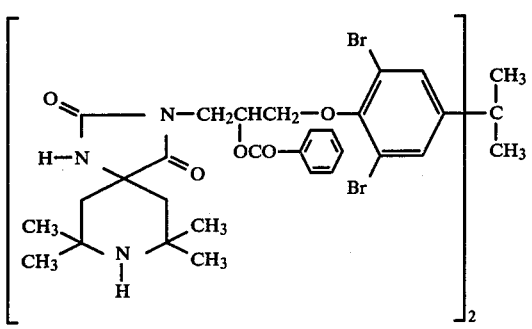
112.
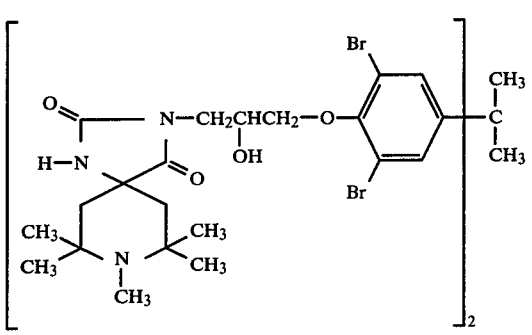
113.

114.
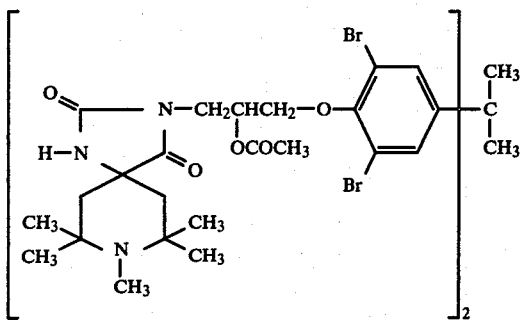
115.
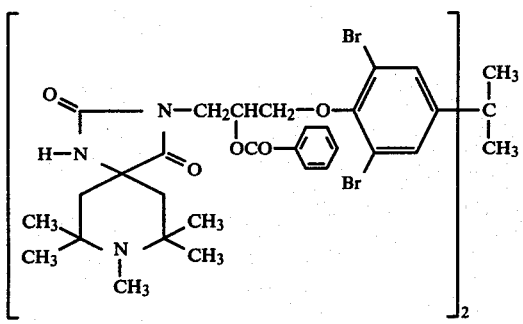
116.
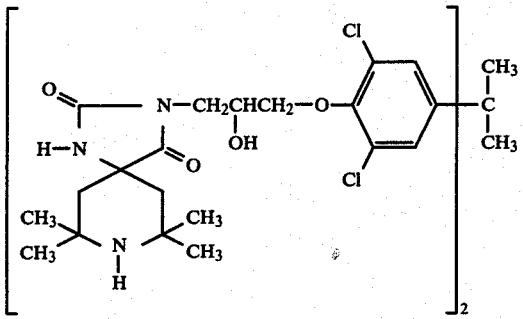
117.
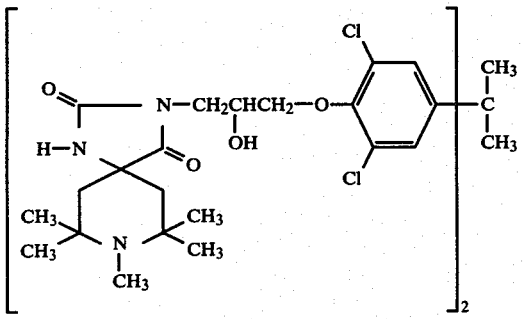
118.
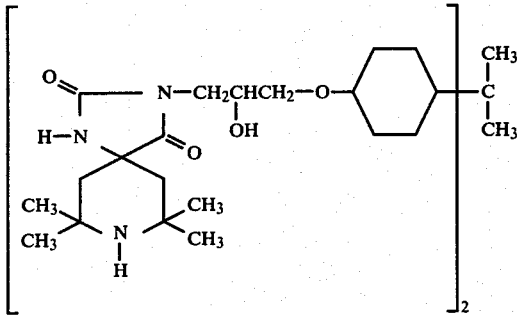

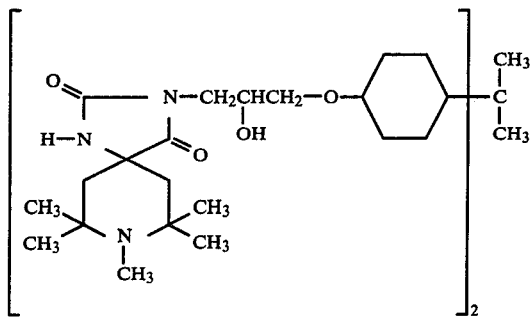 119.
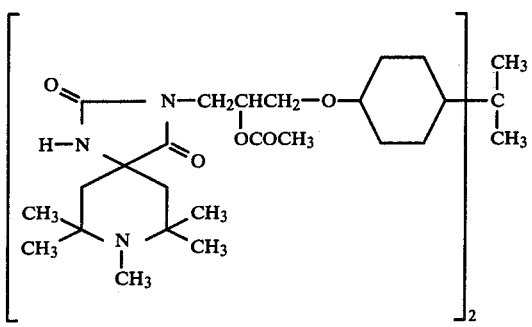 120.
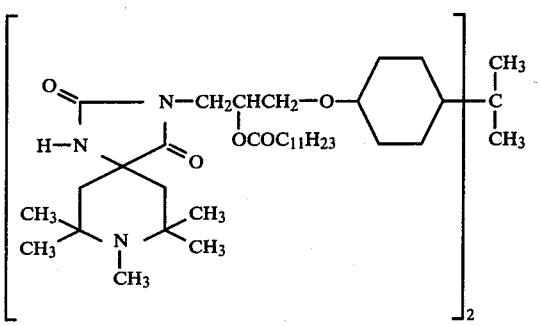 121.
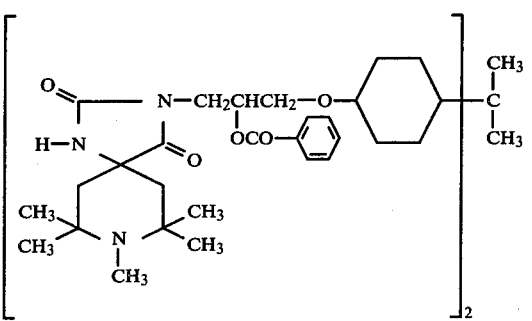 122.
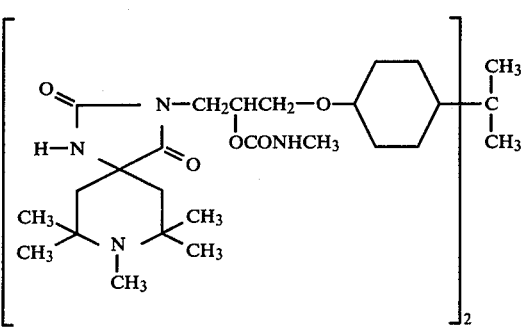 123.

-continued
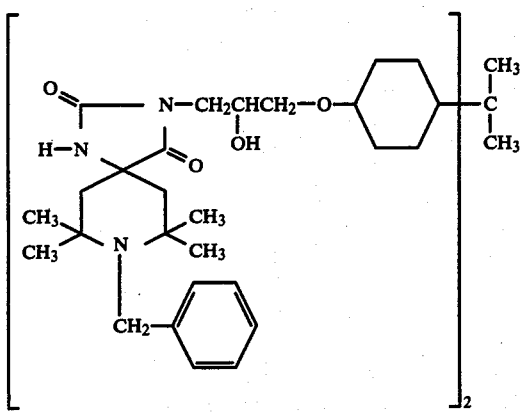
124.
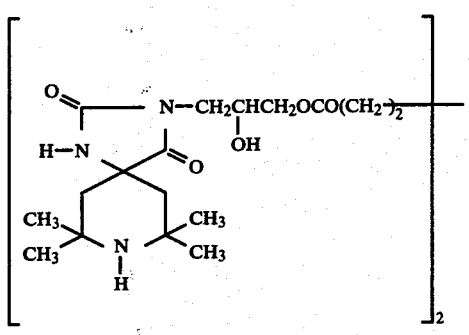
125.
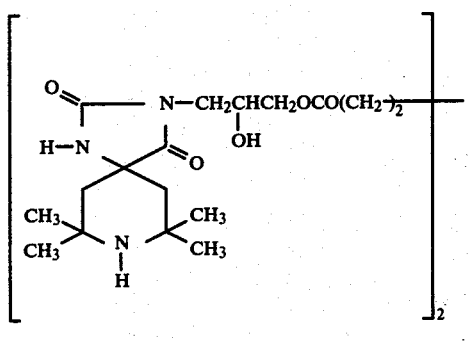
126.
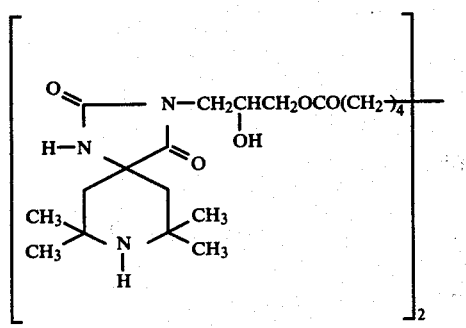
127.

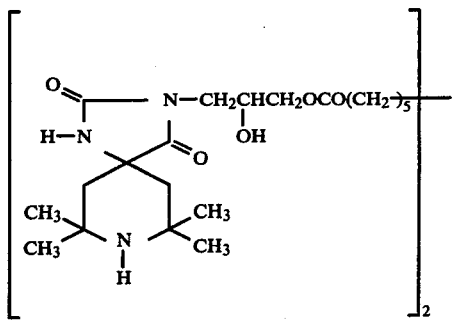
128.
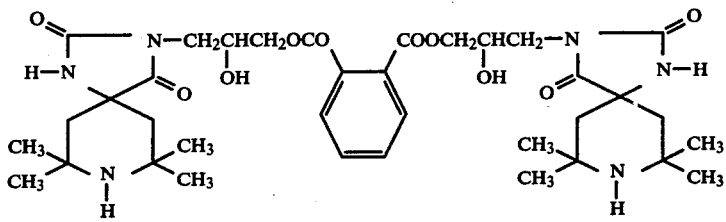
129.
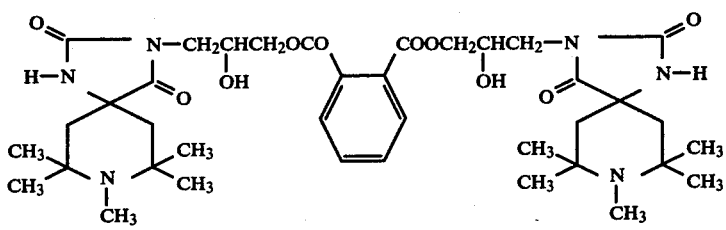
130.
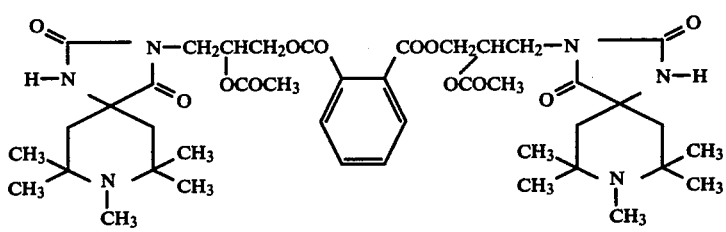
131.
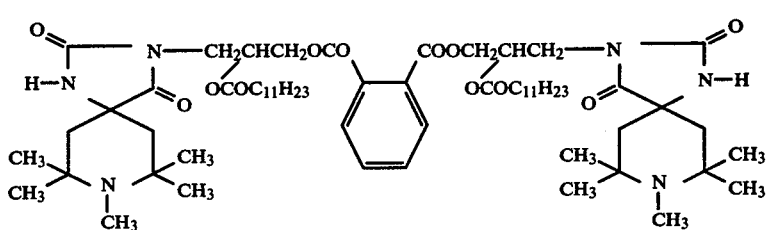
132.
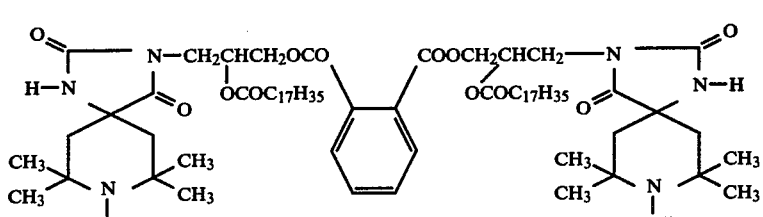
133.
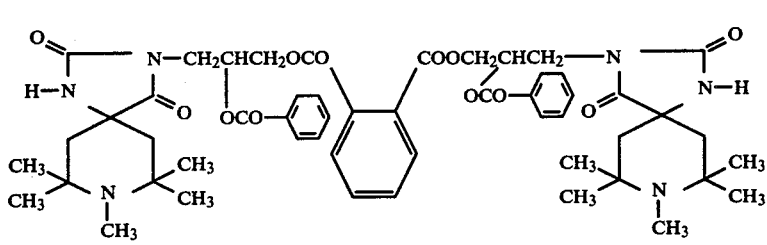
134.

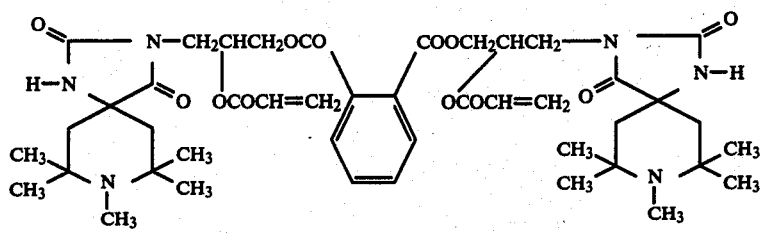
135.
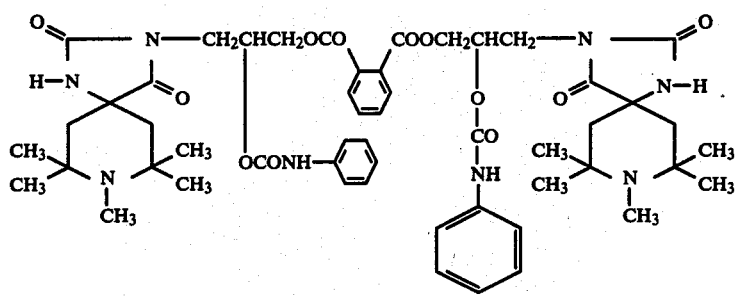
136.
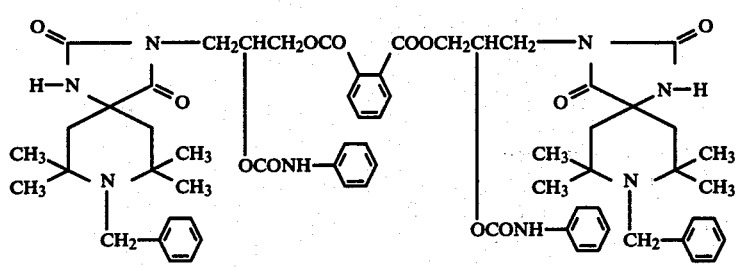
137.
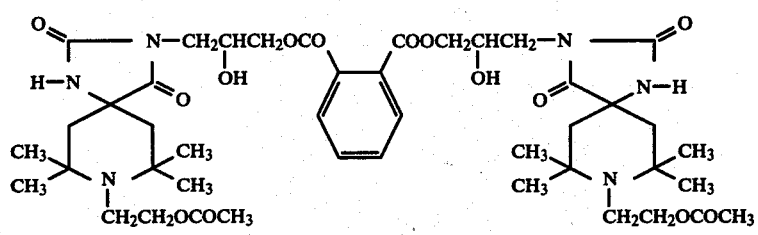
138.
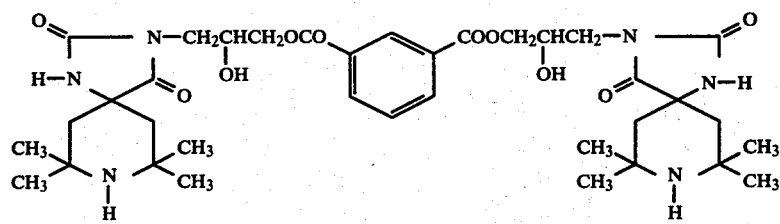
139.
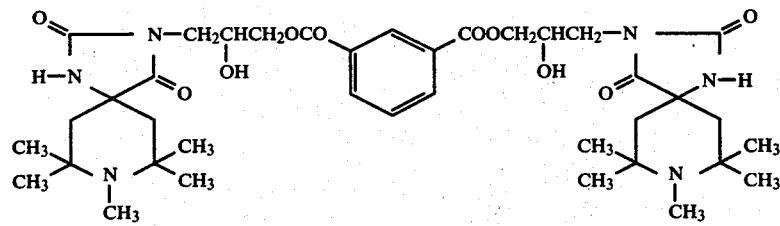
140.

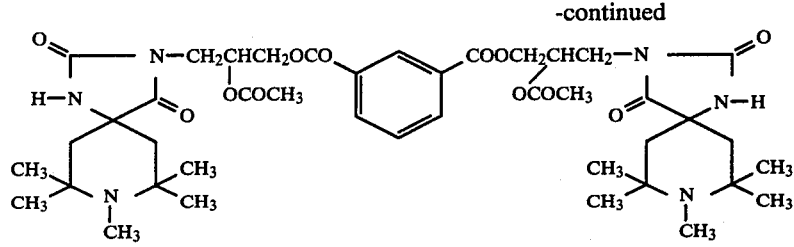 141.
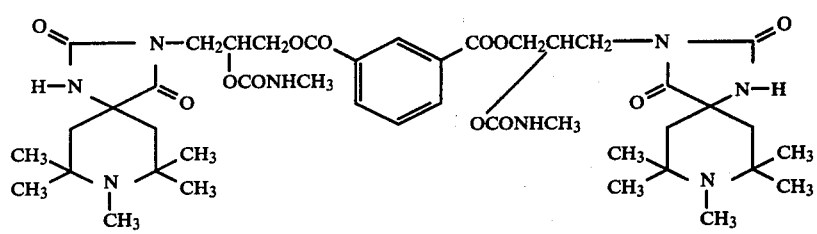 142.
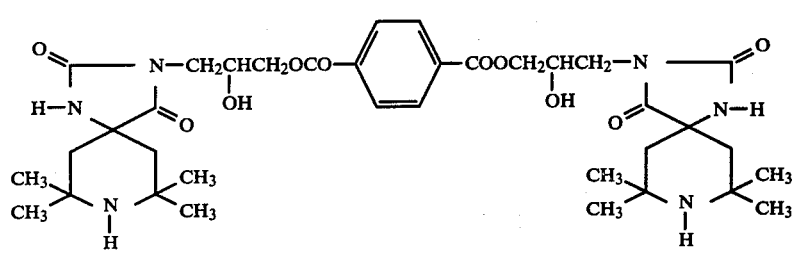 143.
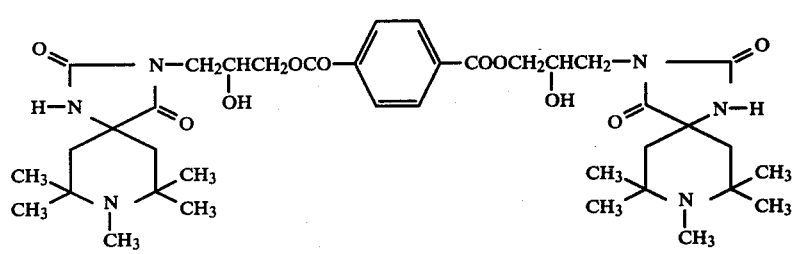 144.
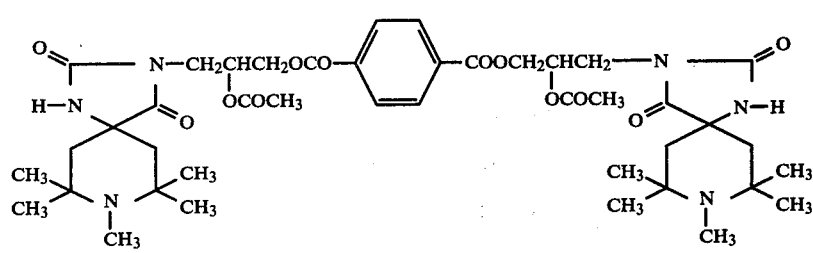 145.
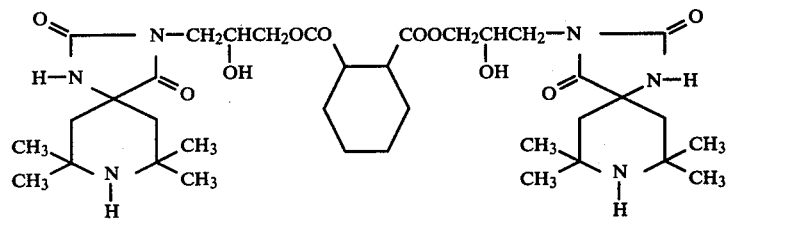 146.
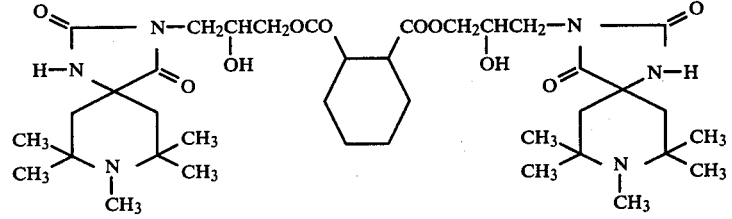 147.

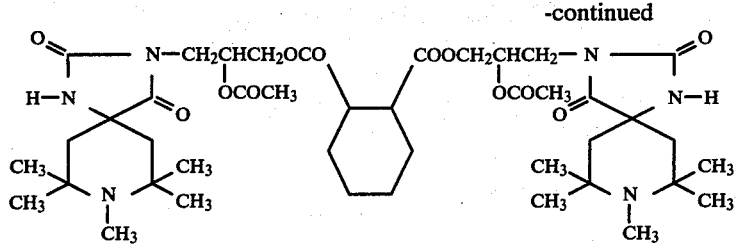
148.
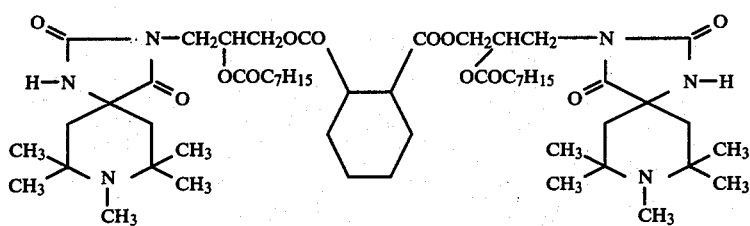
149.
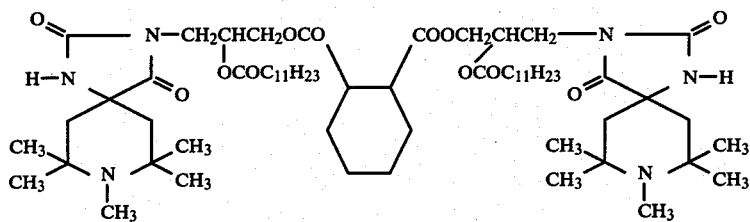
150.
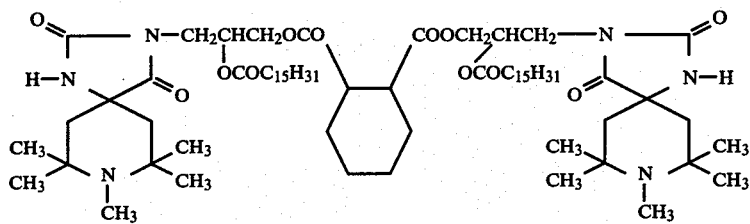
151.
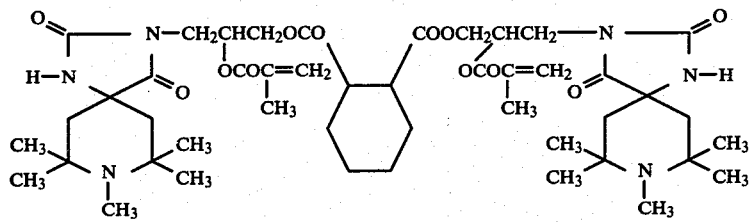
152.
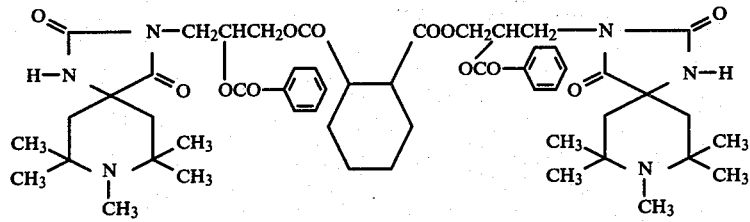
153.
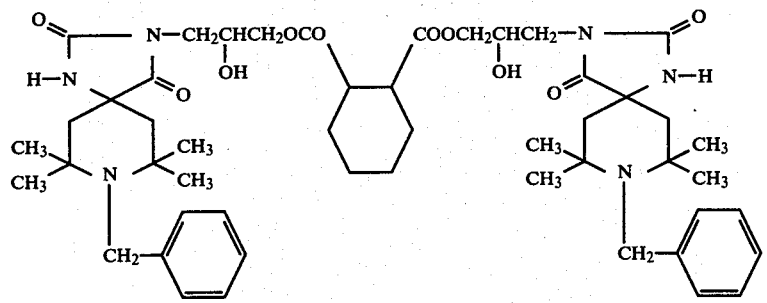
154.

-continued
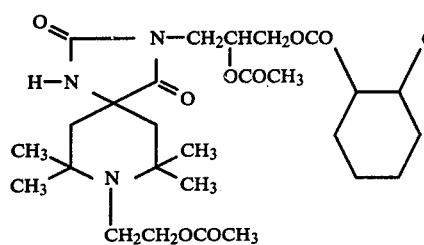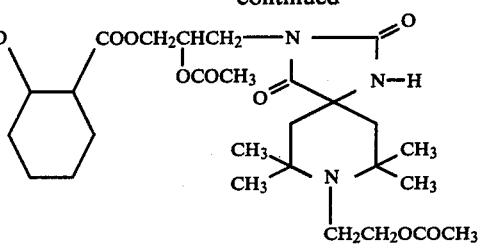 155.
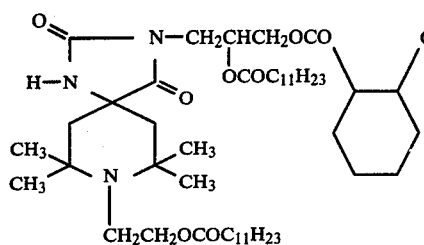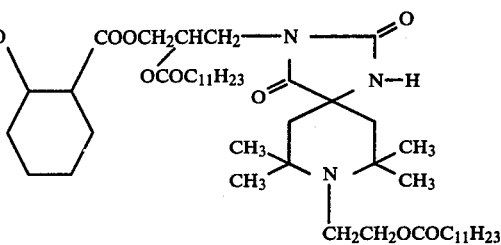 156.
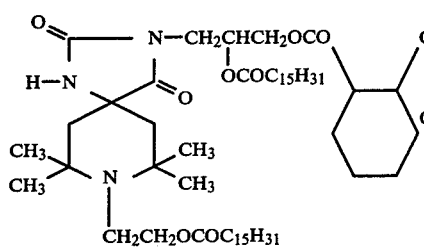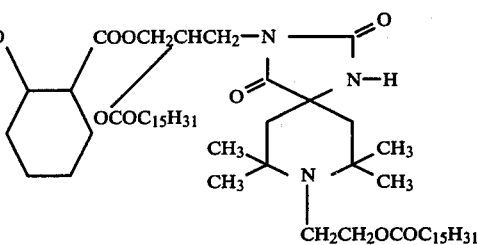 157.
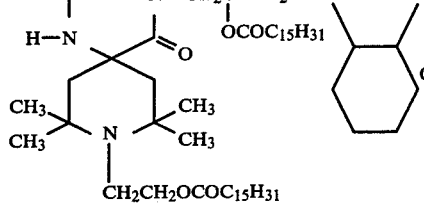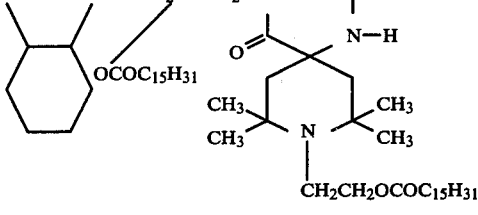 158.
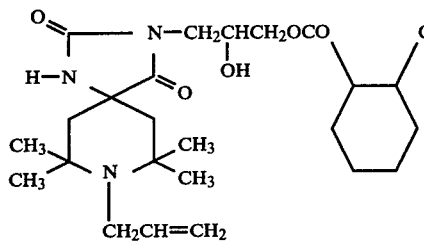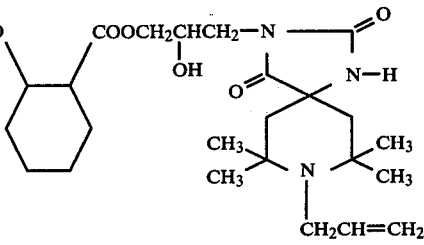 159.
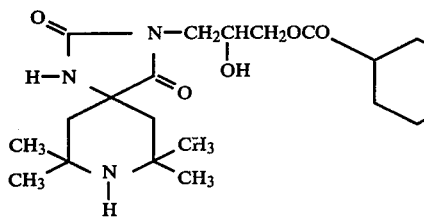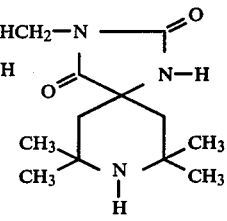 160.
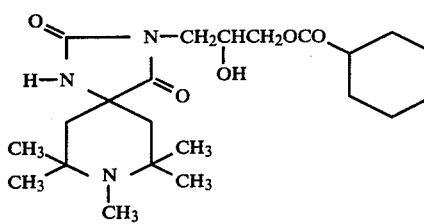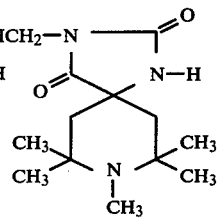 161.
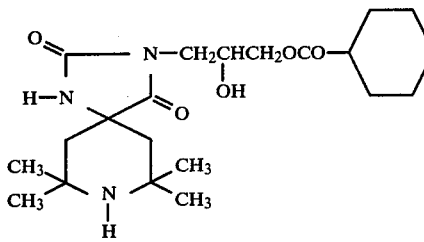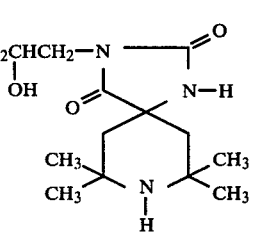

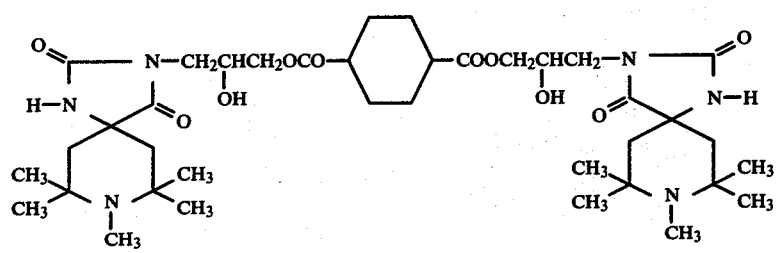
162.
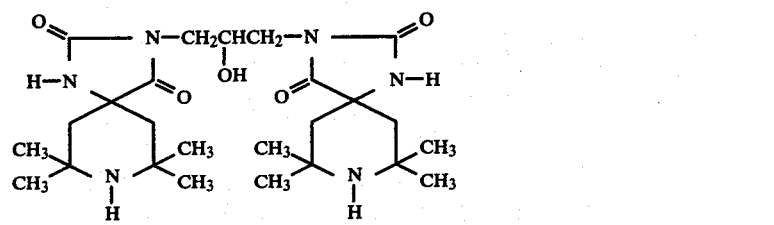
163.
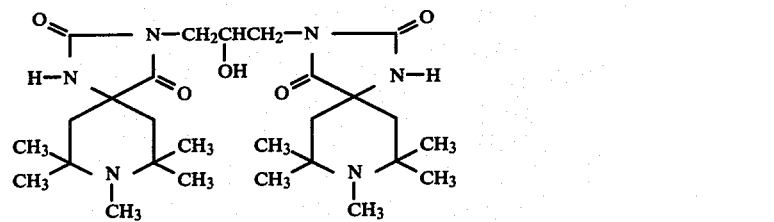
164.
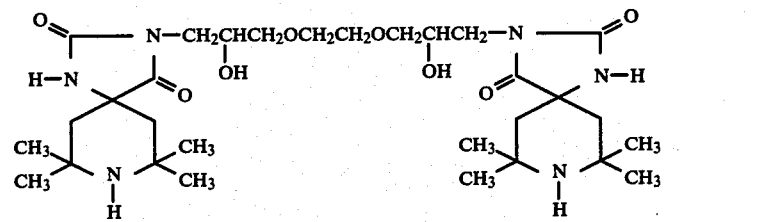
165.
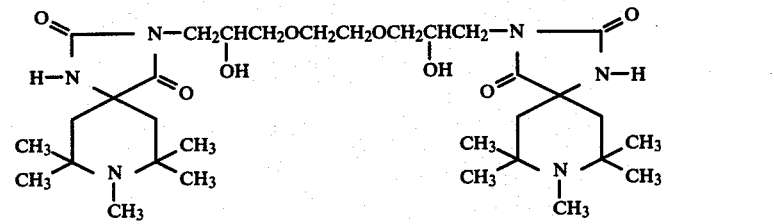
166.
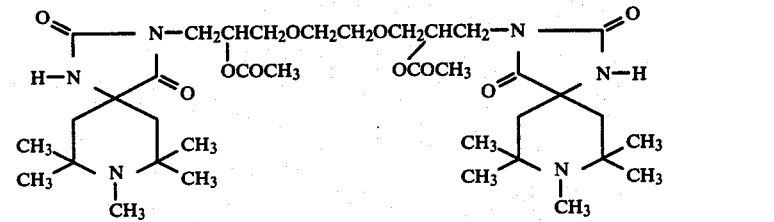
167.
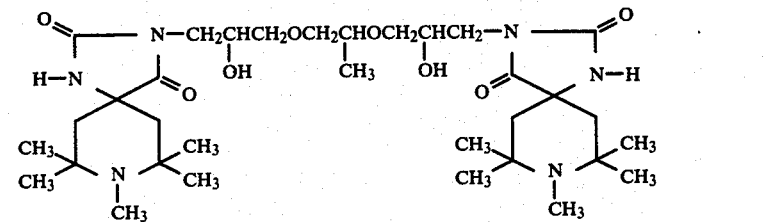
168.

-continued
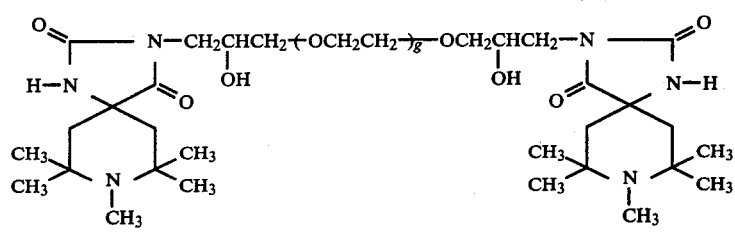 169.
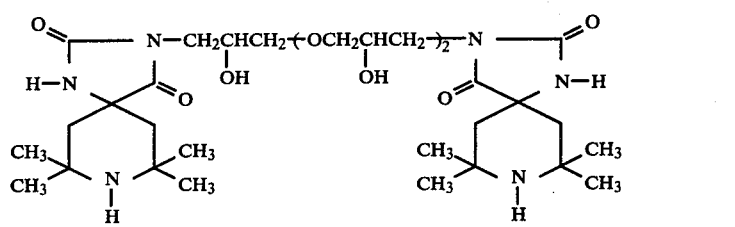 170.
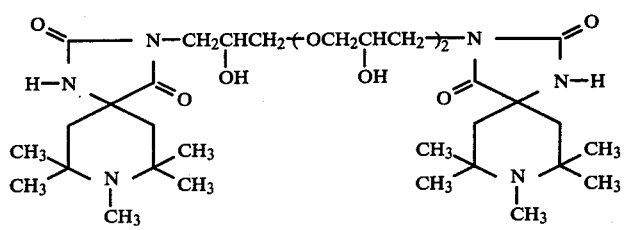 171.
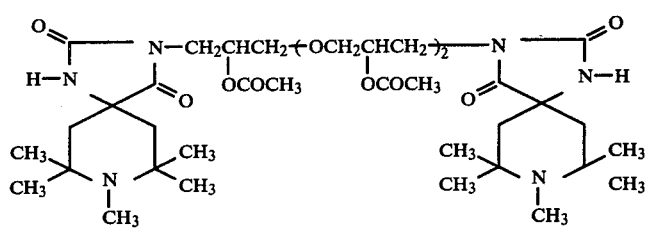 172.
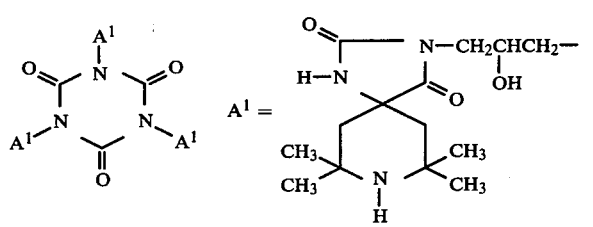 173.
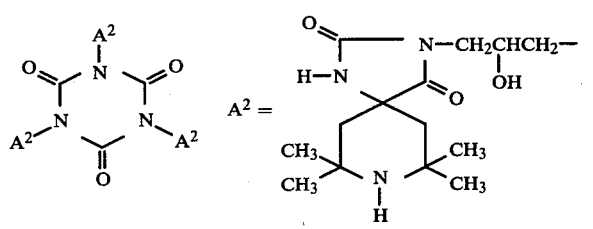 174.
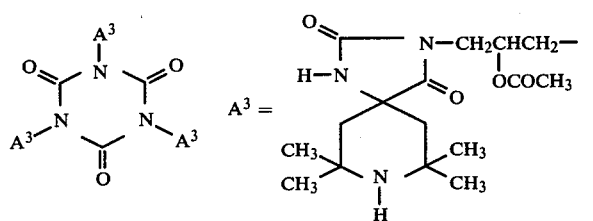 175.

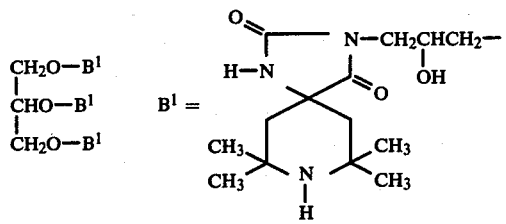
176.
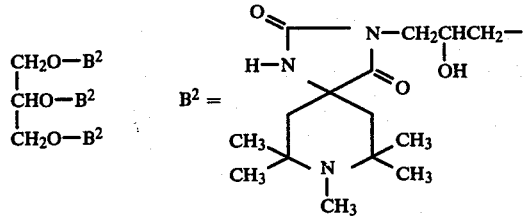
177.
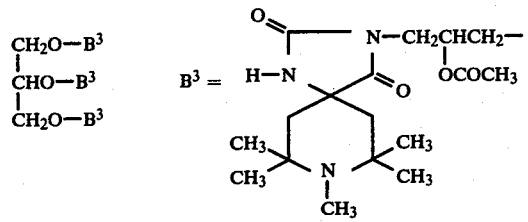
178.
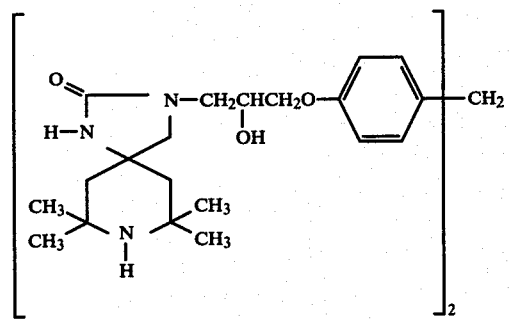
179.
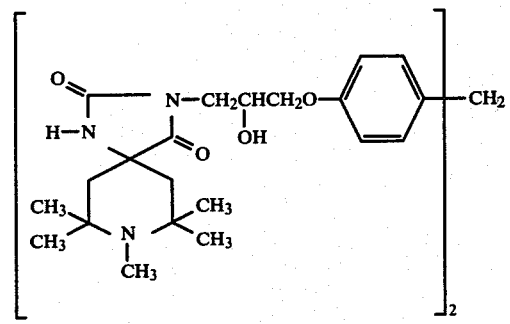
180.
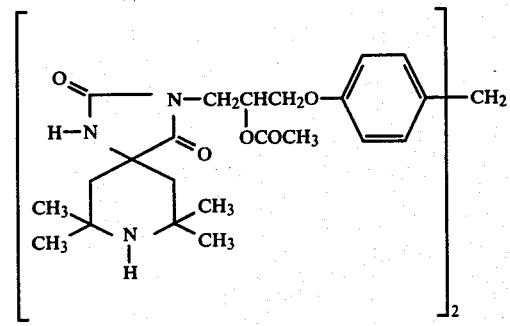
181.

182.
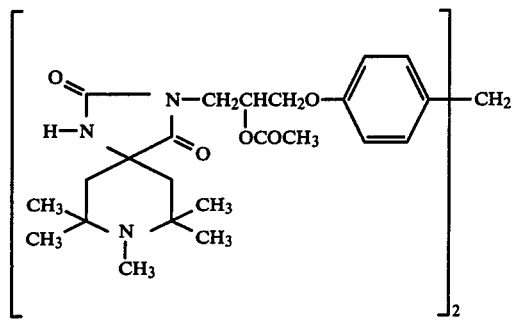
183.
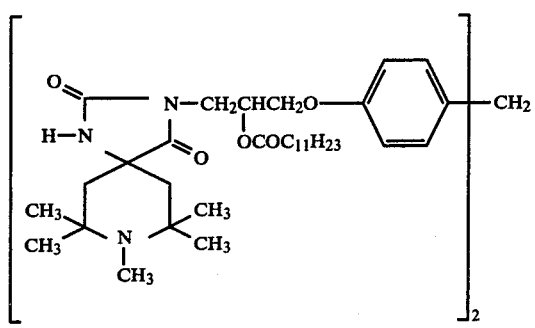
184.
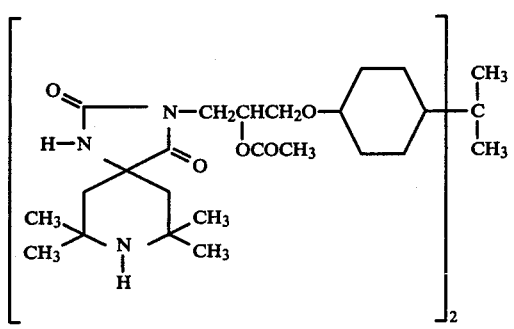
185.
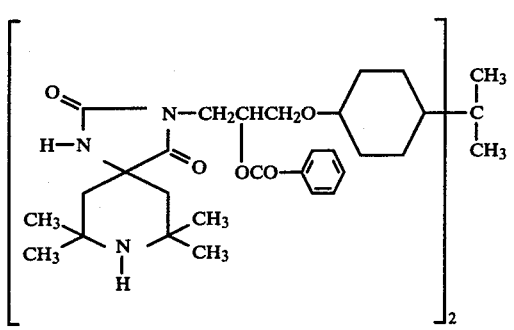
186.
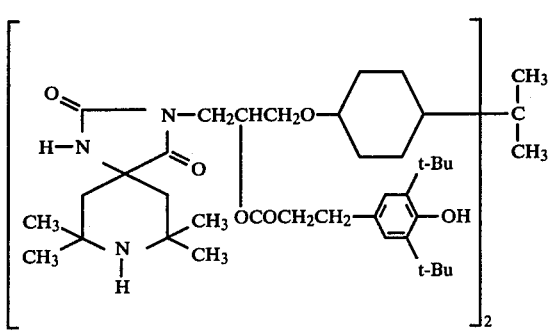

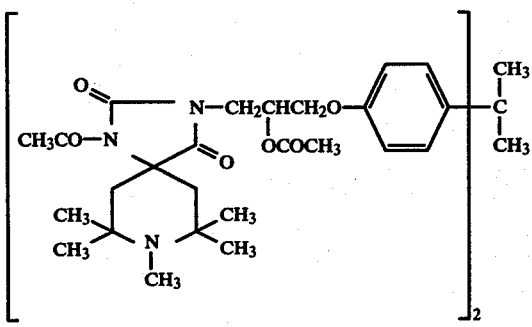
187.
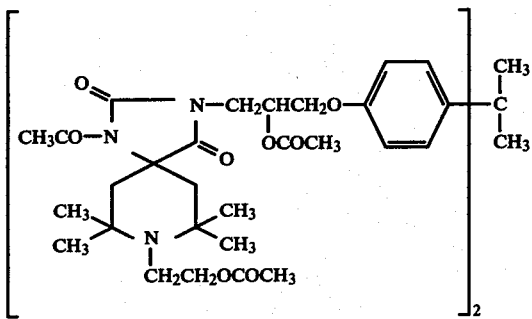
188.
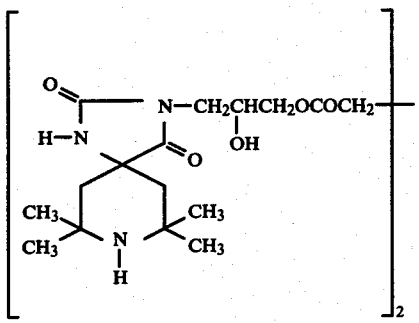
189.
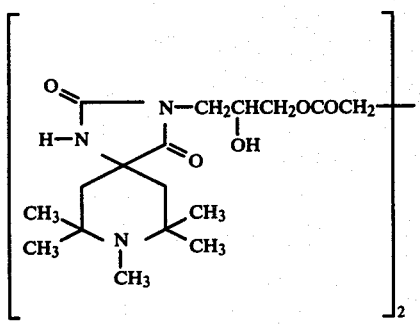
190.
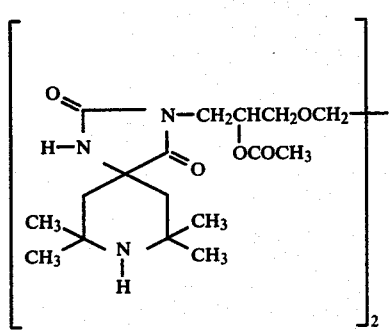
191.

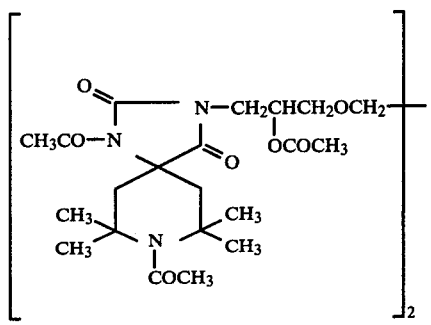
192.
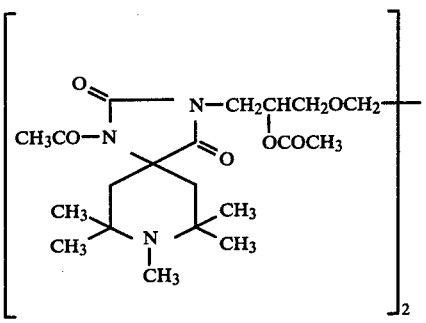
193.
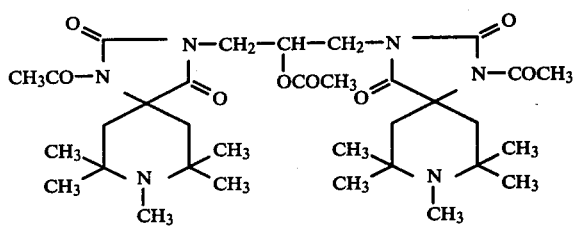
194.
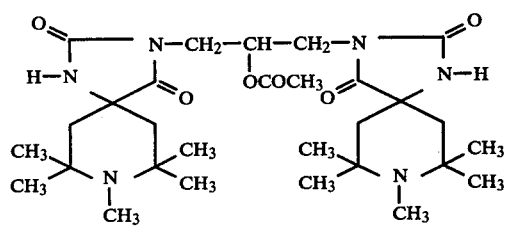
195.
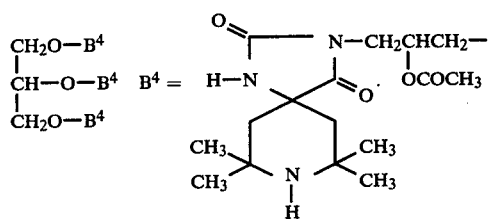
196.
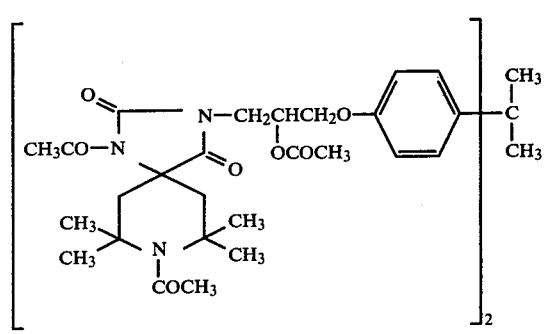
197.

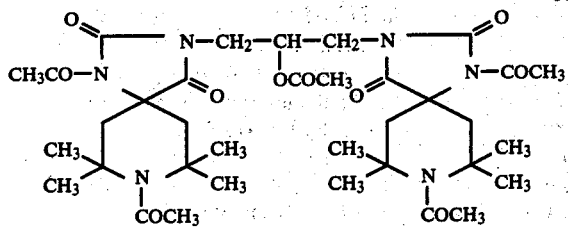

The hydantoin derivatives of formula (I) and acid addition salts thereof may be prepared by any one of the following methods, which can be performed under per se known conditions.

METHOD 1

Compounds of formula (I) in which $R^2$ and X each represent hydrogen atoms and Y represents a group of formula

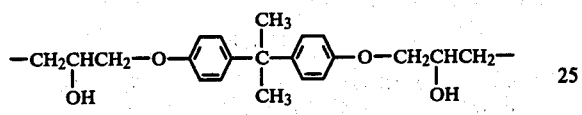

may be prepared by reacting a compound of formula (IV) with an epoxy compound of formula (V), according to the following reaction scheme to produce the desired compound of formula (III):

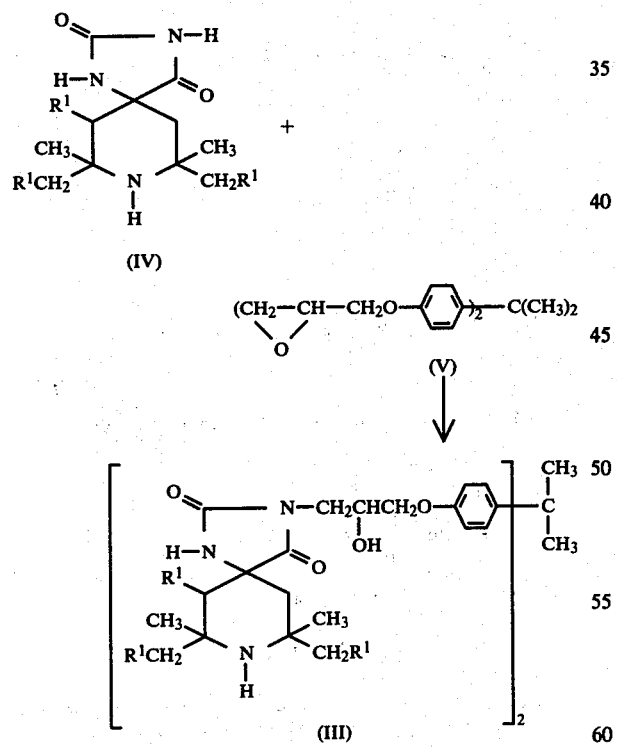

This process may also be applied to the preparation of the corresponding compounds of formula (I) in which Y represents one of the groups:

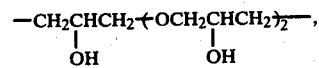

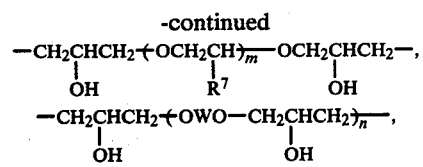

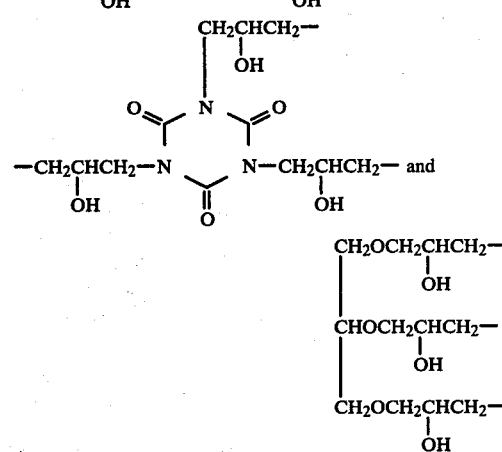

In preparing these compounds, of course, the compound of formula (V) is replaced by the corresponding epoxy compound containing the required group Y. Preparation of the starting materials of formula (IV) is described in U.S. Pat. No. 3,705,126 and in Japanese Patent Application No. 51-139842, as laid open to public inspection.

The reaction is preferably carried out by heating the compound of formula (IV) with the epoxy compound of formula (V) or other epoxy compound corresponding to the group Y which it is desired to introduce, preferably at a temperature of from 50°–180° C. The compound of formula (IV) is preferably employed in an amount slightly in excess of the stoichiometric amount. The reaction may be carried out in the presence or absence of an inert organic solvent and, where a solvent is employed, its nature is not critical, provided that it has no adverse effect upon the reaction. Examples of suitable solvents include: ethers, such as dioxan and diethylene glycol dimethyl ether; N,N-dialkylamides, such as N,N-dimethylformamide and N,N-dimethylacetamide; aromatic hydrocarbons, such as benzene, toluene or xylene; chlorinated aromatic hydrocarbons, such as chlorobenzene and p-dichlorobenzene; alcohols, such as methanol, ethanol, n-butanol, t-butanol and n-octanol; and aqueous methanol or aqueous ethanol Of these solvents, alcohols and aqueous alcohols are preferred. Best results are achieved if the reaction is carried out in the presence of a basic alkali metal compound, such as sodium hydroxide, potassium hydroxide or potassium carbonate; however, the presence of such a basic alkali metal compound is not essential.

METHOD 2

Compounds of formula (I) in which $R^2$ and X each represents a hydrogen atom and Y represents a group of formula —$CH_2CH(OH)CH_2$—, namely compounds having the following formula (VI), may be prepared by reacting an alkali metal salt of the compound of formula (IV) with a dihalo compound, e.g. a compound of formula (VII), according to the following reaction scheme:

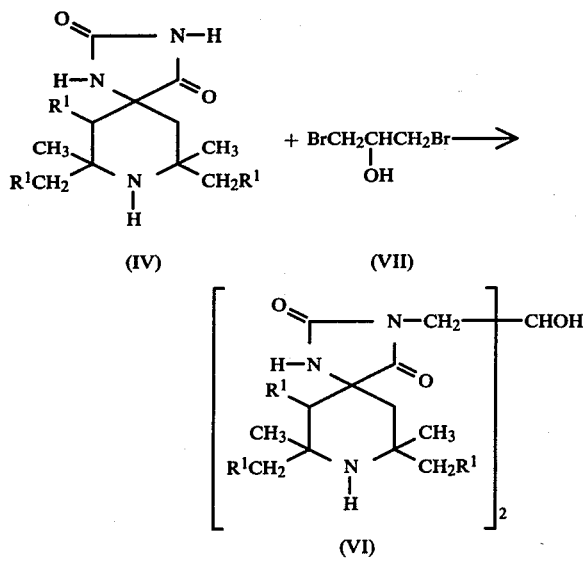

This process may also be applied to the preparation of the corresponding compounds of formula (I) in which Y represents one of the groups:

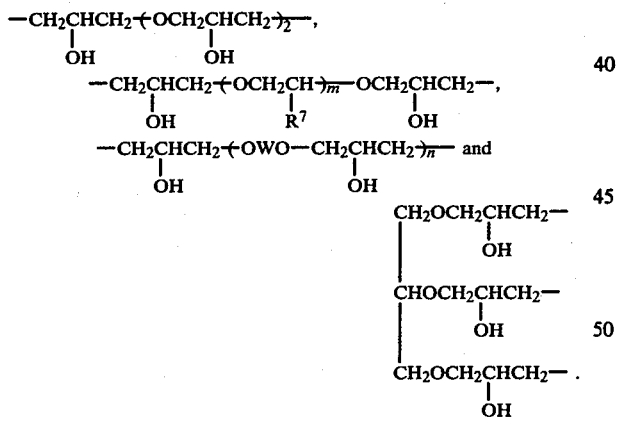

In this case, the compound of formula (VII) is replaced by a dihalo compound corresponding to the group Y which it is desired to introduce.

The reaction is advantageously carried out by reacting an alkali metal salt of compound (IV) with the diahlo compound in the presence of an inert organic solvent. The alkali metal salt of compound (IV) may be prepared in situ by reacting compound (IV) with, for example, an alkali metal hydroxide or carbonate, such as sodium hydroxide, potassium hydroxide or potassium carbonate. There is no particular limitation upon the nature of the solvent employed, provided that it has no adverse effect upon the reaction; examples of suitable solvents include: N,N-dialkylamides, such as N,N-dimethylformamide and N,N-dimethylacetamide; alcohols, such as methanol, ethanol and n-propanol, and mixtures of one or more of these solvents with water. The reaction is preferably carried out at a temperature which may vary from ambient temperature to 150° C.

Methods 1 and 2 illustrate the preparation of compounds of formula (I) in which X represents a hydrogen atom. Compounds in which X represents a substituent can be prepared by the following methods.

METHOD 3

Compounds of formula (I) in which $R^2$ and Z each represent hydrogen atoms and X represents one of the defined substituents, other than a hydrogen atom, may be prepared by following the procedure described in Method 1 but replacing compound (IV) by the corresponding compound in which the nitrogen atom at the 8-position is substituted. Preparation of compounds of this type is described in U.S. Patent No. 3,898,303 and in Japanese Patent Application No. 51-139842, as laid open to public inspection.

METHOD 4

Compounds of formula (I) in which $R^2$ represents a hydrogen atom and X represents one of the groups previously defined, other than a hydrogen atom, may be prepared by reacting an epoxy compound of formula (VIII) with a dihydroxy compound, for example, as illustrated in the following reaction scheme as applied to Bisphenol A:

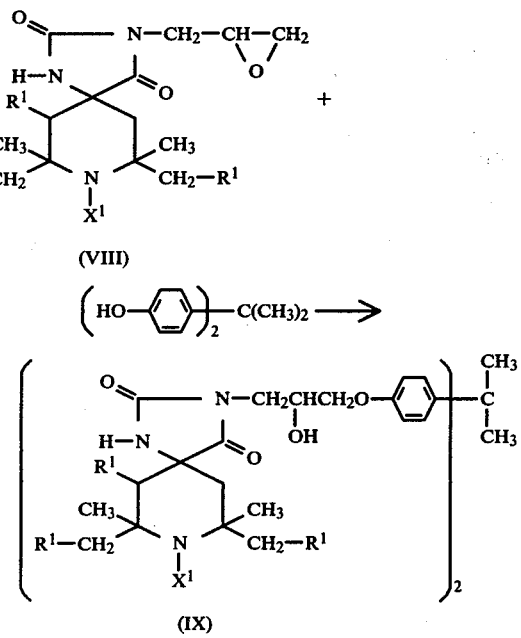

(in which X' is any one of the groups appearing in the definition of X, other than a hydrogen atom).

This method can also be employed wherein the Bisphenol A is replaced by one of the dicarboxylic acids HOCO—$(CH_2)_q$—COOH,

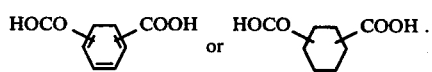

Preparation of the compound of formula (VIII) used as starting material is described in U.S. Pat. No. 3,941,744 and in Japanese Patent Application No. 51-139842, as laid open to public inspection.

The reaction is preferably carried out by heating the compound of formula (VIII) with the Bisphenol A or with the dicarboxylic acid at a temperature of from 80°–180° C. The reaction may be carried out in the presence or absence of an inert organic solvent and, if a solvent is employed, its nature is not critical to the process, provided that it has no adverse effect upon the reaction. Examples of suitable solvents are: N,N-dialkylamides, such as N,N-dimethylformamide and N,N-dimethylacetamide; ethers, such as dioxan and diethylene glycol diethyl ether; and t-butanol.

METHOD 5

Compounds of formula (I) in which $R^2$ represents a hydrogen atom and Z represents an alkyl, allyl or benzyl group may be prepared using the procedure described under Method 2 but replacing the dihalo compound (VII) by the corresponding compound containing the desired substituent Z.

METHOD 6

Compounds of formula (I) in which $R^2$ represents a hydrogen atom and Z represents an alkyl, allyl or benzyl group may also be prepared by reacting the corresponding compound of formula (I), which may have been obtained by any of Methods 1, 2, 3 or 4, with a strongly basic alkali metal compound (such as sodium hydride or potassium t-butyrate) and then with a halogen compound (in which the halogen atom is attached to the desired group Z) in the presence of an inert organic solvent (such as N,N-dimethylformamide, toluene, xylene, tetrahydrofuran or dioxan), normally with heating and preferably at a temperature from 50°–120° C.

METHOD 7

Compounds of formula (I) in which $R^2$ represents a hydrogen atom and Z represents an acyl group may be prepared by following the procedure described under Method 2, but replacing the dihalo compound (VII) by the corresponding compound in which Z is the desired substituent.

METHOD 8

Compounds of formula (I) in which $R^2$ represents a hydrogen atom and Z represents an acyl group may also be prepared by reacting the corresponding compound of formula (I) in which Z represents a hydrogen atom (and which may have been obtained by any one of Methods 1, 2, 3 and 4) with a reactive derivative of a carboxylic acid corresponding to the desired acyl group. Examples of such reactive derivatives include acid halides, acid anhydrides and lower alkyl esters of the acid.

When the reactive derivative employed is a lower alkyl ester of the acid, the reaction is preferably carried out in the presence of a strong base and of an inert organic solvent. The nature of the solvent is not critical, provided that it has no adverse effect upon the desired reaction; examples of suitable solvents are: aromatic hydrocarbons, such as benzene, toluene or xylene; and aliphatic hydrocarbons, such as n-heptane, n-octane or isooctane. Suitable strong bases include, for example: strongly basic alkali metal compounds, such as sodium methoxide, sodium ethoxide, potassium hydroxide or lithium amide; or titanic acid compounds, particularly organic esters of titanic acid, such as tetraisopropyl titanate or tetrabutyl titanate. It is preferred that the reaction should be carried out with heating, preferably at a temperature from 80°–180° C.

When a acid halide is employed as the reactive derivative, the reaction is preferably carried out in the presence of an acid-binding agent and in the presence of an inert organic solvent. Examples of suitable solvents are: aromatic hydrocarbons, such as benzene, toluene and xylene; chlorinated aliphatic hydrocarbons, such as chloroform and trichloroethane; and ethers, such as diethyl ether, tetrahydrofuran and dioxan. Suitable acid-binding agents include: alkali metal hydroxides, such as sodium hydroxide and potassium hydroxide; alkali metal carbonates, such as sodium carbonate and potassium carbonate; and organic bases, such as triethylamine and pyridine. The reaction is preferably carried out at a temperature from 0°–130° C.

Where the reactive derivative is an acid anhydride, the reaction is preferably carried out in the presence of an inert organic solvent or in the absence of a solvent but using an excess of acid anhydride. Where a solvent is employed, it is preferably selected from: aromatic hydrocarbons, such as benzene, toluene and xylene; and ethers, such as dioxan, tetrahydrofuran and diethylene glycol dimethyl ether. The reaction temperature may preferably be any temperature from ambient to 160° C.

In this process, if the starting material is a compound wherein Z represents a hydrogen atom and X represents a group of formula $-CH_2CH(OH)R^4$, the product may be a compound in which both $R^5$ in the group $-CH_2CH(OR^5)R^4$ represented by X and Z are same acyl group. Similarly, if the starting material is a compound in which both Z and X represent hydrogen atoms and it is acylated with an excess of acid halide or anhydride, the compound obtained may be a compound in which both Z and X represent the same acyl group.

METHOD 9

Compounds of formula (I) in which $R^2$ represents an hydrogen atom and Z represents a group of formula $-CONR^9R^{10}$ may be prepared by reacting the corresponding compound in which Z represents a hydrogen atom with a carbamic acid halide of formula Cl—$CONR^9R^{10}$. The reaction is preferably carried out in the presence of an acid-binding agent and in the presence of an inert organic solvent. The solvent is preferably an ether (such as tetrahydrofuran or dioxan) or an aromatic hydrocarbon (such as benzene or toluene). The acid-binding agent is preferably an organic base, such as triethylamine, N,N-diethylaniline or pyridine. The reaction is preferably carried out at a temperature from $-10°$ to $120°$ C.

METHOD 10

Compounds in which $R^2$ represents a hydrogen atom and Z represents a group of formula $-CONR^9R^{10}$ may also be prepared by reacting the corresponding compound in which Z represents a hydrogen atom with an isocyanate of formula $R^{10}NCO$; in this case, the group introduced is of formula $-CONHR^{10}$. The reaction may be carried out in the presence or absence of an inert organic solvent. Where a solvent is employed, its nature is not critical, provided that it has no adverse effect upon the desired reaction. Examples of suitable solvents are aromatic hydrocarbons (such as benzene, toluene and xylene) and ethers (such as tetrahydrofuran and dioxan). The reaction is preferably carried out at a temperature of from 50°–130° C.

METHOD 11

Compounds of formula (I) in which $R^2$ represents a hydrogen atom and Z represents one of the groups

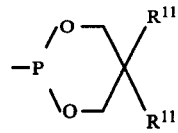

or $-P(OR^{12})_2$ may be prepared by reacting the corresponding compounds in which Z represents a hydrogen atom with a phosphorous halide of formula

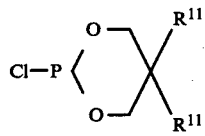

or $Cl-P(OR^{12})_2$. The reaction is preferably carried out in the presence of a base and of an inert organic solvent. Where a solvent is employed, its nature is not critical, provided that it has no adverse effect upon the reaction; examples of suitable solvents include: ethers, such as dioxan, tetrahydrofuran and diethyl ether; aliphatic, alicyclic or aromatic hydrocarbons such as n-hexane, cyclohexane, benzene and toluene; and N,N-dialkylamides, such as N,N-dimethylformamide and N,N-dimethylacetamide. The base is preferably a tertiary amine, such as triethylamine and N,N-diethylaniline. The reaction is preferably carried out at a temperature of from $-10°$ to $80°$ C.

METHOD 12

Compounds in which $R^2$ represents an alkyl, allyl, acetyl or benzyl group and in which X and Z each represent a hydrogen atom or any other of the defined substituents may be prepared by reacting the corresponding compound in which $R^2$ represents a hydrogen atom (which can be obtained by any one of the foregoing Methods 1 to 11) with a halogen compound of formula $R^2Cl$ in the presence of an alkali metal compound. Where the starting material employed in this reaction contains a hydroxy group, i.e. where X represents a group of formula $-CH_2CH(OH)R^4$ or when Z represents a hydrogen atom, the hydroxy groups are preferably first protected. The protection of these hydroxy groups may be carried out in any conventional manner, e.g. by protecting the groups by means of tetrahydropyranyl or p-nitrobenzoyl compounds.

The reaction of the starting material of formula (I) in which $R^2$ represents a hydrogen atom with the halogen compound of formula $R^2Cl$ (in which $R^2$ is as defined above other than a hydrogen atom) is preferably carried out as described in Japanese Patent Application No. 49-72332, as laid open to public inspection, preferably in the presence of an inert organic solvent. The nature of the solvent is not critical, provided that it has no adverse effect upon the reaction, but examples of suitable solvents include: ethers, such as tetrahydrofuran and dioxan; aromatic hydrocarbons, such as benzene and toluene; and amides, such as N,N-dimethylformamide and hexamethylphosphoric triamide. The alkali metal compound employed is preferably sodium hydride, butyllithium, sodium amide or potassium carbonate. The reaction is normally and preferably carried out at a temperature which may range from ambient to 160° C.

METHOD 13

Compounds in which $R^2$ represents a lower alkyl group, particularly methyl or ethyl, may also be prepared by reacting the corresponding compound in which $R^2$ represents a hydrogen atom with a di(lower alkyl)sulphate of formula $(R^2)_2SO_4$. In this case, if the starting material is a compound in which not only $R^2$ but also Z and/or X represents a hydrogen atom, the compound obtained is one in which both $R^2$ and Z and/or X represent identical alkyl groups.

The reaction may be carried out in the presence or absence of an inert organic solvent. If a solvent is employed, its nature is not critical, provided that it has no adverse effect upon the reaction. Examples of suitable solvents include: ethers, such as dioxan and tetrahydrofuran; lower aliphatic ketones such as acetone; and aromatic hydrocarbons, such as benzene and xylene. The reaction is preferably carried out in the presence of an alkali metal hydroxide or carbonate, such as sodium hydroxide, potassium hydroxide or potassium carbonate. The reaction is normally and preferably carried out at a temperature which may range from ambient temperature to 150° C.

METHOD 14

Compounds in which $R^2$ represents an acetyl group and X and Z each represent hydrogen atoms or the other groups defined above may be prepared by reacting the corresponding compound in which $R^2$ represents a hydrogen atom with, for example, an acid anhydride. When the starting material is a compound in which X and/or Z represents a hydrogen atom, X and/or Z in the compound obtained may also represent an acetyl group.

METHOD 15

Compounds of formula (I) in which X represents a methyl group and in which $R^2$ and Z may represent hydrogen atoms or any of the other groups defined may be prepared by reacting the corresponding compound in which X represents a hydrogen atom with formic acid and formaldehyde under the conditions well known for Leuckart-Wallach reactions.

METHOD 16

Compounds of formula (I) in which X represents the group $-CH_2CH(OH)R^4$ and in which $R^2$ and Z may be hydrogen atoms or the other defined groups may be prepared by reacting the corresponding compound in which X represents a hydrogen atom with an alkylene oxide or substituted alkylene oxide, such as ethylene oxide, propylene oxide or styrene oxide. The reaction is preferably effect in the presence of an acidic catalyst, such as sulphuric acid or hydrochloric acid, and preferably in an alcoholic solvent, such as methanol, ethanol or propanol. The reaction is normally and preferably carried out at a temperature of from 60°–160° C.

The hydroxy compound thus obtained may then be acylated or alkylated to give the desired ester or ether.

METHOD 17

Compounds of formula (I) in which X represents an alkyl group, an alkenyl group, a cyanoalkyl group, a 2,3-epoxypropyl group, a benzyl group or a group of formula —CH$_2$CH(OR$^5$)R$^4$ or —CH$_2$COOR$^6$ and in which R$^2$ and Z may be hydrogen atoms or the other defined groups may be prepared by reacting the corresponding compound in which X represents a hydrogen atom with a halogen compound of formula X-Cl (in which X is as defined above other than a hydrogen atom). This reaction may be carried out in the presence or absence of an inert organic solvent and following the procedure described in U.S. Pat. No. 3,941,744. Where a solvent is employed, its nature is not critical provided that it has no adverse effect upon the reaction. Examples of suitable solvents include: aromatic hydrocarbons, such as benzene, toluene and xylene; chlorinated hydrocarbons, such as chloroform, trichloroethane and chlorobenzene; and amides, such as N,N-dimethylformamide, N,N-dimethylacetamide and hexamethylphosphoric triamide. The reaction is preferably carried out at a temperature which may range from ambient temperature to 180° C.

METHOD 18

Compounds of formula (I) in which X represents an aliphatic acyl group or a group of formula

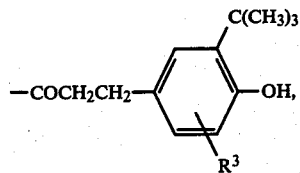

and in which R$^2$ represents a hydrogen atom or one of the other defined groups and Z is as defined above other than a hydrogen atom may be prepared by reacting the corresponding compound in which X represents a hydrogen atom with a carboxylic acid halide or, and more preferably, with an acid anhydride corresponding to the acyl group which it is desired to introduce. The reaction may be carried out following the procedure and employing the reactants previously described in Method 8.

METHOD 19

Acid addition salts of compounds of formula (I) may be prepared by neutralising the compound of formula (I) with a suitable acid, preferably in the presence of an inert organic solvent or a mixture thereof with water.

The hydantoin derivatives of formula (I) and their acid addition salts are useful for stabilizing polymers, particularly synthetic polymers, against the deterioration caused by heat and/or light. Accordingly, the invention further provides a polymeric composition comprising a polymer and, as stabilizer, a hydantoin derivative of formula (I) or an acid addition salt thereof. Organic polymers which can be stabilized in this way include:

olefin and diene polymers
including homopolymers of olefins and dienes (e.g. low-density, high-density and cross-linked polyethylenes, polypropylene, polyisobutylene, polymethylbutene-1, polymethylpentene-1, polyisoprene and polybutadiene), mixtures of such homopolymers (e.g. mixtures of polypropylene and polyethylene, polypropylene and polybutene-1, or polypropylene and polyisobutylene), and copolymers of olefins and dienes (e.g. ethylene/propylene copolymers, propylene/butene-1 copolymers, propylene/isobutylene copolymers, ethylene/butene-1 copolymers, and terpolymers of ethylene and propylene with dienes such as hexadiene, dicyclopentadiene or ethylidene norbornene);

styrene polymers
including polystyrene, copolymers of styrene and of α-methylstyrene (e.g. styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength), and graft copolymers of styrene (e.g. polymers in which styrene is grafted onto polybutadiene, and polymers in which styrene and acrylonitrile are grafted onto polybutadiene as well as mixtures thereof with the aforementioned styrene copolymers-commonly known as acrylonitrile/butadiene/styrene or ABS plastics);

halogenated vinyl and vinylidene polymers
including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids
and derivatives thereof, including polyacrylates and polymethacrylates, polyacrylic amides and polyacrylonitrile;

polymers derived from unsaturated alcohols and amines
and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers (e.g. ethylene/vinyl acetate copolymers);

epoxy polymers
including homopolymers and copolymers derived from epoxides (e.g. polyethylene oxide), and polymers derived from bis-glycidyl ethers;

polyacetals, polyalkylene oxides and polyphenylene oxides
including polyoxymethylene, oxymethylene/ethylene oxide copolymers, polyoxyethylene polypropylene oxide, polyisobutylene oxide and polyphenylene oxides;

polyurethanes and polyureas;

polycarbonates;

polysulphones;

polyamides and copolyamides derived from diamines and dicarboxylic acids and/or from aminocarboxylic acids or the corresponding lactams, including nylon-6, nylon-6,6, nylon-6,10, nylon-11 and nylon-12;

polyesters
derived from dicarboxylic acids and dialcohols and/or from hydroxycarboxylic acids and the corresponding lactones, e.g. polyethylene glycol terephthalate and poly-1,4-dimethylol-cyclohexane terephthalate;

cross-linked polymers
derived from aldehydes together with phenols, ureas or melamines, e.g. phenol/formaldehyde, urea/formaldehyde and melamine/formaldehyde resins;

alkyd resins
e.g. glycerol/phthalic acid resins and mixtures thereof with melamine/formaldehyde resins;

unsaturated polyester resins
derived from copolyesters of saturated and unsaturated dicarboxylic acids with polyhydric alcohols as well as from vinyl compounds as cross-linking agents, and also halogenated flame-resistant modifications thereof; and natural polymers
including cellulose, rubber and proteins, as well as chemically modified homologues thereof (e.g. cellulose acetates, cellulose propionates, cellulose butyrates and cellulose ethers such as methyl cellulose).

The amount of the stabilizers of the invention needed for effective stabilization of organic polymers will depend on a variety of factors, such as the type and properties of the polymer concerned, its intended use, and the presence of other stabilizers. It is generally satisfactory to use from 0.1% to 5% by weight of the stabilizers of the invention, based on the weight of the polymer, but the most effective range will vary with the type of polymer: viz. 0.01% to 2.0%, preferably 0.02% to 1.0%, by weight for olefin, diene and styrene polymers; 0.01% to 1.0%, preferably 0.02% to 0.5%, by weight for vinyl and vinylidene polymers; and 0.01% to 5.0%, preferably 0.02% to 2.0%, by weight for polyurethanes and polyamides. If desired, two or more of the stabilizers of the invention may be used together.

The stabilizers of the invention may readily be incorporated into organic polymers by conventional techniques at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer.

The stabilized polymeric composition of the invention may optionally also contain one or more of various additives conventionally used in polymer technology such as the additives listed in British patent specification No. 1,401,924, at pages 11 to 13.

The present invention is further illustrated by the following non-limiting Examples, in which all parts and percentages are by weight.

EXAMPLE 1

2,2-Bis{4-[2-hydroxy-3-(7,7,8,9,9-pentamethyl-2,4-dioxo-1,3,8-triazaspiro[4.5]dec-3-yl)propoxy]phenyl}propane (Compound No. 2)

26.3 g of 7,7,8,9,9-pentamethyl-1,3,8-triazaspiro[4.5]decane-2,4-dione, 17.0 g of 2,2-bis[p-(2,3-epoxypropoxy)phenyl]propane and 0.5 g of potassium hydroxide were added to 200 ml of methanol, and the mixture was refluxed for 8 hours. After completion of the reaction, the mixture was allowed to cool and the crystals which precipitated were washed with methanol and then recrystallized from benzene to give Compound No. 2 in the form of white crystals melting at 241°–244° C.

EXAMPLE 2

2,2-Bis{4-[2-hydroxy-3-(7,7,9,9-tetramethyl-2,4-dioxo-1,3,8-triazaspiro[4.5]dec-3-yl)propoxy]phenyl}propane (Compound No. 1)

24.0 g of 7,7,9,9-tetramethyl-1,3,8-triazaspiro[4.5]decane-2,4-dione, 17.0 g of 2,2-bis[p-(2,3-epoxypropoxy)phenyl]propane and 0.5 g of potassium hydroxide were reacted in 400 ml of 50% v/v aqueous ethanol, following the procedure described in Example 1. The desired Compound No. 1 was obtained in the form of crystals melting at 117°–119° C.

EXAMPLE 3

2,2-Bis{4-[2-hydroxy-3-(7,9-diethyl-6,7,9-trimethyl-2,4-dioxo-1,3,8-triazaspiro[4.5]dec-3-yl)propoxy]phenyl}propane (Compound No. 104)

4.1 g of 7,9-diethyl-6,7,9-trimethyl-1,3,8-triazaspiro[4.5]decane-2,4-dione, 2.5 g of 2,2-bis[p-(2,3-epoxypropoxy)phenyl]propane and 0.05 g of potassium hydroxide were reacted in a mixture of 150 ml of N,N-dimethylformamide and 20 ml of methanol, following substantially the same procedure as described in Example 1. The desired Compound No. 104 was obtained in the form of a white powder, showing an $R_f$ value of 0.66 on thin-layer chromatography on silica gel using a 8:1:1:1 by volume mixture of ethyl acetate, benzene, ethanol and triethylamine as developing solvent.

EXAMPLE 4

1,1'-[Isopropylidenebis(p-phenyleneoxy)]bis(3-[p-{p-[2-hydroxy-3-(7,7,8,9,9-pentamethyl-2,4-dioxo-1,3,8-triazaspiro[4.5]dec-3-yl)propoxy]-α,α-dimethylbenzyl}-phenoxy]2-propanol) (Compound No. 108)

16.0 g of 7,7,8,9,9-pentamethyl-1,3,8-triazaspiro[4.5]decane-2,4-dione, 25.0 g of 1,1'-[isopropylidenebis(p-phenyleneoxy)]bis[3-{p-[p-(2,3-epoxypropoxy)-α,α-dimethylbenzyl]phenoxy}-2-propanol] and 0.2 g of potassium hydroxide were dissolved in a mixed solvent consisting of 250 ml of methanol and 50 ml of N,N-dimethylformamide, and the mixture was then allowed to react, following substantially the procedure described in Example 1. The desired Compound No. 108 was obtained in the form of a white powder, having an $R_f$ value of 0.42 on thin-layer chromatography on silica gel using a 20:2:2:1 mixture of ethyl acetate, benzene, ethanol and triethylamine as developing solvent.

EXAMPLE 5

2,2-Bis{4-[2-hydroxy-3-(7,7,9,9-tetramethyl-2,4-dioxo-1,3,8-triazaspiro[4.5]dec-3-yl)propoxy]cyclohexyl}propane (Compound No. 118)

40.0 g of 7,7,9,9-tetramethyl-1,3,8-triazaspiro[4.5]decane-2,4-dione, 17.5 g of 2,2-bis[4-(2,3-epoxypropoxy)cyclohexyl]propane and 2.0 g of potassium hydroxide were reacted in 300 ml of methanol, following substantially the same procedure as was described in Example 1. The desired Compound No. 118 was obtained in the form of a white powder, having an $R_f$ value of 0.56 on thin-layer chromatography on silica gel using a 8:1:1:1 by volume mixture of ethyl acetate, benzene, ethanol and triethylamine as developing solvent.

EXAMPLE 6

Bis[2-hydroxy-3-(7,7,8,9,9-pentamethyl-2,4-dioxo-1,3,8-triazaspiro[4.5]dec-3-yl)propyl]adipate (Compound No. 126)

9.6 g of 7,7,8,9,9-pentamethyl-1,3,8-triazaspiro[4.5]decane-2,4-dione, 5.2 g of bis(2,3-epoxypropyl)adipate and 0.1 g of potassium hydroxide were reacted in 80 ml of t-butanol, following substantially the same procedure as in Example 1. The desired Compound No. 126 was obtained in the form of white crystals, melting at 180°–184° C.

EXAMPLE 7

Bis[2-hydroxy-3-(7,7,8,9,9-pentamethyl-2,4-dioxo-1,3,8-triazaspiro[4.5]dec-3-yl)propyl]phthalate (Compound No. 130)

24.0 g of 7,7,8,9,9-pentamethyl-1,3,8-triazaspiro[4.5]decane-2,4-dione, 12.0 g of bis(2,3-epoxypropyl)phthalate and 0.5 g of potassium hydroxide were reacted in 200 ml of N,N-dimethylformamide, following substantially the same procedure as in Example 1. The desired Compound No. 130 was obtained in the form of a white powder, having an $R_f$ value of 0.47 on thin-layer chromatography on silica gel using a 8:1:1:1 by volume mixture of ethyl acetate, benzene, ethanol and triethylamine as developing solvent.

EXAMPLE 8

Bis[2-hydroxy-3-(7,7,8,9,9-pentamethyl-2,4-dioxo-1,3,8-triazaspiro[4.5]dec-3-yl)propyl]1,2-cyclohexanedicarboxylate (Compound No. 147)

27.0 g of 7,7,8,9,9-pentamethyl-1,3,8-triazaspiro[4.5]decane-2,4-dione, 14.0 g of bis(2,3-epoxypropyl)1,2-cyclohexanedicarboxylate and 0.2 g of potassium hydroxide were reacted in 300 ml of methanol, following substantially the same procedure as in Example 1. The desired Compound No. 147 was obtained in the form of white crystals melting at 119°–122° C.

EXAMPLE 9

Ethylene glycol bis[2hydroxy-3-(7,7,8,9,9-pentamethyl-2,4-dioxo-1,3,8-triazaspiro[4.5]dec-3-yl)propyl]ether (Compound No. 166)

10.0 g of 7,7,8,9,9-pentamethyl-1,3,8-triazaspiro[4.5]decane-2,4-dione, 3.0 g of ethylene glycol bis(2,3-epoxypropyl)ether and 0.1 g of potassium hydroxide were reacted in 60 ml of methanol, following substantially the same procedure as in Example 1. The desired Compound No. 166 was obtained in the form of white crystals, melting at 213°–215° C.

EXAMPLE 10

Nonaethylene glycol bis[2-hydroxy-3-(7,7,8,9,9-pentamethyl-2,4-dioxo-1,3,8-triazaspiro[4.5]dec-3-yl)propyl]ether (Compound No. 169)

5.8 g of 7,7,8,9,9-pentamethyl-1,3,8-triazaspiro[4.5]decane-2,4-dione, 5.3 g of nonaethylene glycol bis(2,3-epoxypropyl)ether and 0.1 g of potassium hydroxide were reacted in 100 ml of methanol, following substantially the same procedure as in Example 1. The desired Compound No. 169 was obtained in the form of a colourless, viscous liquid, having an $R_f$ value of 0.38 on thin-layer chromatography on silica gel using a 2:1:0.03 by volume mixture of ethyl acetate, methanol and triethylamine as developing solvent.

EXAMPLE 11

Glycerol tris[2-hydroxy-3-(7,7,8,9,9-pentamethyl-2,4-dioxo-1,3,8-triazaspiro[4.5]dec-3-yl)propyl]ether (Compound No. 177)

12.0 g of 7,7,8,9,9-pentamethyl-1,3,8-triazaspiro[4.5]decane-2,4-dione, 4.1 g of glycerol tris(2,3-epoxypropyl)ether and 1.1 g of potassium hydroxide were reacted in 80 ml of methanol, following substantially the same procedure as in Example 1. The desired Compound No. 177 was obtained in the form of a white powder, having an $R_f$ value of 0.45 on thin-layer chromatography on silica gel using a 4:4:4:1:1 by volume mixture of benzene, ethyl acetate, chloroform, methanol and triethylamine as developing solvent.

EXAMPLE 12

Tris[2-hydroxy-3-(7,7,8,9,9-pentamethyl-2,4-dioxo-1,3,8-triazaspiro[4.5]dec-3-yl)propyl]isocyanate (Compound No. 174)

40.0 g of 7,7,8,9,9-pentamethyl-1,3,8-triazaspiro[4.5]decane-2,4-dione, 10.0 g of tris(2,3-epoxypropyl)isocyanurate and 1.0 g of potassium hydroxide were reacted in 200 ml of methanol, following substantially the same procedure as in Example 1. The desired Compound No. 174 was obtained in the form of white crystals melting at 155°–157° C.

EXAMPLE 13

2,2-Bis{4-[2-octanoyloxy-3-(7,7,8,9,9-pentamethyl-2,4-dioxo-1,3,8-triazaspiro[4.5]dec-3-yl)propoxy]phenyl}propane (Compound No. 37)

A mixture of 8.0 g of 2,2-bis{4[2-hydroxy-3-(7,7,8,9,9-pentamethyl-2,4-dioxo-1,3,8-triazaspiro[4.5]dec-3-yl)propoxy]phenyl}propane obtained as described in Example 1, and 15.0 g of n-octanoic anhydride was heated at 140°–150° C. for 3 hours, with stirring. 10.0 g of potassium carbonate was added in small portions to the mixture and then the heating was continued at the same temperature, with stirring, for an additional 2 hours. When the reaction was complete, the reaction mixture was cooled and 200 ml of benzene were added thereto. The benzene solution was washed with a 3% w/w aqueous solution of potassium carbonate and then dried over anhydrous potassium carbonate. The solvent was then removed from the reaction mixture, leaving a residue, which was recrystallised from a 2:1 by volume mixture of petroleum benzine/benzene, to give the desired Compound No. 37, in the form of white crystals melting at 131°–135° C.

EXAMPLE 14

2,2-Bis{4-[2-acetoxy-3-(7,7,8,9,9-pentamethyl-2,4-dioxo-1,3,8-triazaspiro[4.5]dec-3-yl)propoxy]phenyl}propane (Compound No. 35)

A mixture of 4.0 g of 2,2-bis{4-[2-hydroxy-3-(7,7,8,9,9-pentamethyl-2,4-dioxo-1,3,8-triazaspiro[4.5]dec-3-yl)propoxy]phenyl}propane, obtained as described in Example 1, and 100 ml of acetic anhydride was heated at 120°–130° C. for 6 hours. The reaction mixture was then treated substantially as described in Example 13, to give the desired Compound No. 35 in the form of white crystals melting at 229°–237° C.

EXAMPLE 15

2,2-Bis{4-[2-benzoyloxy-3-(7,7,8,9,9-pentamethyl-2,4-dioxo-1,3,8-triazaspiro[4.5]dec-3-yl)propoxy]phenyl}propane (Compound No. 45)

A mixture of 4.0 g of 2,2-bis{4-[2-hydroxy-3-(7,7,8,9,9-pentamethyl-2,4-dioxo-1,3,8-triazaspiro[4.5]dec-3-yl)propoxy]phenyl}propane obtained as described in Example 1, 4.0 g of potassium carbonate and 4.0 g of benzoic anhydride was reacted using substantially the same procedure as described in Example 13, to give the desired Compound No. 45 in the form of white crystals melting at 206°–211° C.

EXAMPLE 16

2,2-Bis{4-[2-dodecyloxy-3-(7,7,8,9,9-pentamethyl-2,4-dioxo-1,3,8-triazaspiro[4.5]dec-3-yl)propoxy]phenyl}propane (Compound No. 34)

1.5 g of sodium hydride was added, with stirring, to a solution of 8.2 g of 2,2-bis{4-[2-hydroxy-3-(7,7,8,9,9-pentamethyl-2,4-dioxo-1,3,8-triazaspiro[4.5]dec-3-yl)propoxy]phenyl}propane, prepared as described in Example 1, in 150 ml of N,N-dimethylformamide, and the mixture was stirred at 50°–60° C. for 2 hours. 10.0 g of n-dodecyl bromide were then added dropwise to the mixture and the whole mixture was heated at 50°–60° C. for two hours and then at 70°–80° C. for a further 4 hours, stirring all the time. After completion of the reaction, the reaction mixture was condensed by evaporation under reduced pressure and then 200 ml of benzene were added to the resulting residue. This solution was then washed with, in turn, a 2% w/w aqueous solution of sodium carbonate and water. The washed solution was dried over anhydrous potassium carbonate and then the solvent was removed by evaporation under reduced pressure. The residue was purified by column chromatography through silica gel eluted with a 32:4:5:1 by volume mixture of ethyl acetate, benzene, ethanol and triethylamine, giving the desired Compound No. 34 as a colourless, viscous liquid, having an $R_f$ value of 0.53 on thin-layer chromatography on silica gel using a 20:2:2:1 by volume mixture of ethyl acetate, benzene, ethanol and triethylamine as developing solvent.

EXAMPLE 17

2,2-Bis{4-[2-methoxy-3-(1,7,7,8,9,9-hexamethyl-2,4-dioxo-1,3,8-triazaspiro[4.5]dec-3-yl)propoxy]phenyl}propane (Compound No. 92)

2.0 g of 2,2-bis{4-[2-hydroxy-3-(7,7,8,9,9-pentamethyl-2,4-dioxo-1,3,8-triazaspiro[4.5]-dec-3-yl)propoxy]phenyl}propane, prepared as described in Example 1, and 1.5 g of potassium hydroxide were added to 100 ml of dioxan. 3.5 g of dimethyl sulphate were then added dropwise to the mixture, with stirring, at 40°–50° C. After the addition was complete, the mixture was heated, with stirring, at 70°–80° C. for 6 hours. After completion of the reaction, the reaction mixture was condensed by evaporation under reduced pressure and benzene was added to dissolve the residue thus obtained. The benzene solution was washed with, in turn, a 3% w/w aqueous solution of sodium hydroxide and water. The solvent was removed; then the residue was purified by column chromatography through silica gel using a 8:1:1:1 by volume mixture of ethyl acetate, benzene, ethanol and triethylamine as eluent, giving the desired Compound No. 92 as a white powder, having an $R_f$ value of 0.54 on thin-layer chromatography on silica gel using a 8:1:1:1 by volume mixture of ethyl acetate, benzene, ethanol and triethylamine as developing solvent.

EXAMPLE 18

2,2-Bis{4-[2-hydroxy-3-(8-β-hydroxyethyl-7,7,9,9-tetramethyl-2,4-dioxo-1,3,8-triazaspiro[4.5]dec-3-yl)propoxyl]phenyl}propane (Compound No. 8)

1.4 g of 2,2-bis{4-[2-hydroxy-3-(7,7,9,9-tetramethyl-2,4-dioxo-1,3,8-triazaspiro[4.5]dec-3-yl)propoxy]phenyl}propane (prepared as described in Example 2), 3 ml of ethylene oxide and a drop of concentrated hydrochloric acid were added to 60 ml of methanol, and then the mixture was heated in a sealed tube for 18 hours at a temperature of 105°–115° C. After completion of the reaction, the resulting mixture was condensed by evaporation under reduced pressure and then the residue so produced was recrystallised successively from benzene and from ethanol to give the desired Compound No. 8, melting point 233°–236° C.

EXAMPLE 19

2,2-Bis{4-[2-methylcarbamoyloxy-3-(7,7,9,9-tetramethyl-2,4-dioxo-1,3,8-triazaspiro[4.5]dec-3-yl)propoxy]phenyl}propane (Compound No. 31)

A mixture of 5.0 g of 2,2-bis{4-[2-hydroxy-3-(7,7,9,9-tetramethyl-2,4-dioxo-1,3,8-triazaspiro[4.5]dec-3-yl)propoxy]phenyl}propane (prepared as described in Example 2) and 25.0 g of methyl isocyanate was refluxed for 8.5 hours. After completion of the reaction, excess methyl isocyanate was evaporated from the reaction mixture and then the residue was purified by column chromatography through silica gel eluted with a 24:12:2:1 by volume mixture of ethyl acetate, benzene, triethylamine and ethanol and then by recrystallisation from ethanol. The desired Compound No. 31 was obtained in the form of white crystals, melting point 238°–242° C.

EXAMPLE 20

2,2-Bis{4-[2-phenylcarbamoyloxy-3-(7,7,9,9-tetramethyl-2,4-dioxo-1,3,8-triazaspiro[4.5]dec-3-yl)propoxy]phenyl}propane (Compound No. 32)

A mixture of 5.0 g of 2,2-bis{4-[2-hydroxy-3-(7,7,9,9-tetramethyl-2,4-dioxo-1,3,8-triazaspiro[4.5]dec-3-yl)propoxy]phenyl}propane (prepared as described in Example 2) and 50.0 g of isocyanate was reacted, following substantially the same procedure as described in Example 19. The desired Compound No. 32 was thus obtained in the form of crystals, melting point 202°–207° C.

EXAMPLE 21

2,2-Bis{4-[2-acetoxy-3-(8-acetyl-7,7,9,9-tetramethyl-2,4-dioxo-1,3,8-triazaspiro[4.5]dec-3-yl)propoxy]phenyl}propane (Compound No. 68)

5 g of 2,2-bis{4-[2-hydroxy-3-(7,7,9,9-tetramethyl-2,4-dioxo-1,3,8-triazaspiro[4.5]dec-3-yl)propoxy]phenyl}propane were heated at 100°–110° C. in 100 ml of acetic anhydride, with stirring, for 6 hours. After completion of the reaction, the reaction mixture was condensed by evaporation under reduced pressure and then 150 ml of benzene were added to dissolve the residue. The benzene solution was washed successively with a 2% w/w sodium carbonate solution and water. The solvent was then removed and the residue was purified by column chromatography through silica gel eluted with a 8:1:1:1 by volume mixture of ethyl acetate, benzene, ethanol, and triethylamine. The desired Compound No. 68 was obtained in the form of white crystals, melting point 147°–149° C.

EXAMPLE 22

2-Hydroxy-1,3-bis(7,7,8,9,9-pentamethyl-2,4-dioxo-1,3,8-triazaspiro[4.5]dec-3-yl)propane (Compound No. 164)

22.0 g of 7,7,8,9,9-pentamethyl-1,3,8-triazaspiro[4.5]decane-2,4-dione and 5.1 g of potassium hydroxide were added to 200 ml of N,N-dimethylformamide, and the mixture was heated, with stirring, for 30 minutes at 50°–60° C. At the end of this time, 9.0 g of 1,3-dibromo-2-propanol were added dropwise to the mixture and the whole mixture was heated, with stirring, for 6 hours at 100°–110° C. After completion of the reaction, the reaction mixture was condensed by evaporation and the residue was washed with a 1% w/w aqueous solution of potassium hydroxide and then recrystallised from a 2:1 by volume mixture of benzene and ethanol, giving the desired Compound No. 164 in the form of white crystals, melting point 255°–256° C.

EXAMPLE 23

2,2-Bis{4-[2-acetoxy-3-(1-acetyl-7,7,8,9,9-pentamethyl-2,4-dioxo-1,3,8-triazaspiro[4.5]dec-3-yl)propoxy]phenyl}propane (Compound No. 187)

A mixture of 4.1 g of 2,2-bis{4-[2-hydroxy-3-(7,7,8,9,9-pentamethyl-2,4-dioxo-1,3,8-triazaspiro[4.5]dec-3-yl)propoxy]phenyl}propane, 100 ml of acetic anhydride and 3.3 g of anhydrous potassium carbonate was heated, with stirring, at 130°–140° C. for 8 hours. The reaction mixture was then condensed by evaporation under reduced pressure and 300 ml of benzene were added to dissolve the residue. The benzene solution was washed with a 3% w/w aqueous solution of potassium carbonate and then dried over anhydrous potassium carbonate. The solvent was distilled from the dried reaction mixture and the resulting residue was purified by column chromatography through silica gel eluted with a 40:10:4:1 mixture of ethyl acetate, benzene, ethanol and triethylamine. The desired compound was obtained in the form of a white powder softening at 98°–102° C. The compound had an $R_f$ value of 0.43 on thin-layer chromatography on silica gel using a 40:10:4:1 by volume mixture of ethyl acetate, benzene, ethanol and triethylamine as developing solvent.

EXAMPLE 24

2,2-Bis{4-[2-acetoxy-3-(1-acetyl-8-β-acetoxyethyl-7,7,9,9-tetramethyl-2,4-dioxo-1,3,8-triazaspiro[4.5]dec-3-yl)propoxy]phenyl}propane (Compound No. 188)

A mixture of 1 g of 2,2-bis{4-[2-hydroxy-3-(8-β-hydroxyethyl-7,7,9,9-tetramethyl-2,4-dioxo-1,3,8-triazaspiro[4.5]dec-3-yl)propoxy]phenyl}propane (obtained as described in Example 18) and 20 g of acetic anhydride was refluxed for 60 hours. After completion of the reaction, the reaction mixture was poured into ammoniacal ice-water, extracted with benzene and then purified by column chromatography through silica gel eluted with a 2:1 by volume mixture of benzene and ethyl acetate, to give the desired Compound No. 188 in the form of white crystals. The compound had an $R_f$ value of 0.86 on thin-layer chromatography on silica gel using a 1:1:1 by volume mixture of n-hexane, benzene and ethyl acetate as developing solvent.

EXAMPLE 25

Bis[2-hydroxy-3-(7,7,9,9-tetramethyl-2,4-dioxo-1,3,8-triazaspiro[4.5]dec-3-yl)propyl]adipate (Compound No. 125)

A mixture of 5.6 g of 7,7,9,9-tetramethyl-3-(2,3-epoxypropyl)-1,3,8-triazaspiro[4.5]decane-2,4-dione, 1.46 g of adipic acid and 20 g of concentrated sulphuric acid was stirred for one day at ambient temperature. The reaction mixture was then neutralised with a 10% w/w aqueous solution of potassium carbonate and extracted with ethyl acetate. The solvent was evaporated under reduced pressure from the extract, leaving a residue which was purified by column chromatography through silica gel eluted with a 9:1 by volume mixture of ethyl acetate and triethylamine. The desired Compound No. 125 was obtained in the form of white crystals, melting point 132°–134° C.

EXAMPLE 26

2-Hydroxy-1,3-bis[2-hydroxy-3-(7,7,8,9,9-pentamethyl-2,4-dioxo-1,3,8-triazaspiro[4.5]dec-3-yl)propoxy]propane (Compound No. 171).

A mixture of 12 g of 7,7,8,9,9-pentamethyl-1,3,8-triazaspiro[4.5]decane-2,4-dione, 4.1 g of glycerol α,γ-bis(2,3-epoxypropyl)ether and 0.5 g of sodium hydroxide was refluxed in 60 ml of methanol for 5 hours. After completion of the reaction, the methanol was evaporated under reduced pressure from the reaction mixture, leaving a residue which was purified by column chromatography through silica gel eluted with a 4:1 by volume mixture of ethyl acetate and triethylamine. The desired compound was obtained in the form of white crystals, melting point 175°–177° C.

EXAMPLE 27

Bis{4-[2-hydroxy-3-(7,7,9,9-tetramethyl-2,4-dioxo-1,3,8-triazaspiro[4.5]dec-3-yl)propoxy]phenyl}methane (Compound No. 179)

A mixture of 12 g of 7,7,9,9-tetramethyl-1,3,8-triazaspiro[4.5]decane-2,4-dione, 7 g of bis[p-(2,3-epoxypropoxy)phenyl]methane and 0.1 g (a catalytic amount) of potassium hydroxide was refluxed for 7 hours in 50 ml of methanol. After completion of the reaction, the methanol was evaporated under reduced pressure from the reaction mixture and the residue was dissolved in chloroform. The solution was then washed successively with a 5% w/w aqueous solution of potassium hydroxide and water and dried over anhydrous magnesium sulphate. The solvent was evaporated off under reduced pressure, leaving a residue which was recrystallised from a mixture of benzene and methanol. The desired Compound No. 179 was obtained in the form of white crystals, melting point 113°–118° C. The compound had an $R_f$ value of 0.42 on thin-layer chromatography on silica gel using a 8:1:1 by volume mixture of ethyl acetate, ethanol and triethylamine as developing solvent.

EXAMPLE 28

Bis{4-[2-hydroxy-3-(7,7,8,9,9-pentamethyl-2,4-dioxo-1,3,8-triazaspiro[4.5]dec-3-yl)propoxy]phenyl}methane (Compound No. 180)

A mixture of 7.3 g of 7,7,8,9,9-pentamethyl-1,3,8-triazaspiro[4.5]decane-2,4-dione, 4 g of bis[p-(2,3-epoxypropoxy)phenyl]methane and 0.1 g of potassium hydroxide was refluxed in 50 ml of methanol for 14 hours. After completion of the reaction, the methanol was evaporated under reduced pressure from the reaction mixture and the resulting residue was dissolved in chloroform. The chloroform solution was washed successively with a 5% w/w aqueous solution of potassium hydroxide and water and then dried over anhydrous magnesium sulphate. The solvent was then evaporated under reduced pressure from the chloroform solution to give a residue which was purified first by column chromatography through silica gel eluted with a 10:0.5 by volume mixture of ethyl acetate and triethylamine and then by recrystallisation from benzene. The desired Compound No. 180 was obtained in the form of white crystals melting at 123°–135° C. The compound has an $R_f$ value of 0.3 on thin-layer chromatography on silica gel using a 10:0.5 by volume mixture of ethyl acetate and triethylamine as developing solvent.

EXAMPLE 29

2-Acetoxy-1,3-bis(1-acetyl-7,7,8,9,9-pentamethyl2,4-dioxo-1,3,8-triazaspiro[4.5]dec-3-yl)propane (Compound No. 194)

A solution of 5.3 g of 2-hydroxy-1,3-bis(7,7,8,9,9-pentamethyl2,4-dioxo-1,3,8-triazaspiro[4.5]dec-3-yl)propane (prepared as described in Example 22) in 70 ml of acetic anhydride was heated, with stirring, at 120°–130° C. for 8 hours. The reaction mixture was then condensed by evaporation under reduced pressure and the residue was dissolved in 200 ml of benzene. The benzene solution was washed successively with a 3% w/w aqueous solution of sodium carbonate and water and then dried over anhydrous potassium carbonate. The solvent was removed from the solution to give crystals, which were recrystallised from benzene. The desired Compound No. 194 was obtained in the form of white crystals, melting at 105°–108° C.

EXAMPLE 30

Ethylene glycol bis[2-hydroxy-3-(7,7,9,9-tetramethyl-2,4-dioxo-1,3,8-triazaspiro[4.5]dec-3-yl)propyl]ether (Compound No. 165)

A mixture of 7.7 g of 7,7,9,9-tetramethyl-1,3,8-triazaspiro[4.5]decane-2,4-dione, 2.5 g of ethylene glycol bis(2,3-epoxypropyl)ether and 0.1 g of potassium hydroxide in 80 ml of methanol was refluxed for 11 hours. Insoluble materials were then filtered off and the filtrate was washed with hot methanol. The solution was dried and then the solvent evaporated off. The residue was recrystallised from N,N-dimethylformamide, giving the desired compound in the form of white crystals, melting at 262°–264° C.

EXAMPLE 31

2,2-Bis{4-[2-hydroxy-3-(7,7,8,9,9-pentamethyl2,4-dioxo-1,3,8-triazaspiro[4.5]dec-3-yl)propoxy]cyclohexyl}propane (Compound No. 119)

A mixture of 8 g of 7,7,8,9,9-pentamethyl-1,3,8-triazaspiro[4.5]decane-2,4-dione and 5 g of 2,2-bis[4-(2,3-epoxypropoxy)cyclohexyl]propane was heated at 180°–200° C. for 5 hours. The reaction mixture was then purified by column chromatography through silica gel eluted with a 60:10:1 by volume mixture of ethyl acetate, ethanol and triethylamine and then by recrystallisation from ethyl acetate, giving the desired compound in the form of white crystals melting at 130°–133° C.

EXAMPLE 32

2-Hydroxy-1,3-bis(7,7,9,9-tetramethyl-2,4-dioxo-1,3,8-triazaspiro[4.5]dec-3-yl)propane (Compound No. 163) 5 g of 1,3-dibromo-2-propanol were added dropwise, with stirring, at ambient temperature to a solution of 11.0 g of 7,7,9,9-tetramethyl-1,3,8-triazaspiro[4.5]decane-2,4-dione and 3 g of potassium hydroxide in 50 ml of water. The mixture was stirred at ambient temperature for a further 3 hours and then the crystals which had precipitated were filtered off, dissolved in water and salted out with potassium carbonate. The precipitated crystals were then washed with a small volume of cold water and finally dried in vacuo. Recrystallisation from ethanol gave the desired Compound No. 163 in the form of white crystals melting at 284°–286° C.

EXAMPLE 33

2-Acetoxy-1,3-bis(1,8-diacetyl-7,7,9,9-tetramethyl-2,4-dioxo-1,3,8-triazaspiro[4.5]dec-3-yl)propane (Compound No. 198)

A mixture of 5.0 g of 2-hydroxy-1,3-bis(7,7,9,9-tetramethyl-2,4-dioxo-1,3,8-triazaspiro[4.5]dec-3-yl)propane (produced as described in Example 32) and 70 ml of acetic anhydride was heated, with stirring, at 125°–135° C. The reaction mixture was then condensed by evaporation under reduced pressure and the residue was washed with benzene. The benzene-insoluble crystals were filtered off and found to consist of 2-acetoxy-1,3-bis(8-acetyl-7,7,9,9-tetramethyl-2,4-dioxo-1,3,8-triazaspiro[4.5]dec-3-yl)propane, melting at 286°–288° C. The solvent was evaporated under reduced pressure from the benzene washings and the residue was purified by column chromatography through silica gel eluted with a 20:4:2:1 by volume mixture of ethyl acetate, benzene, ethanol and triethylamine. The desired Compound No. 198 was obtained in the form of a white powder softening at 102°–105° C. Thin-layer chromatography on silica gel using a 20:4:2:1 by volume mixture of ethyl acetate, benzene, ethanol and triethylamine as developing solvent showed the compound to have an $R_f$ value of 0.49.

EXAMPLE 34

Bis[2-hydroxy-3-(7,7,8,9,9-pentamethyl-2,4-dioxo-1,3,8-triazaspiro[4.5]dec-3-yl)propyl]1,10-decanedicarboxylate (Compound No. 199)

A mixture of 4.4 g of 3-(2,3-epoxypropyl)-7,7,8,9,9-pentamethyl-1,3,8-triazaspiro[4.5]decane-2,4-dione and 1.6 g of 1,10-decanedicarboxylic acid was heated at 180° C. for 3 hours. After completion of the reaction, the reaction mixture was dissolved in ethyl acetate, treated with an aqueous alkaline solution and purified by column chromatography through silica gel eluted first with ethyl acetate, then with a 2:1 by volume mixture of ethyl acetate and methanol. The desired compound was obtained in the form of a white powder, melting point 53°-57° C.

EXAMPLE 35

Ethylene glycol bis[2-acetoxy-3-(1,8-diacetyl-7,7,9,9-tetramethyl-2,4-dioxo-1,3,8-triazaspiro[4.5]dec-3-yl)propyl]ether (Compound No. 192)

A mixture of 3.9 g of ethylene glycol bis[2-acetoxy-3-(8-acetyl-7,7,9,9-tetramethyl-2,4-dioxo-1,3,8-triazaspiro[4.5]dec-3-yl)propyl]ether, 30 g of acetic anhydride and 20 ml of triethylamine was heated at 90°-105° C. for 20 hours. After completion of the reaction, the acetic anhydride and triethylamine were evaporated and aqueous ammonia solution was added to the residue. The mixture was extracted with ethyl acetate, washed with water and dried over anhydrous potassium carbonate. The extract was condensed, leaving a residue which was purified by column chromatograph through silica gel eluted with a 6:3:1 by volume mixture of ethyl acetate, benzene and triethylamine. The desired compound was obtained in the form of a pale yellow powder, softening point 42°-49° C.

EXAMPLE 36

2,2-Bis{4-[2-acetoxy-3-(1,8-diacetyl-7,7,9,9-tetramethyl-2,4-dioxo-1,3,8-triazaspiro[4.5]dec-3-yl)propoxy]phenyl}propane (Compound No. 197)

A mixture of 1 g of 2,2-bis{4-[2-acetoxy-3-(8-acetyl-7,7,9,9-tetramethyl-2,4-dioxo-1,3,8-triazaspiro[4.5]dec-3-yl)propoxy]phenyl}propane, 10 g of acetic anhydride and 20 ml of triethylamine was heated at 90°-100° C. for 10 hours. After completion of the reaction the excess acetic anhydride and triethylamine were evaporated under reduced pressure and aqueous ammonia solution was added to the residue. The mixture was extracted with ethyl acetate, washed with water and dried over anhydrous potassium carbonate. The extract was condensed, leaving a residue which was purified by column chromatography through silica gel eluted with a 6:6:1 by volume mixture of ethyl acetate, benzene and triethylamine. The desired compound was obtained in the form of a pale yellow powder, softening point 102°-106° C.

EXAMPLE 37

2,2-Bis[4-{4-lauroyloxy-3-(7,7,8,9,9-pentamethyl-2,4-dioxo-1,3,8-triazaspiro[4.5]dec-3-yl)propoxy}phenyl]propane (Compound No. 39)

A mixture of 4.0 g of 2,2-bis[4-{2-hydroxy-3-(7,7,8,9,9-pentamethyl-2,4-dioxo-1,3,8-triazaspiro[4.5]dec-3-yl)propoxy}phenyl]propane and 7.5 g of lauric anhydride was refluxed in 15 ml of xylene for 48 hours. After completion of the reaction, the reaction mixture was neutralized with aqueous ammonia water and extracted with ethyl acetate. The extract was washed with ethyl acetate and dried over magnesium sulfate. The solvent was removed from the extract, leaving a residue which was purified first by column chromatography through silica gel eluted with ethyl acetate, then by recrystallization from benzene. The desired compound was obtained in the form of white crystals, melting point 113°-117° C.

EXAMPLE 38

Ethylene glycol bis[2-acetoxy-3-(8-acetyl-7,7,9,9-tetramethyl-2,4-dioxo-1,3,8-triazaspiro[4.5]dec-3-yl)propyl]ether (Compound No. 200)

A mixture of 5 g of ethylene glycol bis[2-hydroxy-3-(7,7,9,9-tetramethyl-2,4-dioxo-1,3,8-triazaspiro[4.5]dec-3-yl)propyl]ether and 100 g of acetic anhydride was refluxed for 30 minutes, then heated at 100°-110° C. for 3 hours. After completion of the reaction, the excess acetic anhydride was evaporated and an aqueous solution of potassium carbonate was added to the residue. The mixture was extracted with chloroform and dried over anhydrous potassium carbonate. The chloroform solution was condensed, leaving a residue which was purified by column chromatography through silica gel eluted with a 8:2:1 by volume mixture of ethyl acetate, benzene and triethylamine. The desired compound was obtained in the form of a white powder, softening point 87°-90° C.

EXAMPLE 39

Stabilisation of polypropylene

Mixtures were made from 100 parts of polypropylene powder (MFI=18), 0.2 part of stearyl 3-(3,5-di-t-butyl-4-hydroxyphenyl)propionate, as antioxidant, and 0.25 part of each in turn of the stabilising compounds of the invention listed in Table 1. The resulting mixtures were then blended and homogenised using a Brabender Plastograph at 200° C. for 10 minutes and then pressed in a laboratory press to form sheets of thickness 2-3 mm. The sheets were heated at 260° C. and then subjected to a pressure of 12 tons by means of a hydraulic press and placed immediately into cold water to form films of thickness 0.5 mm. The procedure was then repeated to obtain films of thickness 0.1 mm. These films were cut to form test specimens of size 50×120 mm.

Each test specimen was exposed to light in a Sunshine Weather Meter at a black panel temperature of 63°±3° C. and examined periodically to determine the percentage elongation at break. The test results were expressed as a ratio of the time required for the test specimen to reach 50% elongation at break when a stabiliser was employed to the same time when no stabiliser was employed. The results obtained are shown in Table 1.

Table 1

| Stabilizer Compound No. | Ratio |
| --- | --- |
| 1 | 4.8 |
| 32 | 4.6 |
| 34 | 4.7 |
| 35 | 4.5 |
| 37 | 5.6 |
| 45 | 3.2 |
| 68 | 4.2 |
| 92 | 5.5 |
| 104 | 3.1 |

Table 1-continued

| Stabilizer Compound No. | Ratio |
|---|---|
| 107 | 4.2 |
| 118 | 5.0 |
| 125 | 5.8 |
| 126 | 4.6 |
| 130 | 4.4 |
| 147 | 4.8 |
| 169 | 4.0 |
| 171 | 5.1 |
| 174 | 4.5 |
| 177 | 5.3 |
| 179 | 4.3 |
| 180 | 4.7 |
| 187 | 5.3 |
| 188 | 3.6 |
| 194 | 6.8 |
| none | 1.0 |

EXAMPLE 40

Stabilisation of polyurethane 100 parts of an aromatic polyester-type polyurethane (sold under the trade name Estane 5707 by Goodrich Company) and 0.5 part of each in turn of the stabilising compounds of the invention were dissolved in 400 parts of N,N-dimethylformamide. The solution was poured onto a glass plate to give a film of thickness about 500 microns. After air-drying, the film was dried further at 60° C. for 10 minutes and at 140° C. for 6 minutes, giving a film about 100 microns thick. The film was then subjected to ultraviolet radiation in a Sunshine Carbon Arc Weather Meter for 200 hours and the degree of yellowing was measured. The results are shown in Table 2, which also gives the results of control experiments in which no stabiliser was used or in which the known stabiliser Tinuvin P was used.

Table 2

| Compound No. | Yellowness Index | |
|---|---|---|
| | Before Irradiation | After Irradiation |
| 1 | 1.8 | 18.6 |
| 32 | 2.0 | 22.1 |
| 37 | 1.9 | 20.4 |
| 45 | 1.9 | 21.5 |
| 68 | 1.8 | 19.4 |
| 92 | 1.8 | 20.1 |
| 104 | 2.1 | 21.9 |
| 118 | 1.8 | 17.7 |
| 130 | 2.0 | 21.2 |
| 147 | 1.8 | 19.7 |
| 169 | 2.1 | 23.4 |
| 171 | 1.8 | 17.9 |
| 174 | 2.1 | 21.5 |
| 177 | 1.9 | 19.9 |
| 180 | 1.8 | 21.3 |
| none | 2.1 | 46.8 |
| TinuvinP | 1.9 | 34.9 |

EXAMPLE 41

Stabilisation of Acrylonitrile-butadiene-styrene(ABS) resin

Mixtures were made from 100 parts of ABS resin (available under the trade name Kane Ace B-12 from Kanegafuchi Chemical Industries Limited) and 0.5 part of each in turn of the stabilising compounds of the invention listed in Table 3. The resulting mixtures were blended and homogenised on rolls at 165° C. for 4 minutes, giving sheets each about 0.5 mm thick. The sheets were pressed for 1 minute at 190° C. to a thickness of 0.5 mm and then dumbell-shaped test pieces were prepared and subjected to ultraviolet radiation in a Sunshine Carbon Arc Weather Meter for 50 hours. After irradiation, the test pieces were subjected to a tensile test to determine the percentage retention of elongation and of tensile strength. The results are shown in Table 3.

Table 3

| Compound No. | Retention of Elongation (%) | Retention of Tensile Strength (%) |
|---|---|---|
| 1 | 58 | 74 |
| 37 | 63 | 78 |
| 68 | 61 | 75 |
| 118 | 64 | 76 |
| 130 | 55 | 73 |
| 147 | 54 | 72 |
| 174 | 59 | 74 |
| 177 | 57 | 73 |
| 180 | 56 | 74 |
| none | 17 | 69 |
| Tinuvin 327 | 43 | 67 |

We claim:

1. Compounds of formula (I):

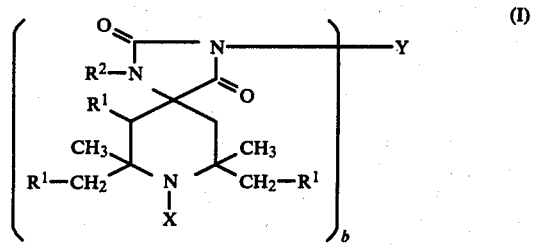

wherein:

$R^1$ represents a hydrogen atom or a methyl group;

$R^2$ represents a hydrogen atom, an alkyl group having from 1 to 18 carbon atoms, an allyl group, an acetyl group or a benzyl group;

X represents a hydrogen atom, an alkyl group having from 1 to 18 carbon atoms, an alkenyl group having 3 or 4 carbon atoms, a cyanoalkyl group having 2 or 3 carbon atoms, a 2,3-epoxypropyl group, a benzyl group, an aliphatic acyl group having up to 18 carbon atoms, or a group of formula

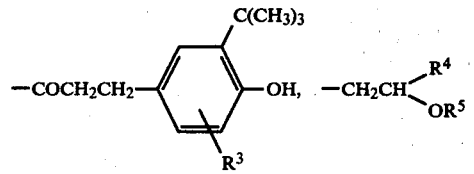

or —$CH_2COOR^6$ wherein:

$R^3$ represents an alkyl group having from 1 to 4 carbon atoms;

$R^4$ represents a hydrogen atom, a methyl group or a phenyl group;

$R^5$ represents a hydrogen atom, an alkyl group having from 1 to 8 carbon atoms, an allyl group, a benzyl group or an aliphatic, aromatic, araliphatic or alicyclic acyl group having up to 18 carbon atoms wherein the aromatic moiety is unsubstituted or has one or more $C_1$-$C_4$ alkyl and/or hydroxy substituents; and R⁶ represents an alkyl group having from 1 to 18 carbon atoms, an alkenyl group having 3 or 4 carbon atoms or a phenyl group; b is 2 or 3; and when b=2:

Y represents one of the groups of formula —CH₂CH(OZ)CH₂-[OCH₂—CH(OZ)CH₂]₂—, —CH₂CH(OZ)CH₂-[OCH₂C(R⁷)H]ₘ—OCH₂CH(OZ)CH₂—, —CH₂CH(OZ)CH₂-[OWO—CH₂CH(OZ)CH₂]ₙ—, or CH₂CH(OZ)—CH₂— in which:

m and n each represents an integer of from 1 to 10;
R⁷ represents a hydrogen atom or a methyl group;
W represents one of the groups of formula

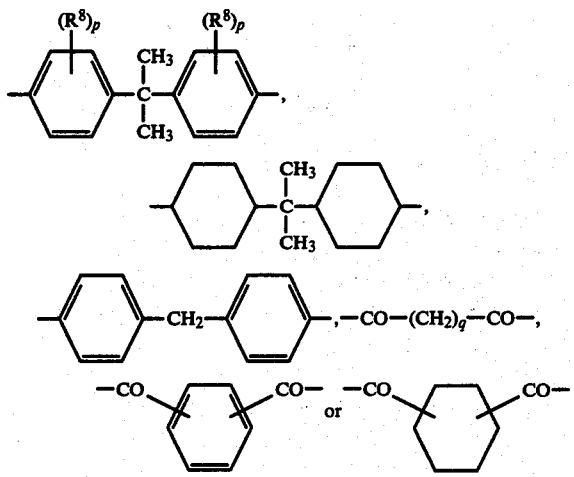

wherein:
p is 0, 1 or 2;
R⁸ represents a halogen atom; and
q is an integer of from 1 to 10; and Z represents a hydrogen atom, an alkyl group having from 1 to 18 carbon atoms, an allyl group, a benzyl group, an aliphatic, aromatic, araliphatic or alicyclic acyl group having up to 18 carbon atoms (wherein the aromatic moiety is unsubstituted or has one or more C₁-C₄ alkyl and/or hydroxy substituents), or one of the groups of formulae

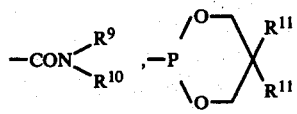

or —P(OR¹²)₂ in which:
R⁹ represents a hydrogen atom or an alkyl group having from 1 to 4 carbon atoms;
R¹⁰ represents an alkyl group having from 1 to 18 carbon atoms, a phenyl group, a substituted phenyl group having one or more methyl, chlorine and/or bromine substituents, a naphthyl group or a cyclohexyl group;
R¹¹ represents a hydrogen atom or an alkyl group having from 1 to 4 carbon atoms; and
R¹² represents an alkyl group having from 1 to 4 carbon atoms, a phenyl group or a group of formula

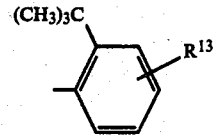

in which R¹³ represents a hydrogen atom or an alkyl group having from 1 to 4 carbon atoms;
when b=3;
Y represents one of the groups of formulae

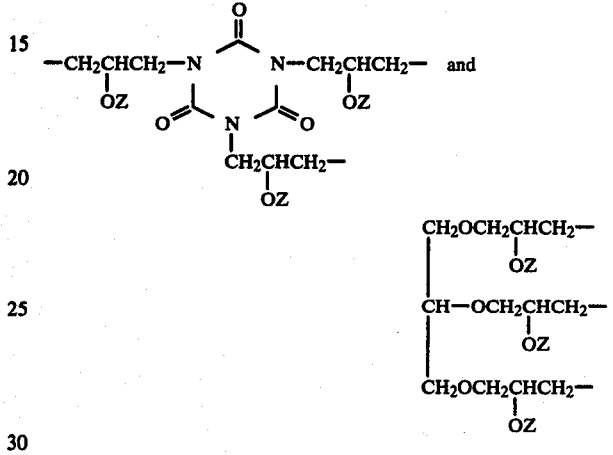

in which Z is as defined above; and acid addition salts thereof.

2. Compounds as claimed in claim 1, wherein R¹ represents a hydrogen atom.

3. Compounds as claimed in claim 1, wherein R² represents a hydrogen atom or an acetyl group.

4. Compounds as claimed in claim 1, wherein Y represents a group of formula —CH₂CH(OZ)CH₂-[OWO—CH₂CH(OZ)CH₂]ᵣ— wherein W and Z are as defined in claim 1 and r is 0 or 1 or a group of formula —CH₂CH(OZ)CH₂—OCH₂CH₂—OCH₂CH(OZ)CH₂— in which Z is as defined in claim 1.

5. Compounds as claimed in claim 4, wherein r is 1 and W is one of the groups of formula

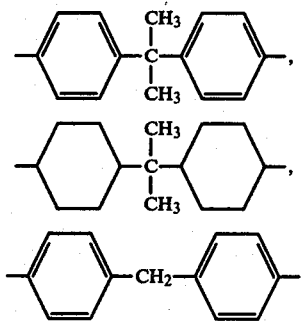

or —CO—(CH₂)q—CO— in which q is as defined in claim 1.

6. Compounds as claimed in claim 1, wherein Z represents a hydrogen atom, an alkanoyl group having from 2 to 18 carbon atoms or a benzoyl group.

7. Compounds as claimed in claim 1, wherein X represents a hydrogen atom, an alkyl group having 1 to 4 carbon atoms, an acetyl group or a group of formula —CH₂CH₂OR¹⁸ wherein R¹⁸ represents aa hydrogen atom, an alkanoyl group having from 2 to 18 carbon atoms or a benzoyl group.

8. Compounds as claimed in claim 7, wherein X represents a hydrogen atom or a methyl group.

9. A polymer composition stabilized against photo- and thermal-deterioration, wherein there is incorporated, in an amount sufficient to prevent said deterioration, a hydantoin derivative having the general formula (I):

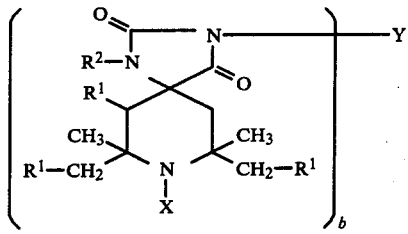

wherein:

R¹ represents a hydrogen atom or a methyl group;
R² represents a hydrogen atom, an alkyl group having from 1 to 18 carbon atoms, an allyl group, an acetyl group or a benzyl group;
X represents a hydrogen atom, an alkyl group having from 1 to 18 carbon atoms, an alkenyl group having 3 or 4 carbon atoms, a cyanoalkyl group having 2 or 3 carbon atoms, a 2,3-epoxypropyl group, a benzyl group, an aliphatic acyl group having up to 18 carbon atoms, or a group of formula

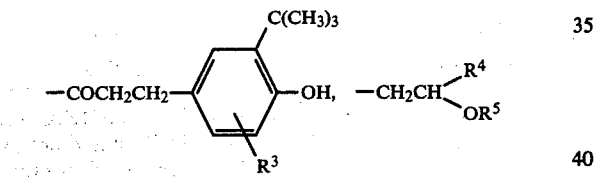

or —CH₂COOR⁶ wherein:
R³ represents an alkyl group having from 1 to 4 carbon atoms;
R⁴ represents a hydrogen atom, a methyl group or a phenyl group;
R⁵ represents a hydrogen atom, an alkyl group having from 1 to 8 carbon atoms, an allyl group, a benzyl group or an aliphatic, aromatic, araliphatic or alicyclic acyl group having up to 18 carbon atoms wherein the aromatic moiety is unsubstituted or has one or more C₁-C₄ alkyl and/or hydroxy substituents; and
R⁶ represents an alkyl group having from 1 to 18 carbon atoms, an alkenyl group having 3 or 4 carbon atoms or a phenyl group;
b is 2 or 3; and
when b=2:
Y represents one of the groups of formula —CH₂CH(OZ)CH₂-[O-CH₂—CH(OZ)CH₂]₂—, —CH₂CH(OZ)CH₂-[OCH₂C(R⁷)H]ₘ—OCH₂CH(OZ)—CH₂—, —CH₂CH(OZ)CH₂—[OWO—CH₂CH(OZ)CH₂]ₙ—, or CH₂CH(OZ)—CH₂—in which:
m and n each represents an integer of from 1 to 10;
R⁷ represents a hydrogen atom or a methyl group;
W represents one of the groups of formula

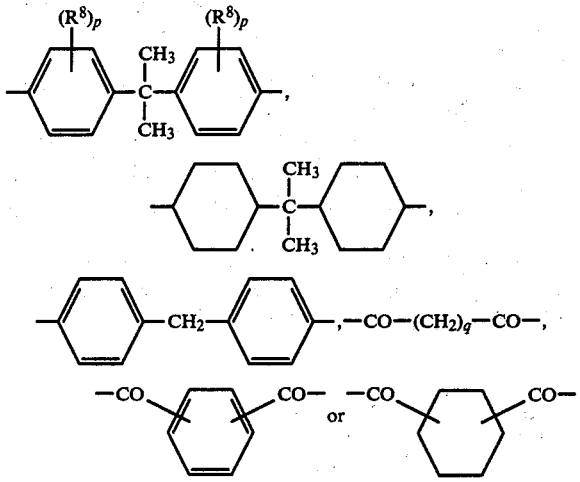

wherein:
p is 0, 1 or 2;
R⁸ represents a halogen atom; and
q is an integer of from 1 to 10; and
Z represents a hydrogen atom, an alkyl group having from 1 to 18 carbon atoms, an allyl group, a benzyl group, an aliphatic, aromatic, araliphatic or alicyclic acyl group having up to 18 carbon atoms wherein the aromatic moiety is unsubstituted or has one or more C₁-C₄ alkyl and/or hydroxy substituents, or one of the groups of formulae

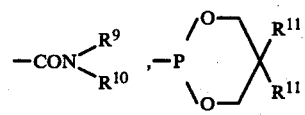

or —P(OR¹²)₂ in which:
R⁹ represents a hydrogen atom or an alkyl group having from 1 to 4 carbon atoms;
R¹⁰ represents an alkyl group having from 1 to 18 carbon atoms, a phenyl group, a substituted phenyl group having one or more methyl, chlorine and/or bromine substituents, a naphthyl group or a cyclohexyl group;
R¹¹ represents a hydrogen atom or an alkyl group having from 1 to 4 carbon atoms; and
R¹² represents an alkyl group having from 1 to 4 carbon atoms, a phenyl group or a group of formula

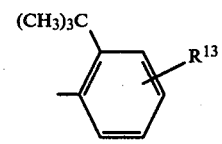

in which R¹³ represents a hydrogen atom or an alkyl group having from 1 to 4 carbon atoms;
when b=3:
Y represents one of the groups of formulae

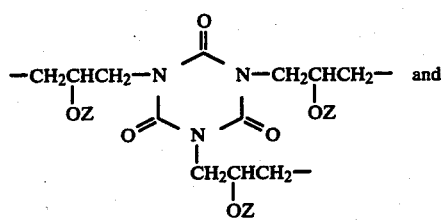 and

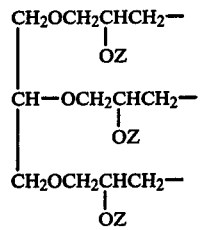

in which Z is as defined above; or an acid addition salt thereof.

10. A polymer composition as claimed in claim 9, wherein said hydantoin derivative or acid addition salt thereof is incorporated in an amount of from 0.01 to 5.0% by weight, based upon the amount of polymer.

11. A polymer composition as claimed in claim 10, wherein said polymer is selected from the group consisting of olefin polymers, polyamides, diene polymers, styrene polymers and polyurethanes.

* * * * *